US012482559B2

(12) United States Patent
Martin et al.

(10) Patent No.: US 12,482,559 B2
(45) Date of Patent: Nov. 25, 2025

(54) SYSTEMS AND METHODS FOR EMS DEVICE COMMUNICATIONS INTERFACE

(71) Applicant: ZOLL Medical Corporation, Chelmsford, MA (US)

(72) Inventors: Michael S Martin, Lakewood, CO (US); Chad Ashmore, Frederick, CO (US); Eric A Deines, Broomfield, CO (US); Gary A Freeman, Waltham, MA (US); Joseph L Helmick, Centennial, CO (US); Thomas E Kaib, Irwin, PA (US); Richard A Rattanni, Verona, PA (US); C. Shane Reid, Denver, CO (US); Jeremy R Soller, Aurora, CO (US); Shane S Volpe, Saltsburg, PA (US); Gary Ruggiero, Lexington, MA (US); Frederick J Geheb, Lenexa, KS (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 694 days.

(21) Appl. No.: 17/447,955

(22) Filed: Sep. 17, 2021

(65) Prior Publication Data

US 2022/0020491 A1 Jan. 20, 2022

Related U.S. Application Data

(63) Continuation of application No. 16/702,868, filed on Dec. 4, 2019, and a continuation of application No.
(Continued)

(51) Int. Cl.

| | |
|---|---|
| *G16H 40/67* | (2018.01) |
| *A61N 1/372* | (2006.01) |

(Continued)

(52) U.S. Cl.
CPC ......... *G16H 40/67* (2018.01); *A61N 1/37217* (2013.01); *G16H 10/60* (2018.01); *G16H 15/00* (2018.01)

(58) Field of Classification Search
None
See application file for complete search history.

(56) References Cited

U.S. PATENT DOCUMENTS

| | | | |
|---|---|---|---|
| 4,649,930 | A | 3/1987 | Groch et al. |
| 5,085,224 | A | 2/1992 | Galen et al. |

(Continued)

FOREIGN PATENT DOCUMENTS

| | | |
|---|---|---|
| CN | 1750857 | 3/2006 |
| JP | 08-126616 | 5/1996 |

(Continued)

OTHER PUBLICATIONS

European Examination Report for European Patent Application 19172265.1, dated Nov. 15, 2021, 8 pages.

(Continued)

*Primary Examiner* — Jennifer Pitrak McDonald
*Assistant Examiner* — Jennifer L. Ghand
(74) *Attorney, Agent, or Firm* — Lando & Anastasi, LLP

(57) ABSTRACT

A system for providing role-based data feeds for a plurality of patient caregivers includes a portable central device and a patient data display screen. The central device is configured to obtain the medical data via one or more sensors and/or electrodes configured to couple to the patient and provide the medical data to mobile devices, optionally as multiple role-based data feeds. The central device may include software and hardware configured to feed the medical data to the mobile devices via multiple role-based data feeds. The patient data display screen is configured to display the medical data. Each mobile device may identify
(Continued)

an associated type of medical data by displaying a screen enabling a caregiver to select the associated type of medical data based on their role, or may receive a respective role-based data feed from the central device. Each mobile device is configured to display the received medical data.

23 Claims, 59 Drawing Sheets

Related U.S. Application Data

15/959,404, filed on Apr. 23, 2018, now Pat. No. 11,109,816, which is a continuation of application No. 13/647,744, filed on Oct. 9, 2012, now Pat. No. 10,765,873, which is a continuation of application No. PCT/US2011/031868, filed on Apr. 9, 2011, which is a continuation of application No. 12/840,129, filed on Jul. 20, 2010, now abandoned.

(60) Provisional application No. 61/434,812, filed on Jan. 20, 2011, provisional application No. 61/322,675, filed on Apr. 9, 2010, provisional application No. 61/227,187, filed on Jul. 21, 2009.

(51) Int. Cl.
*G16H 10/60* (2018.01)
*G16H 15/00* (2018.01)

(56) References Cited

U.S. PATENT DOCUMENTS

| | | | |
|---|---|---|---|
| 5,224,485 | A | 7/1993 | Powers et al. |
| 5,319,363 | A | 6/1994 | Welch et al. |
| 5,333,617 | A | 8/1994 | Hafner |
| 5,343,869 | A | 9/1994 | Pross et al. |
| 5,456,261 | A | 10/1995 | Luczyk |
| 5,494,051 | A | 2/1996 | Schneider, Sr. |
| 5,511,553 | A | 4/1996 | Segalowitz |
| 5,534,917 | A | 7/1996 | MacDougall |
| 5,544,661 | A | 8/1996 | Davis et al. |
| 5,549,659 | A | 8/1996 | Johansen et al. |
| 5,593,426 | A | 1/1997 | Morgan et al. |
| 5,782,878 | A | 7/1998 | Morgan et al. |
| 5,850,352 | A | 12/1998 | Moezzi et al. |
| 5,959,529 | A | 9/1999 | Kail, IV |
| 6,083,248 | A | 7/2000 | Thompson |
| 6,115,052 | A | 9/2000 | Freeman et al. |
| 6,117,073 | A | 9/2000 | Jones et al. |
| 6,141,584 | A | 10/2000 | Rockwell et al. |
| 6,236,737 | B1 | 5/2001 | Gregson et al. |
| 6,301,502 | B1 | 10/2001 | Owen et al. |
| 6,321,113 | B1 | 11/2001 | Parker et al. |
| 6,347,299 | B1 | 2/2002 | Holzman et al. |
| 6,390,996 | B1 | 5/2002 | Halperin et al. |
| 6,398,744 | B2 | 6/2002 | Bystrom et al. |
| 6,405,083 | B1 | 6/2002 | Rockwell et al. |
| 6,481,887 | B1 | 11/2002 | Mirabella |
| 6,532,381 | B2 | 3/2003 | Bayer et al. |
| 6,544,173 | B2 | 4/2003 | West et al. |
| 6,553,262 | B1 | 4/2003 | Lang et al. |
| 6,604,115 | B1 | 8/2003 | Gary, Jr. et al. |
| 6,681,003 | B2 | 1/2004 | Linder et al. |
| 6,727,814 | B2 | 4/2004 | Saltzstein et al. |
| 6,741,977 | B1 | 5/2004 | Nagaya et al. |
| 6,747,556 | B2 | 6/2004 | Medema et al. |
| 6,827,695 | B2 | 12/2004 | Palazzolo et al. |
| 6,829,501 | B2 | 12/2004 | Nielsen et al. |
| 6,937,150 | B2 | 8/2005 | Medema et al. |
| 6,957,102 | B2 | 10/2005 | Silver et al. |
| 6,968,294 | B2 | 11/2005 | Gutta et al. |
| 6,970,737 | B1 | 11/2005 | Brodnick et al. |
| 6,984,208 | B2 | 1/2006 | Zheng |
| 6,993,386 | B2 | 1/2006 | Lin et al. |
| 7,006,865 | B1 | 2/2006 | Cohen et al. |
| 7,058,204 | B2 | 6/2006 | Hildreth et al. |
| 7,060,031 | B2 | 6/2006 | Webb et al. |
| 7,095,401 | B2 | 8/2006 | Liu et al. |
| 7,110,569 | B2 | 9/2006 | Brodsky et al. |
| 7,118,542 | B2 | 10/2006 | Palazzolo et al. |
| 7,120,488 | B2 | 10/2006 | Nova et al. |
| 7,122,014 | B2 | 10/2006 | Palazzolo et al. |
| 7,129,836 | B2 | 10/2006 | Lawson et al. |
| 7,143,044 | B2 | 11/2006 | Zadrozny et al. |
| 7,162,306 | B2 | 1/2007 | Caby et al. |
| 7,212,109 | B2 | 5/2007 | Morita et al. |
| 7,225,131 | B1 | 5/2007 | Bangalore et al. |
| 7,227,526 | B2 | 6/2007 | Hildreth et al. |
| 7,231,258 | B2 | 6/2007 | Moore et al. |
| 7,233,905 | B1 | 6/2007 | Hutton et al. |
| 7,274,290 | B2 | 9/2007 | Morita et al. |
| 7,295,871 | B2 | 11/2007 | Halperin et al. |
| 7,301,464 | B2 | 11/2007 | Coulter |
| 7,333,090 | B2 | 2/2008 | Tanaka et al. |
| 7,340,077 | B2 | 3/2008 | Gokturk et al. |
| 7,379,563 | B2 | 5/2008 | Shamaie |
| 7,379,566 | B2 | 5/2008 | Hildreth |
| 7,382,895 | B2 | 6/2008 | Bramblet et al. |
| 7,389,591 | B2 | 6/2008 | Jaiswal et al. |
| 7,412,395 | B2 | 8/2008 | Rowlandson |
| 7,421,093 | B2 | 9/2008 | Hildreth et al. |
| 7,421,647 | B2 | 9/2008 | Reiner |
| 7,430,312 | B2 | 9/2008 | Gu |
| 7,444,315 | B2 | 10/2008 | Wu |
| 7,488,293 | B2 | 2/2009 | Marcovecchio et al. |
| 7,499,862 | B1 | 3/2009 | Bangalore et al. |
| 7,501,995 | B2 | 3/2009 | Morita et al. |
| 7,558,622 | B2 | 7/2009 | Tran |
| 7,607,079 | B2 | 10/2009 | Reiner |
| 7,627,372 | B2 | 12/2009 | Vaisnys et al. |
| 7,643,862 | B2 | 1/2010 | Schoenefeld |
| 7,650,291 | B2 | 1/2010 | Rosenfeld et al. |
| 7,668,340 | B2 | 2/2010 | Cohen et al. |
| 7,668,736 | B2 | 2/2010 | Jones et al. |
| 7,686,768 | B2 | 3/2010 | Bodecker et al. |
| 7,694,240 | B2 | 4/2010 | Kariathungal et al. |
| 7,698,002 | B2 | 4/2010 | Music et al. |
| 7,801,332 | B2 | 9/2010 | Albertson et al. |
| 7,805,191 | B2 | 9/2010 | Walker et al. |
| 7,813,784 | B2 | 10/2010 | Marquart et al. |
| 7,818,177 | B1 | 10/2010 | Bangalore et al. |
| 7,945,076 | B2 | 5/2011 | Delean |
| 7,961,910 | B2 | 6/2011 | Lee et al. |
| 7,971,156 | B2 | 6/2011 | Albertson et al. |
| 7,987,069 | B2 | 7/2011 | Rodgers et al. |
| 7,996,793 | B2 | 8/2011 | Latta et al. |
| 8,002,700 | B2 | 8/2011 | Ferek-Petric et al. |
| 8,009,867 | B2 | 8/2011 | Mathe et al. |
| 8,010,190 | B2 | 8/2011 | Olson et al. |
| 8,081,165 | B2 | 12/2011 | Reiner |
| 8,094,873 | B2 | 1/2012 | Kelusky et al. |
| 8,140,154 | B2 | 3/2012 | Donnelly et al. |
| 8,149,108 | B2 | 4/2012 | Hamel et al. |
| 8,184,092 | B2 | 5/2012 | Cox et al. |
| 8,185,623 | B2 | 5/2012 | Lewis et al. |
| 8,199,009 | B2 | 6/2012 | Brunetti |
| 8,203,454 | B2 | 6/2012 | Knight et al. |
| 8,212,669 | B2 | 7/2012 | Brunetti et al. |
| 8,213,680 | B2 | 7/2012 | Fitzgibbon et al. |
| 8,255,238 | B2 | 8/2012 | Powell et al. |
| 8,260,631 | B2 | 9/2012 | Morita et al. |
| 8,284,157 | B2 | 10/2012 | Markovic et al. |
| 8,290,249 | B2 | 10/2012 | Mathe et al. |
| 8,295,542 | B2 | 10/2012 | Albertson et al. |
| 8,334,842 | B2 | 12/2012 | Markovic et al. |
| 8,340,432 | B2 | 12/2012 | Mathe et al. |
| 8,351,652 | B2 | 1/2013 | Mathe |
| 8,374,423 | B2 | 2/2013 | Lee et al. |
| 8,379,101 | B2 | 2/2013 | Mathe et al. |
| 8,380,631 | B2 | 2/2013 | Dala et al. |
| 8,385,596 | B2 | 2/2013 | Latta et al. |
| 8,386,011 | B2 | 2/2013 | Wieczorek |

(56) References Cited

U.S. PATENT DOCUMENTS

| | | | |
|---|---|---|---|
| 8,457,353 | B2 | 6/2013 | Reville et al. |
| 8,465,108 | B2 | 6/2013 | Markovic et al. |
| 8,520,027 | B2 | 8/2013 | Itkowitz et al. |
| 8,543,240 | B2 | 9/2013 | Itkowitz et al. |
| 8,565,479 | B2 | 10/2013 | Gurman et al. |
| 8,570,373 | B2 | 10/2013 | Variyath et al. |
| 8,605,165 | B2 | 12/2013 | Hanina et al. |
| 8,631,355 | B2 | 1/2014 | Murillo et al. |
| 8,652,038 | B2 | 2/2014 | Tran et al. |
| 8,666,781 | B2 | 3/2014 | Hanina et al. |
| 8,682,489 | B2 | 3/2014 | Itkowitz et al. |
| 8,712,793 | B2 | 4/2014 | Jones et al. |
| 8,745,541 | B2 | 6/2014 | Wilson et al. |
| 8,788,378 | B2 | 7/2014 | Hutton et al. |
| 8,816,846 | B2 | 8/2014 | Rosnov |
| 8,817,085 | B2 | 8/2014 | Hiltl et al. |
| 8,830,054 | B2 | 9/2014 | Weiss |
| 8,918,209 | B2 | 12/2014 | Rosenstein et al. |
| 8,930,040 | B2 | 1/2015 | Gompert et al. |
| 8,935,003 | B2 | 1/2015 | Itkowitz et al. |
| 8,983,392 | B2 | 3/2015 | Ren et al. |
| 8,996,173 | B2 | 3/2015 | Itkowitz et al. |
| 9,235,977 | B2 | 1/2016 | Deutsch |
| 9,282,297 | B2 | 3/2016 | Siann et al. |
| 9,311,763 | B2 | 4/2016 | Gompert et al. |
| 9,436,286 | B2 | 9/2016 | Padovani et al. |
| 9,785,744 | B2 | 10/2017 | Johnson et al. |
| 9,848,058 | B2 | 12/2017 | Johnson et al. |
| 9,911,166 | B2 | 3/2018 | Reid et al. |
| 10,049,281 | B2 | 8/2018 | Verano et al. |
| 10,117,721 | B2 | 11/2018 | Tripathi et al. |
| 2001/0044732 | A1 | 11/2001 | Maus et al. |
| 2002/0004729 | A1 | 1/2002 | Zak et al. |
| 2002/0198473 | A1 | 12/2002 | Kumar et al. |
| 2003/0058111 | A1 | 3/2003 | Lee et al. |
| 2003/0146926 | A1 | 8/2003 | Valdes |
| 2003/0212311 | A1 | 11/2003 | Nova et al. |
| 2004/0088374 | A1 | 5/2004 | Webb et al. |
| 2004/0122476 | A1 | 6/2004 | Wung |
| 2004/0127774 | A1 | 7/2004 | Moore et al. |
| 2004/0204743 | A1 | 10/2004 | McGrath et al. |
| 2005/0060186 | A1 | 3/2005 | Blowers et al. |
| 2005/0113996 | A1 | 5/2005 | Pillar et al. |
| 2005/0203384 | A1 | 9/2005 | Sati et al. |
| 2005/0204310 | A1 | 9/2005 | De Zwart et al. |
| 2005/0249239 | A1 | 11/2005 | Pierce et al. |
| 2005/0255434 | A1 | 11/2005 | Lok et al. |
| 2005/0262533 | A1 | 11/2005 | Hart et al. |
| 2005/0267354 | A1 | 12/2005 | Marquart et al. |
| 2005/0277872 | A1 | 12/2005 | Colby et al. |
| 2006/0015044 | A1* | 1/2006 | Stavland .............. A61B 5/0809 601/41 |
| 2006/0052684 | A1 | 3/2006 | Takahashi et al. |
| 2006/0059012 | A1 | 3/2006 | Thompson |
| 2006/0135859 | A1 | 6/2006 | Iliff |
| 2006/0137699 | A1 | 6/2006 | Moore et al. |
| 2006/0149597 | A1 | 7/2006 | Powell et al. |
| 2006/0212085 | A1 | 9/2006 | Fischell et al. |
| 2006/0247549 | A1 | 11/2006 | Chan |
| 2006/0287586 | A1 | 12/2006 | Murphy |
| 2007/0016008 | A1 | 1/2007 | Schoenefeld |
| 2007/0041626 | A1 | 2/2007 | Weiss et al. |
| 2007/0065793 | A1 | 3/2007 | Benja-Athon et al. |
| 2007/0100213 | A1 | 5/2007 | Dossas et al. |
| 2007/0118400 | A1 | 5/2007 | Morita et al. |
| 2007/0135866 | A1 | 6/2007 | Baker et al. |
| 2007/0198632 | A1 | 8/2007 | Peart et al. |
| 2007/0276270 | A1 | 11/2007 | Tran |
| 2007/0276300 | A1 | 11/2007 | Olson et al. |
| 2008/0018454 | A1 | 1/2008 | Chan et al. |
| 2008/0021730 | A1 | 1/2008 | Holla et al. |
| 2008/0058660 | A1 | 3/2008 | Fischell et al. |
| 2008/0104547 | A1 | 5/2008 | Morita et al. |
| 2008/0114614 | A1 | 5/2008 | Mahesh et al. |
| 2008/0114615 | A1 | 5/2008 | Mahesh et al. |
| 2009/0070148 | A1* | 3/2009 | Skocic .................... G06F 16/24 705/3 |
| 2009/0146848 | A1 | 6/2009 | Ghassabian |
| 2009/0195382 | A1 | 8/2009 | Hall |
| 2009/0198696 | A1 | 8/2009 | Banks |
| 2009/0222539 | A1* | 9/2009 | Lewis .................... G16H 40/67 600/509 |
| 2009/0259113 | A1 | 10/2009 | Liu et al. |
| 2009/0299204 | A1 | 12/2009 | Hsieh et al. |
| 2010/0017471 | A1 | 1/2010 | Brown et al. |
| 2010/0228262 | A1 | 9/2010 | Cully et al. |
| 2010/0234908 | A1* | 9/2010 | Didon ................ A61N 1/39044 434/265 |
| 2010/0235782 | A1 | 9/2010 | Powell et al. |
| 2010/0305972 | A1* | 12/2010 | McLaren ............... G06Q 10/06 705/3 |
| 2010/0306858 | A1* | 12/2010 | McLaren ................ G16Z 99/00 726/28 |
| 2011/0001605 | A1 | 1/2011 | Kiani et al. |
| 2011/0060378 | A1 | 3/2011 | Tuysserkani |
| 2011/0099031 | A1 | 4/2011 | Nair |
| 2011/0117878 | A1* | 5/2011 | Barash .................... H04W 4/12 340/539.12 |
| 2011/0157480 | A1 | 6/2011 | Curl |
| 2011/0169644 | A1 | 7/2011 | Muhsin et al. |
| 2011/0172550 | A1 | 7/2011 | Martin et al. |
| 2011/0184759 | A1 | 7/2011 | Selker et al. |
| 2011/0213342 | A1 | 9/2011 | Tripathi et al. |
| 2011/0227741 | A1 | 9/2011 | Jeon |
| 2011/0284004 | A1 | 11/2011 | Silver et al. |
| 2011/0295078 | A1 | 12/2011 | Reid et al. |
| 2012/0029932 | A1 | 2/2012 | Stein et al. |
| 2012/0059671 | A1 | 3/2012 | Park et al. |
| 2012/0075103 | A1 | 3/2012 | Powell et al. |
| 2012/0116986 | A1 | 5/2012 | Ault |
| 2012/0329420 | A1 | 12/2012 | Zotti et al. |
| 2013/0173300 | A1 | 7/2013 | Hyde et al. |
| 2014/0009378 | A1 | 1/2014 | Chew |
| 2014/0049465 | A1 | 2/2014 | Tremaine et al. |
| 2015/0302539 | A1 | 10/2015 | Mazar et al. |
| 2016/0180044 | A1 | 6/2016 | Delisle et al. |
| 2017/0295395 | A1 | 10/2017 | Smith et al. |

FOREIGN PATENT DOCUMENTS

| | | |
|---|---|---|
| JP | H10-28679 | 2/1998 |
| JP | 2002233512 | 8/2002 |
| JP | 2003220045 | 8/2003 |
| JP | 2003260145 | 9/2003 |
| JP | 2006-512156 | 4/2006 |
| JP | 2006-263329 | 10/2006 |
| WO | 19970000708 | 1/1997 |
| WO | 20060086089 | 8/2006 |
| WO | 20080116822 | 10/2008 |
| WO | 2011011454 | 1/2011 |
| WO | 20120026922 | 3/2012 |

OTHER PUBLICATIONS

Chapin Intellectual Property Law, LLC., Letter sent to Benjamin S. Fernandez, Feagre Baker Daniels, LLP, Denver, CO, no date on letter.

Chu, Yuechun et al., "A Mobile Teletrauma System Using 3G Networks", IEEE Transactions on Information Technology in Biomedicine, Vo. 8, No. 4, Dec. 2004 (7 pages).

Gagliano, "Baltimore, MD . . . Wireless Ambulance Telemedicine May Lessen Stroke Morbidity", Telemedicine Today, 2002, accessed at http://www2.telemedtoday.com/articles/wirelessambulance.shtml, accessed Aug. 30, 2013 (2 pages).

Google search for the term "Transmission of electrocardiograms from a moving ambulance", https://www.google.com/search?q=transmission+of+electrocardiograms+from+a+moving . . . , retrieved Sep. 10, 2013 (85 pages).

Mielinski,et al., (Eds). Mobile Computing, Kluwer Academic Publishers, 2000, 1996 [online] [retrieved on Sep. 12, 2013], retrieved from Google Books at http://books.google.com/books?id=

(56) References Cited

OTHER PUBLICATIONS gx3HVwcE0ZAC&pg=PA624&dq=portable+medical+locaging+a+portable+wireless+communication+network&hl=en&sa=X&ei=5XfAUaXqGsbn0QGMIoHoCw&ved=0CBsQ6AEwAQ#v=onepage&q=portable%20medical20locating%20a%20portable%20wireless%20communication%20network&f=false (1 page).

Jain, A. et al., "Towards a Comprehensive Technology for Recording and Analysis of Multiple Physiological Parameters within their Behavioral and Environmental Context", accessed at http://www.psych-methoden.uni-koeln.de/mitarbeiter/jain/jain-6.htm, accessed Aug. 23, 2013 (12 pages).

Johnson, P. et al., "Remote Physiological Monitoring in the Home", Medical Informatics Europe '96: Human Facets in Information Technology, IOS Press, pp. 63-66, 1996 (4 pages).

Konoske, P.J. et al., "Evaluation of the Mobile Medical Monitor (M3) at Forward Levels of Care", Naval Health Research Center, Technical Document No. 98-2B, Report Date Sep. 1998 (47 pages).

Lee, M.J. et al., "Informatics in Prehospital Care", Trauma Informatics Computers in Health Care 1998, pp. 31-44—Abstract Only (1 page).

Nam, Y.H. et al. "Development of remote diagnosis system integrating digital telemetry for medicine", Engineering in Medicine and Biology Society 1998, Proceedings of the 20th Annual International Conference of the IEEE (vol. 3), Oct. 29-Nov. 1, 1998—Abstract Only (1 page).

Pahlavan, Kaveh et al., "An Overview of Wireless Indoor Geolocation Techniques and Systems", MWCN 2000, LNCS1818, pp. 1-13, 2000 (13 pages).

Pavlopoulos, S. et al., "Ambulance—mobile unit for health care provision via telematics support", Engineering in Medicine and Biology Society, 1996, Bridging Disciplines for Biomedicine, Proceedings of the 18th Annual International Conference of the IEEE (vol. 3), Oct. 31-Nov. 1, 1996—Abstract Only (1 page).

Poor, R., "Standards & Protocols. Wireless Mesh Networks," Ember Corp.; Sensors, Downloaded from http://www.sensorsmag.com/networking-communications/standards-protocols/wireless-mesh-networks-968, Feb. 1, 2003 (5 pages).

Schaldach, M. "Pacemaker Technology", Electrotherapy of the Heart, pp. 47-72, 1992—Abstract Only (1 page).

ScienceDaily, "Telemedicine on Ambulances May Save Stroke Patients", http://www.sciencedaily.com/releases/1998/02/980206071314.htm, Feb. 6, 1998 (3 pages).

Weiss, F.G., "Implications of Silicon Monolithic RCICs for Medical Instrumentation and Telemetry", Silicon Monolithic Integrated Circuits in RF Systems, 1998, Digest of Papers, 1998, Topical Meeting, Sep. 18, 1998—Abstract Only (1 page).

Zoorob, Roger J., et al. "Acute Dyspnea in the Office", American Family Physician, Nov. 1, 2003, pp. 1803-1811 (10 pages).

European Search Report for Application No. 19172265.1, dated Aug. 7, 2019, 9 pages.

* cited by examiner

OVERALL ARCHITECTURE OF INDOOR GEOLOCATION SYSTEM.

DIFFERENTIAL DIAGNOSIS OF ACUTE DYSPNEA IN ADULTS

CARDIAC: CONGESTIVE HEART FAILURE, CORONARY ARTERY DISEASE, ARRHYTHMIA, PERICARDITIS, ACUTE MYOCARDIAL INFARCTION, ANEMIA

PULMONARY: CHRONIC OBSTRUCTIVE PULMONARY DISEASE, ASTHMA, PNEUMONIA, PNEUMOTHORAX, PULMONARY EMBOLISM, PLEURAL EFFUSION, METASTATIC DISEASE, PULMONARY EDEMA, GASTROESOPHAGEAL REFLUX DISEASE WITH ASPIRATION, RESTRICTIVE LUNG DISEASE

PSYCHOGENIC: PANIC ATTACKS, HYPERVENTILATION, PAIN, ANXIETY

UPPER AIRWAY OBSTRUCTION: EPIGLOTTITIS, FOREIGN BODY, CROUP, EPSTEIN-BARR VIRUS

ENDOCRINE: METABOLIC ACIDOSIS, MEDICATIONS

CENTRAL: NEUROMUSCULAR DISORDERS, PAIN, ASPIRIN OVERDOSE

PEDIATRIC: BRONCHIOLITIS, CROUP, EPIGLOTTITIS, FOREIGN BODY ASPIRATION, MYOCARDITIS

FIG. 26

CLUES TO THE DIAGNOSIS OF DYSPNEA

| SYMPTOMS OR FEATURES IN THE HISTORY | POSSIBLE DIAGNOSIS |
| --- | --- |
| COUGH | ASTHMA, PNEUMONIA |
| SEVERE SORE THROAT | EPIGLOTTITIS |
| PLEURITIC CHEST PAIN | PERICARDITIS, PULMONARY EMBOLISM, PNEUMOTHORAX, PNEUMONIA |
| ORTHOPNEA, NOCTURNAL PAROXYSMAL DYSPNEA, EDEMA | CONGESTIVE HEART FAILURE |
| TOBACCO USE | CHRONIC OBSTRUCTIVE PULMONARY DISEASE, CONGESTIVE HEART FAILURE, PULMONARY EMBOLISM |
| INDIGESTION, DYSPHAGIA | GASTROESOPHAGEAL REFLUX DISEASE, ASPIRATION |
| BARKING COUGH | CROUP |

FIG. 27

PHYSICAL EXAMINATION FINDINGS IN THE DIAGNOSIS OF ACUTE DYSPNEA

| FINDINGS | POSSIBLE DIAGNOSIS |
| --- | --- |
| WHEEZING, PULSUS PARADOXUS, ACCESSORY MUSCLE USE | ACUTE ASTHMA, COPD EXACERBATION |
| WHEEZING, CLUBBING, BARREL CHEST, DECREASED BREATH SOUNDS | COPD EXACERBATION |
| FEVER, CRACKLES, INCREASED FREMITUS | PNEUMONIA |
| EDEMA, NECK VEIN DISTENSION, $S_3$ OR $S_4$ HEPATOJUGULAR REFLUX, MURMERS, RALES, HYPERTENSION, WHEEZING | CONGESTIVE HEART FAILURE, PULMONARY EDEMA |
| WHEEZING, FRICTION RUB, LOWER EXTREMITY SWELLING | PULMONARY EMBOLISM |
| ABSENT BREATH SOUNDS, HYPERRESONANCE | PNEUMOTHORAX |
| INSPIRATORY STRIDOR, RHONCHI, RETRACTIONS | CROUP |
| STRIDOR, DROOLING, FEVER | EPIGLOTTITIS |
| STRIDOR, WHEEZING, PERSISTENT PNEUMONIA | FOREIGN BODY ASPIRATION |
| WHEEZING, FLARING, INTERCOSTAL RETRACTIONS, APNEA | BRONCHIOLITIS |
| SIGHING | HYPERVENTILATION |

COPD = CHRONIC OBSTRUCTIVE PULMONARY DISEASE

FIG. 28

SHORTNESS OF BREATH ADULT
ASTHMA - COPD - ACUTE DECOMPENSATED HEART FAILURE (CHF)

SYSTEMS AND METHODS FOR EMS DEVICE COMMUNICATIONS INTERFACE

CROSS-REFERENCE TO RELATED APPLICATIONS

This application is a continuation under 35 U.S.C. § 120 of U.S. patent application Ser. No. 16/702,868, filed Dec. 4, 2019, which is a continuation of U.S. patent application Ser. No. 13/647,744, filed Oct. 9, 2012, and issued as U.S. Pat. No. 10,765,873 on Sep. 8, 2020, which is a continuation of Patent Cooperation Treaty Application No. PCT/US2011/031868, filed on Apr. 9, 2011, which claims the benefit of U.S. Provisional Application No. 61/322,675, filed Apr. 9, 2010, and of U.S. Provisional Application No. 61/434,812, filed Jan. 20, 2011, and this application is a continuation under 35 U.S.C. §120 of U.S. patent application Ser. No. 15/959,404, filed Apr. 23, 2018, and issued as U.S. Pat. No. 11,109,816 on Sep. 7, 2021, which is a continuation of U.S. patent application Ser. No. 12/840,129 filed on Jul. 20, 2010, which claims the benefit of U.S. Provisional Application No. 61/322,675, filed Apr. 9, 2010, and of U.S. Provisional Application No. 61/227,187, filed Jul. 21, 2009. All subject matter set forth in the above referenced applications is hereby incorporated by reference in its entirety into the present application as if fully set forth herein.

TECHNICAL FIELD

Embodiments of the present invention relate generally to emergency medical services information management, and more particularly to collection, organization, and communication of information gathered from a device used in emergency medical services.

BACKGROUND

Devices that are used to gather patient monitoring information in emergency medical services ("EMS") applications, for example defibrillator devices, are often complex and expensive devices, primarily because they serve a very important purpose in an EMS setting, and must be durable, accurate, and reliable. The communications capabilities of such devices are often limited by their hardware, such that users must choose between buying a new defibrillator or continuing to use the same, often slower, communications interfaces available with an older defibrillator. A retrofit solution that involves changing the existing hardware or software of the device may be almost as costly and time-consuming to implement as device replacement itself.

Existing patient monitoring devices store various kinds of information during use. Users wishing to upload or download such information, typically after an incident or after a certain period of time (e.g. at the end of the day or end of the week), are often limited to retrieving only the entire content of the device's memory card, regardless of whether the user is interested in only a specific subset of the entire card's contents. This increases the time necessary for data transfer, as well as the time necessary to sort the data and/or identify the desired subset of the data.

SUMMARY

A system for supplementing communications capabilities of a patient monitoring device configured to monitor a patient and to make available patient monitoring information according to an embodiment of the present invention includes an interface device configured to communicably couple with and to receive the patient monitoring information from the patient monitoring device, a memory device hosted by the interface device and configured to store at least a portion of the patient monitoring information, a wireless transceiver hosted by the interface device, an asset management database hosted by the interface device, and a processor communicably coupled to the wireless transceiver and the asset management database, the processor configured to format the patient monitoring information into one or more data objects, each of the one or more data objects associated with an EMS incident during which the patient monitoring information was gathered, the processor further configured to store the one or more data objects to the asset management database and to transmit the one or more data objects with the wireless transceiver.

The system as described above, wherein the processor is further configured to receive, via the wireless transceiver, a request for data objects associated with a specific EMS incident, query the asset management database to retrieve all data objects associated with the specific EMS incident, and to transmit the data objects associated with the specific EMS incident with the wireless transceiver.

The system as described above, wherein the patient monitoring device is a defibrillator, and wherein the one or more data objects comprises one or more ECG waveforms. The one or more data objects may also comprise patient waveforms, which may include up to eight ECG waveforms, invasive blood pressure waveforms, SpO2 waveforms, EtCO2 waveforms, CPR waveforms, and/or impedance respiration waveforms. A number of parameters may represent patient Vital information, such as for example heart rate, NIBP measurements, temperature measurements, and others.

The system as described above, wherein the patient monitoring device comprises an audio device configured to generate a heart sound signal from a patient, and wherein the processor is further configured to format the heart sound signal into the one or more heart sound data objects.

The system as described above, further comprising an electronic stethoscope configured to connect with the processor and receive the one or more heart sound data objects.

A method for streaming patient information from a clinical device according to embodiments of the present invention includes establishing a wireless data connection with the clinical device, receiving patient information from the clinical device via the wireless data connection at least once every five seconds, displaying at least a portion of the patient information in an emergency medical services mobile environment.

The method as described above, wherein the clinical device is a defibrillator.

The method as described above, wherein receiving the patient information comprises receiving the patient information from the clinical device via the wireless data connection at least once every second.

The method as described above, wherein the wireless data connection is a secure WiFi connection.

The method as described above, wherein the patient information is clinical information, the method further comprising receiving non-clinical information and displaying the clinical information and the non-clinical information simultaneously in the emergency medical services mobile environment.

The method as described above, wherein the patient information comprises an ECG waveform.

The method as described above, wherein the patient information comprises a heart rate.

The method as described above, wherein the patient information comprises an ECG waveform.

The method as described above, further including receiving full disclosure data from the clinical device, formatting the full disclosure data into one or more data elements, wherein the one or more data elements comprise a full disclosure record XML object, wherein the full disclosure record XML object, and/or each element within the full disclosure XML object, comprises a time identifier, an incident identifier, and clinical information associated with a time identified by the time identifier and an incident identified by the incident identifier, and sending the full disclosure record XML object over the wireless data connection as the patient information.

The method as described above, further comprising storing the one or more data objects in a computer readable medium.

The as described above, further including sending a request over the wireless data connection, the request including a particular incident identifier, retrieving from the computer readable medium and adding to a response set each of the one or more data objects for which the incident identifier corresponds to the particular incident identifier of the request, and sending the response set over the wireless data connection.

The method as described above, further comprising displaying at least a portion of the response set in the emergency medical services mobile environment.

A method for supplementing communications capabilities of a patient monitoring device configured to monitor a patient and to make available patient monitoring information according to an embodiment of the present invention includes receiving the patient monitoring information from the patient monitoring device to an EMS communication interface device, storing the patient monitoring information to a memory hosted by the EMS communication interface device, formatting the patient monitoring information into a stream of one or more data objects, each of the one or more data objects associated with an EMS incident during which the patient monitoring information was gathered, storing the one or more data objects to a database, or an asset management database, hosted by the EMS communication interface device, and transmitting the stream of one or more data objects via a wireless transceiver of the EMS communication interface device.

A method according to an embodiment of the present invention includes transmitting clinical data about a patient from a defibrillator device to an external device via a wireless network connection while the defibrillator device is actively monitoring the patient during an emergency medical treatment or transport.

The method as described above, wherein the clinical data comprises a plurality of ECG waveforms, the method further comprising displaying one or more historical snapshots of the plurality of ECG waveforms on a display device, wherein the display device is independent of the defibrillator device.

The method as described above, wherein displaying the one or more historical snapshots of the plurality of ECG waveforms comprises displaying a most recent ECG waveform of the plurality of ECG waveforms simultaneously with another of the one or more historical snapshots of the plurality of ECG waveforms.

The method as described above, wherein the external device is a display device located within an emergency response vehicle.

The method as described above, wherein the emergency response vehicle is an ambulance.

The method as described above, further comprising transmitting the clinical data to a remote server (e.g. an enterprise server) to enable web browser access to the clinical data while the defibrillator device is actively monitoring the patient during the emergency medical treatment or transport.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 26 illustrates an example explanation of differential diagnosis of acute dyspnea in adults.

FIG. 27 illustrates an example explanation of clues to differential diagnosis of dyspnea.

FIG. 28 illustrates an example listing of physical exam findings in the diagnosis of acute dyspnea.

Figure 1:
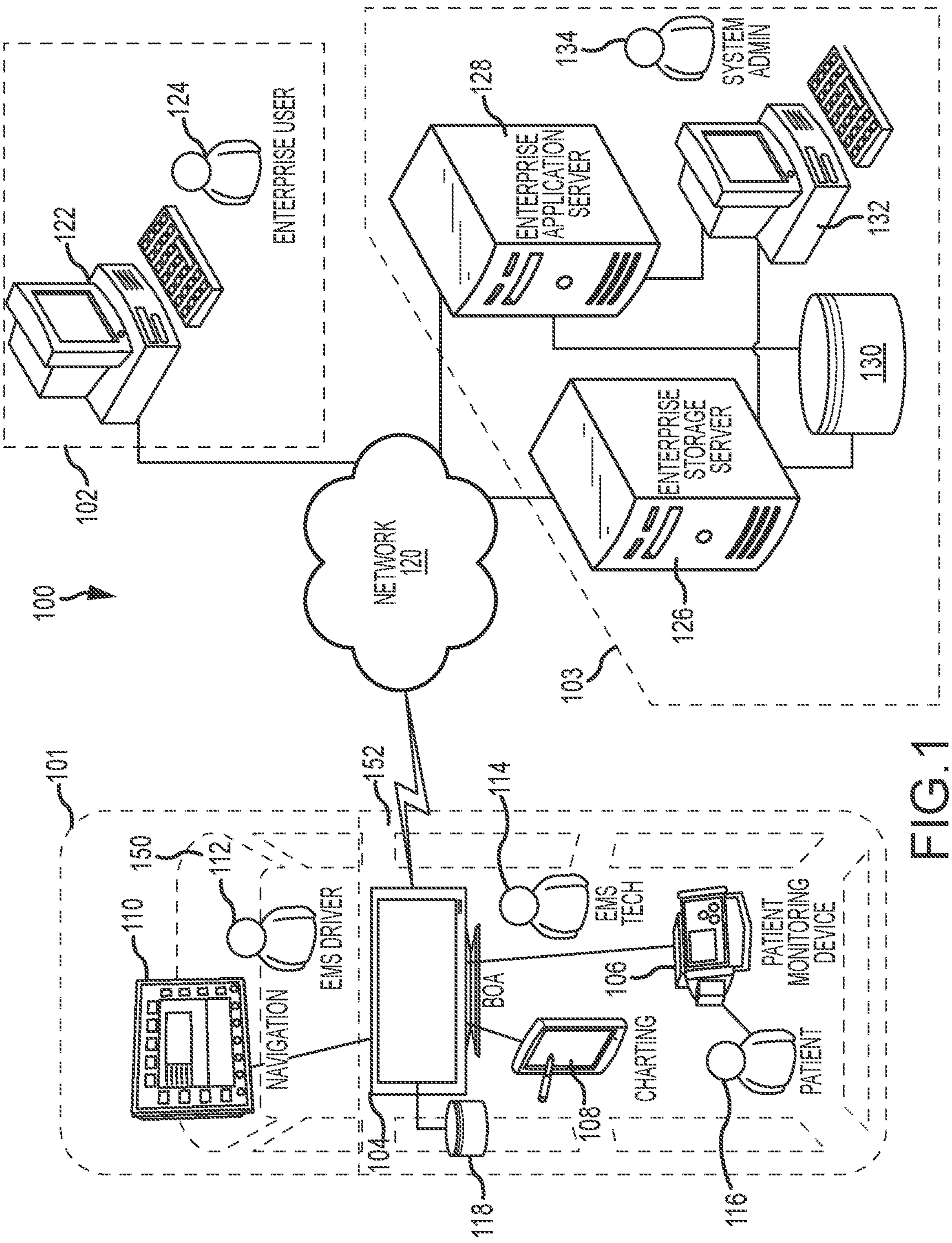
FIG. 1 illustrates a system for mobile and enterprise user real-time display of medical information collected from multiple different EMS devices, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

As illustrated in FIG. 1, a system 100 according to embodiments of the present invention performs advanced data management, integration and presentation of EMS data from multiple different devices. System 100 includes a mobile environment 101, an enterprise environment 102, and an administration environment 103. Devices within the various environments 101, 102, 103 may be communicably coupled via a network 120, such as, for example, the Internet.

As used herein, the phrase "communicably coupled" is used in its broadest sense to refer to any coupling whereby information may be passed. Thus, for example, communicably coupled includes electrically coupled by, for example, a wire; optically coupled by, for example, an optical cable; and/or wirelessly coupled by, for example, a radio frequency or other transmission media. "Communicably coupled" also includes, for example, indirect coupling, such as through a network, or direct coupling.

Figure 24:
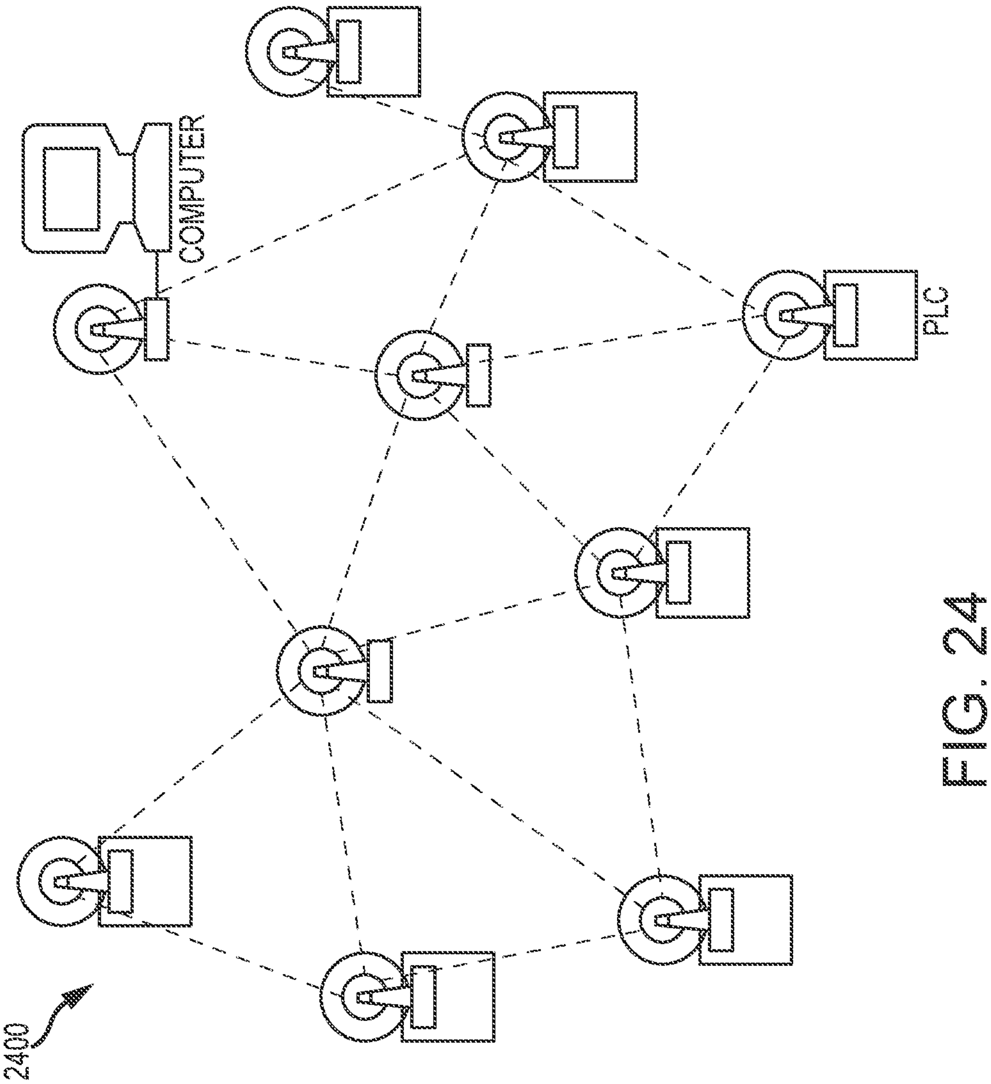
FIG. 24 illustrates a conventional mesh network.

The network 120 may also take the form of an ad hoc, self-configuring, self-healing network 2400 such as a MESH network, as illustrated in FIG. 24, according to embodiments of the present invention. FIG. 24, as well as the following information about MESH networks in paragraphs [00109] to [00117], is taken directly from Poor, Robert; WIRELESS MESH NETWORKS; Sensors (Feb. 1, 2003), available at http://www.sensorsmag.com/networking-communications/standards-protocols/wireless-mesh-networks-968, which is incorporated herein by reference. Wireless systems for industry conventionally use cellular phone-style radio links, using point-to-point or point-to-multipoint transmission. But research at MIT's Media Lab in Cambridge, Mass., indicated that traditional wireless formats have limitations in industrial applications. These include rigid structure, meticulous planning requirements, and dropped signals. This can pose an acute challenge in an EMS or mass casualty environment in which existing infrastructure may be either sparse (e.g. a rural environment) or dysfunctional (e.g. a mass casualty or disaster situation).

In contrast, wireless mesh networks 2400 are multihop systems in which devices assist each other in transmitting packets through the network, especially in adverse conditions. Such ad hoc networks may be implemented with minimal preparation, and they provide a reliable, flexible system that can be extended to thousands of devices, according to embodiments of the present invention.

The wireless mesh network topology developed at MIT for industrial control and sensing is a point-to-point-to-point, or peer-to-peer, system called an ad hoc, multihop network. A node can send and receive messages, and in a mesh network, a node also functions as a router and can relay messages for its neighbors. Through the relaying process, a packet of wireless data will find its way to its destination, passing through intermediate nodes with reliable communication links, as illustrated in FIG. 24.

In a wireless mesh network 2400, multiple nodes cooperate to relay a message to its destination. The mesh topology enhances the overall reliability of the network, which is particularly important when operating in harsh industrial environments. Like the Internet and other peer-to-peer router-based networks, a mesh network offers multiple redundant communications paths throughout the network. If one link fails for any reason (including the introduction of strong RF interference), the network automatically routes messages through alternate paths. In a mesh network 2400, the distance between nodes can be shortened, which dramatically increases the link quality. Reducing the distance by a factor of two, the resulting signal is at least four times more powerful at the receiver. This makes links more reliable without increasing transmitter power in individual nodes. The reach of a mesh network may be extended, redundancy added, and general reliability improved simply by adding more notes.

Network 2400 may be a self-configuring and self-healing network, according to embodiments of the present invention. According to embodiments of the present invention, a network 2400 does not require a system administrator to tell it how to get a message to its destination. A mesh network 2400 is self-organizing and does not require manual configuration. Because of this, adding new gear or relocating existing gear is as simple as plugging it in and turning it on, according to embodiments of the present invention. The network discovers the new node and automatically incorporates it into the existing system, according to embodiments of the present invention.

A mesh network 2400 is not only inherently reliable, it is also highly adaptable, according to embodiments of the present invention. For example, if a tank-level sensor and data logger are placed too far apart for a robust RF communications link, one or more repeater nodes may be added to fill the gaps in the network 2400.

On the Internet, if one router goes down, messages are sent through an alternate path by other routers. Similarly, if a device or its link in a mesh network fails, messages are sent around it via other devices. Loss of one or more nodes does not necessarily affect the network's operation. A mesh network is self-healing because human intervention is not necessary for re-routing of messages. Such networks 2400 provide redundancy and scalability, according to embodiments of the present invention.

In a mesh network, the degree of redundancy is essentially a function of node density. A network can be deliberately over-designed for reliability simply by adding extra nodes, so each device has two or more paths for sending data. This is a simpler way of obtaining redundancy than is possible in most other types of systems. A mesh network is also scalable and can handle hundreds or thousands of nodes. Because the operation of network 2400 does not depend on a central control point, adding multiple data collection points or gateways may be convenient.

Reliability, adaptability, and scalability are notable attributes of a wireless network for industrial control and sensing applications, according to embodiments of the present invention. Point-to-point networks provide reliability, but they are often challenging to scale to handle more than one pair of end points. Point-to-multipoint networks can handle more end points, but their reliability may depend on placement of the access point and end points. Mesh networks are inherently reliable, adapt easily to environmental or architectural constraints, and can scale to handle thousands of end points.

According to embodiments of the present invention, the mobile environment 101 is an ambulance or other EMS vehicle—for example a vehicular mobile environment (VME). The mobile environment may also be the local network of data entry devices as well as diagnostic and therapeutic devices established at time of treatment of a patient or patients in the field environment—the "At Scene Patient Mobile Environment" (ASPME). The mobile environment may also be a combination of one or more of VMEs and/or ASPMEs. The mobile environment may include a navigation device 110 used by the driver 112 to track the mobile environment's position 101, locate the mobile environment 101 and/or the emergency location, and locate the transport destination, according to embodiments of the present invention. The navigation device 110 may include a Global Positioning System ("GPS"), for example. The navigation device 110 may also be configured to perform calculations about vehicle speed, the travel time between locations, and estimated times of arrival. According to embodiments of the present invention, the navigation device 110 is located at the front of the ambulance to assist the driver 112 in navigating the vehicle. The navigation device 110 may be, for example, a RescueNet® Navigator onboard electronic data communication system available from Zoll Data Systems of Broomfield, Colo.

Figure 25:
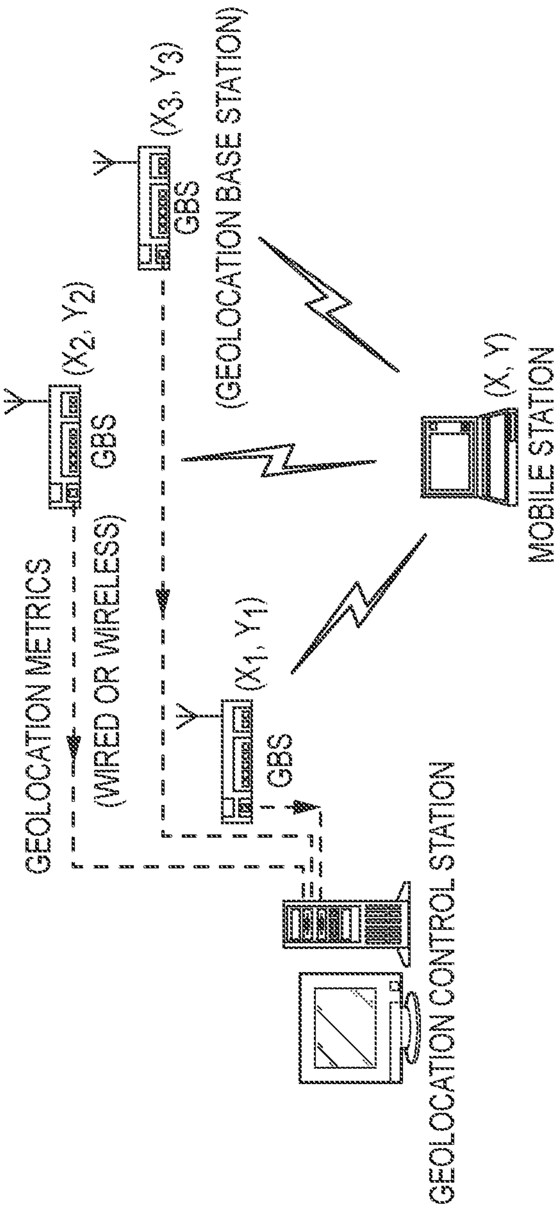
FIG. 25 illustrates an indoor geolocation system.
Figure 29A:
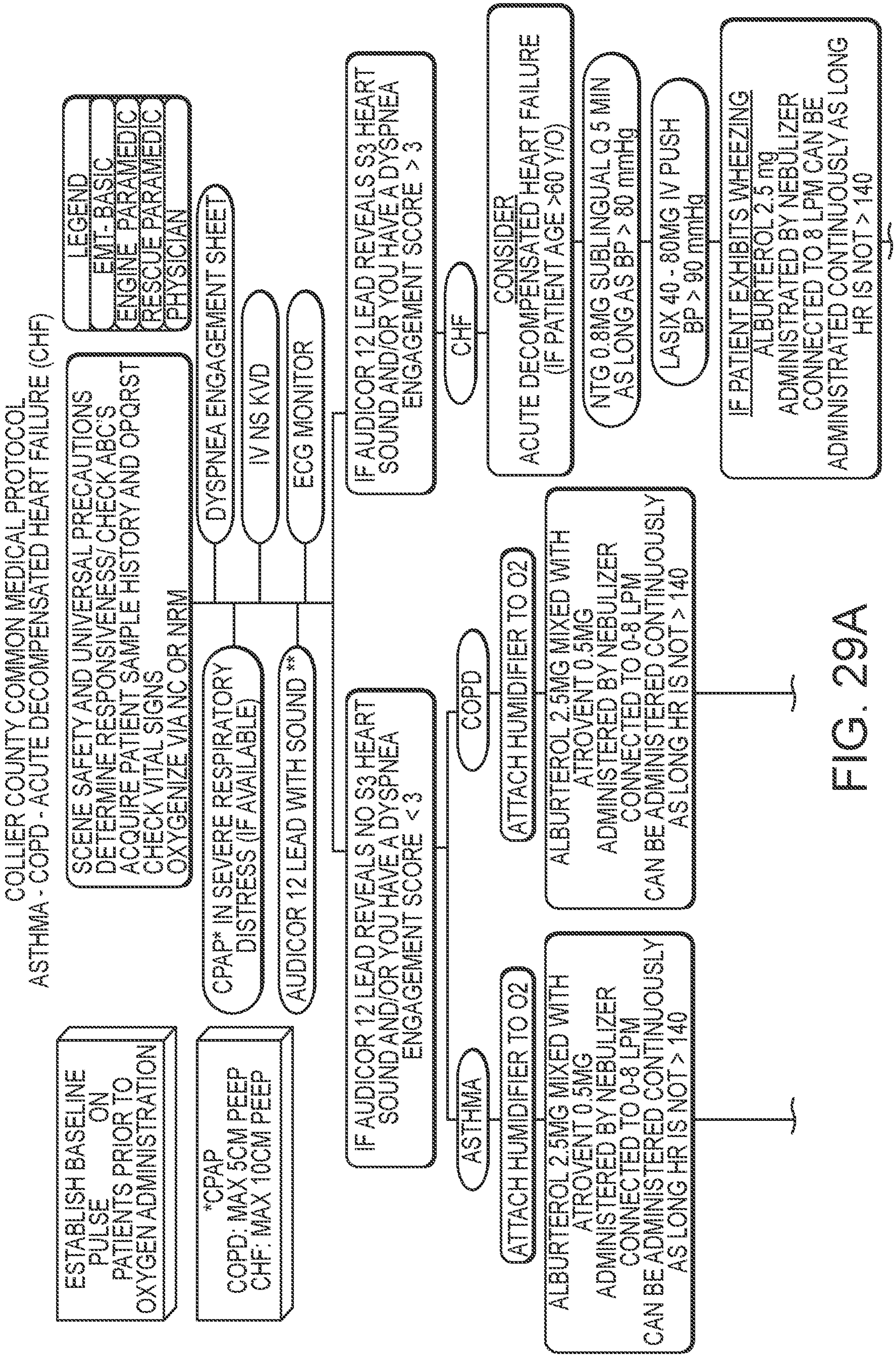
FIGS. 29A and 29B show an example treatment protocol for asthma, COPD, and acute decompensated heart failure.
Figure 29B:
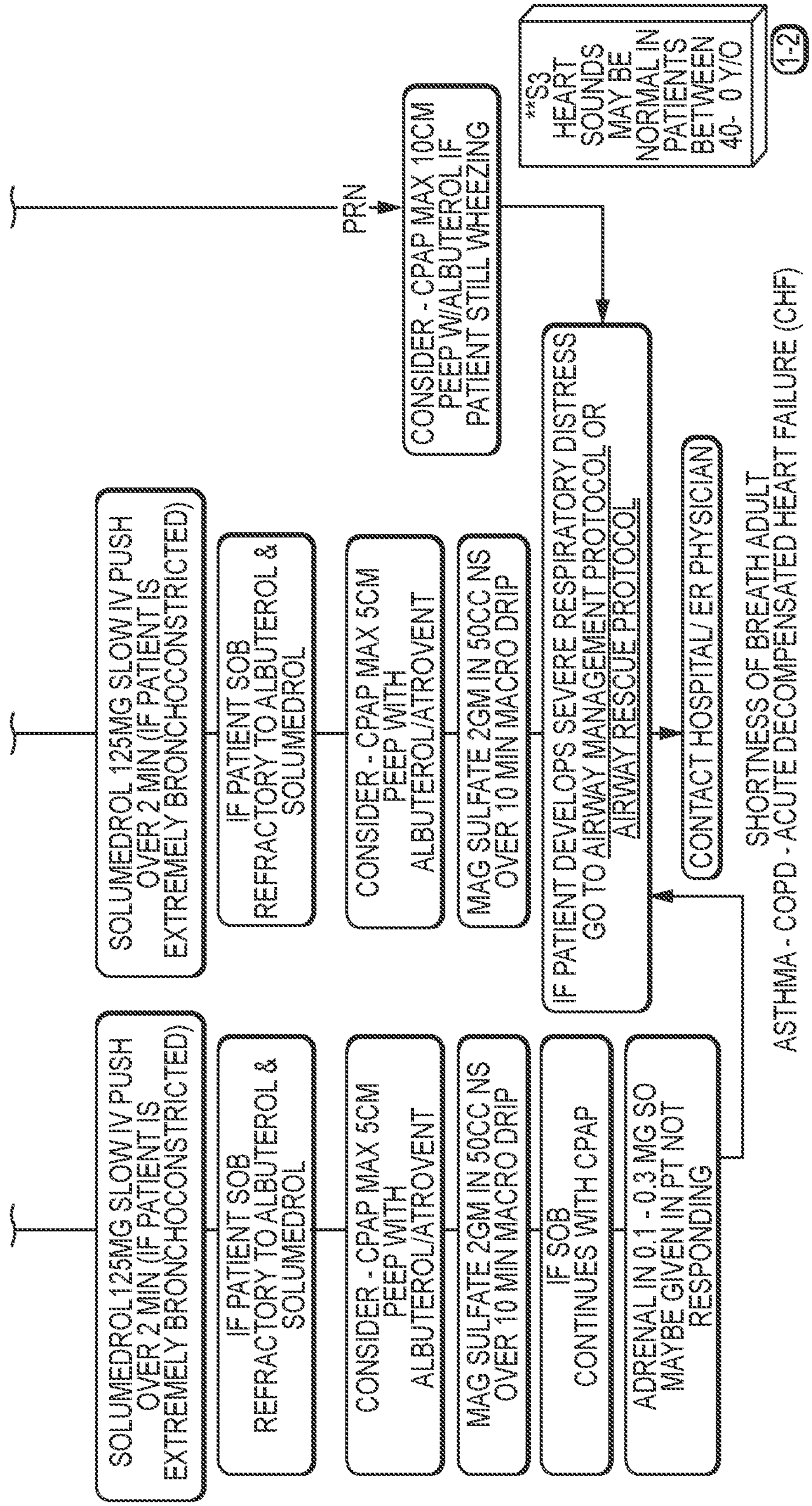

FIG. 25, as well as the following information about geolocation in paragraphs [00119] through [00120], is taken directly from K. Pahlavan, et al., "An Overview of Wireless Indoor Geolocation," Mobile and Wireless Communications Networks IFIP-TC6/European Commission NETWORKING 2000 International Workshop, MWCN 2000 Paris, France, May 16-17, 2000, which is incorporated herein by reference. More generally, the mobile environment may include a geolocation sensor in one or more of the devices in the VME or ASPME. The geolocation sensor may be of a common type such as, for example, a Global Positioning System (GPS). GPS, though, may be subject to certain limitations: 1) line of sight to more than one GPS satellite, which may limit its performance in indoor environments; 2) in some urban environments, location accuracy is reduced due to signal reflections off of buildings; and 3) normal accuracy may be insufficient in the case of a mass casualty in which accuracies of better than +/−5 feet may be required when there are multiple casualties and the locations of each victim needs to be integrated into a software mapping environment, according to embodiments of the present invention.

Therefore, additional locator base stations may be deployed on-scene outdoors, or within buildings, that may augment or replace the conventional GPS-based geolocator systems, according to embodiments of the present invention. Similar to the cellular geolocation system, the architecture of indoor geolocation systems may fall within one of two main categories: mobile-based architecture and network-based architecture. Most conventional indoor geolocation applications have been focused on network-based system architecture as shown in FIG. 25. The geolocation base stations (GBS) extract location metrics from the radio signals transmitted by the mobile station and relay the information to a geolocation control station (GCS). The connection between GBS and GCS can be either wired or wireless, according to embodiments of the present invention. Then the position of the mobile station may be estimated, in an indoor environment. As a result, dedicated indoor geolocation systems provide accurate indoor geolocation services. This may be applied as well to a mobile environment such as a battlefield or other mass casualty situation in which base stations with better known accuracy based on landmarks or more sophisticated GPS systems such as differential GPS (DGPS) can be deployed to provide highly accurate and complete information about the patient status integrated into the navigation software or other mapping software, such as, for example, Google maps.

As illustrated in FIG. 1, a patient monitoring device 106 and a patient charting device 108 are also often used for patient care in the mobile environment 101, according to embodiments of the present invention. The EMS technician 114 attaches the patient monitoring device 106 to the patient 116 to monitor the patient 116. The patient monitoring device 106 may be, for example, a defibrillator device with electrodes and/or sensors configured for attachment to the patient 116 to monitor heart rate and/or to generate electrocardiographs ("ECG's"), according to embodiments of the present invention. The patient monitoring device 106 may also include sensors to detect or a processor to derive or calculate other patient conditions. For example, the patient monitoring device 106 may monitor, detect, treat and/or derive or calculate blood pressure, temperature, respiration rate, blood oxygen level, end-tidal carbon dioxide level, pulmonary function, blood glucose level, and/or weight, according to embodiments of the present invention. The patient monitoring device 106 may be a Zoll E-Series® defibrillator available from Zoll Medical Corporation of Chelmsford, Mass., according to embodiments of the present invention. A patient monitoring device may also be a patient treatment device, or another kind of device that includes patient monitoring and/or patient treatment capabilities, according to embodiments of the present invention.

The patient charting device 108 is a device used by the EMS technician 114 to generate records and/or notes about the patient's 116 condition and/or treatments applied to the patient, according to embodiments of the present invention. For example, the patient charting device 108 may be used to note a dosage of medicine given to the patient 116 at a particular time. The patient charting device 108 and/or patient monitoring device 106 may have a clock, which may be synchronized with an external time source such as a network or a satellite to prevent the EMS technician from having to manually enter a time of treatment or observation (or having to attempt to estimate the time of treatment for charting purposes long after the treatment was administered), according to embodiments of the present invention. The patient charting device 108 may also be used to record biographic and/or demographic and/or historical information about a patient, for example the patient's name, identification number, height, weight, and/or medical history, according to embodiments of the present invention. According to embodiments of the present invention, the patient charting device 108 is a tablet PC, such as for example the TabletPCR component of the RescueNet® ePCR Suite available from Zoll Data Systems of Broomfield, Colo. According to some embodiments of the present invention, the patient charting device 108 is a wristband or smartphone such as an Apple iPhone or iPad with interactive data entry interface such as a touch screen or voice recognition data entry that may be communicably connected to the BOA device 104 and tapped to indicate what was done with the patient 116 and when it was done.

The navigation device 110, the charting device 108, and the monitoring device 106 are each separately very useful to the EMS drivers 112 and technicians 114 before, during, and after the patient transport. A "back of ambulance" ("BOA") device 104 receives, organizes, stores, and displays data from each device 108, 110, 112 to further enhance the usefulness of each device 108, 110, 112 and to make it much easier for the EMS technician 114 to perform certain tasks that would normally require the EMS technician 114 to divert visual and manual attention to each device 108, 110, 112 separately, according to embodiments of the present invention. In other words, the BOA device centralizes and organizes information that would normally be de-centralized and disorganized, according to embodiments of the present invention.

Although device 104 is referred to herein as a "back of ambulance" device because the EMS technician 114 would normally benefit the most from having such a display device mounted in the back 152 of an ambulance, one of ordinary skill in the art, based on the disclosure provided herein, will recognize that some or all of the BOA device 104 may be located in any part of a mobile environment 101, EMS vehicle, and/or anywhere else useful to an EMS technician 114. For example, the BOA device 104 may be located in the front 150 of an ambulance, and/or may include components that are portable and can be carried into a patient residence, according to embodiments of the present invention.

The BOA device 104 is communicably coupled to the patient monitoring device 106, the patient charting device 108, and the navigation device 110, according to embodiments of the present invention. The BOA device 104 is also communicably coupled to a storage medium 118. The BOA device 104 may be a touch-screen, flat panel PC, and the storage medium 118 may be located within or external to the BOA device 104, according to embodiments of the present invention. The BOA device 104 may include a display template serving as a graphical user interface, which permits the user (e.g. EMS tech 114) to select different subsets and/or display modes of the information gathered from and/or sent to devices 106, 108, 110, according to embodiments of the present invention.

Figure 2:
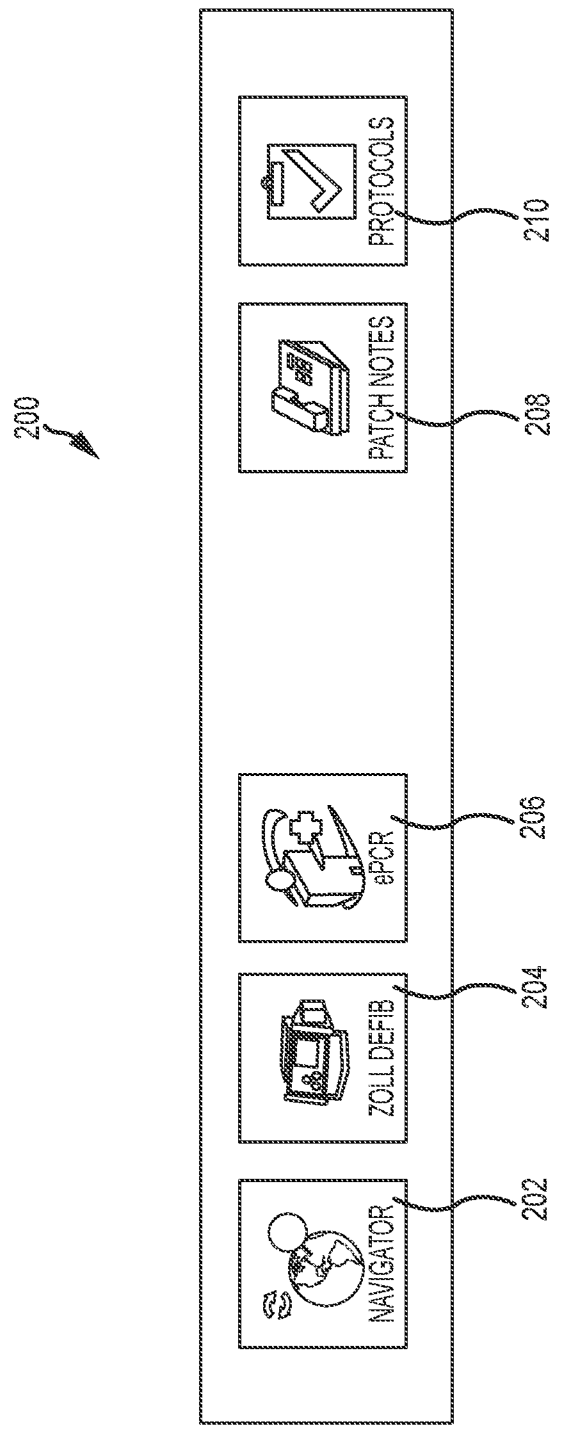
FIG. 2 illustrates one example of a menu template for the display of a "back of ambulance" ("BOA") device, according to embodiments of the present invention.

FIG. 2 illustrates one example of a menu template 200 for the display of BOA device 104, according to embodiments of the present invention. The menu template 200 includes a navigation button 202, a patient monitoring device button 204, a patient charting device button 206, a "patch notes" button 208, and a protocols button 210, according to embodiments of the present invention. Pressing one of the buttons takes the user (e.g. EMS tech 114) to a particular page displaying all or a subset of information from devices 106, 108, 110. FIGS. 3-7 illustrate examples of particular information templates according to which information from the one or more EMS devices 106, 108, 110 is displayed, according to embodiments of the present invention. Based on the disclosure provided herein, one of ordinary skill in the art will recognize various other information templates according to which such information may be displayed.

Figure 3:
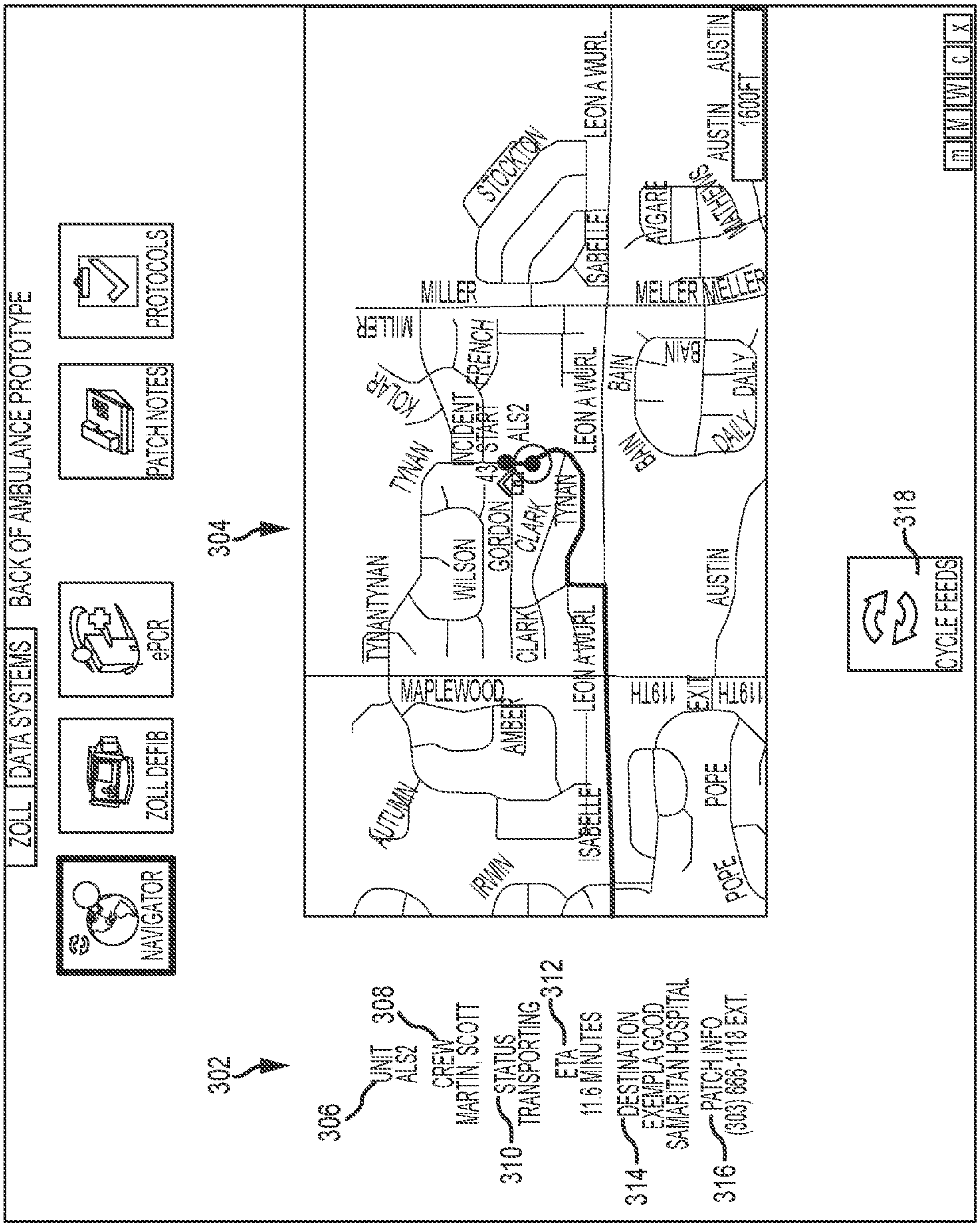
FIG. 3 illustrates a display and graphical user interface displayed when the user selects the navigation button of the menu template, according to embodiments of the present invention.

FIG. 3 illustrates a graphical user interface displayed when the user selects the navigation button 202, according to embodiments of the present invention. One part of the display includes a status section 302 and another part of the display includes a map section 304, according to embodiments of the present invention. The status section 302 includes one or more fields identifying information about the EMS vehicle trip, according to embodiments of the present invention. For example, the fields of the status section 302 may include one or more of a Unit field 306 identifying the name of the EMS vehicle for which information is displayed, a Crew unit 308 identifying one or more crew members of the EMS vehicle, a Status unit 310 identifying the status of the trip (e.g. "transporting" or "en route to patient"), an ETA field 312 identifying an estimated time of arrival at the destination, a Destination field 314 identifying the destination of the EMS vehicle (e.g. the hospital), and a Patch Info field 316 identifying a phone number or other information for contacting the EMS vehicle destination (e.g. the hospital), according to embodiments of the present invention.

The map section 304 may display street information along with the origin, destination, route identification, and/or progress information, according to embodiments of the present invention. The navigation device 110 may also supply vehicle status information for display, which may also be useful when a transport has not yet begun. A user may select a Cycle Feeds button 318 in order to continuously transition the display between one or more of the various displays of FIGS. 3-7, according to embodiments of the present invention. The information illustrated in FIG. 3 would normally be available only to the driver 112 in the front of the ambulance 101, but because BOA device 104 is communicably coupled to the navigation device 110, the BOA device 104 can display all or a selected subset of the information available to the navigation device 110.

Figure 4:
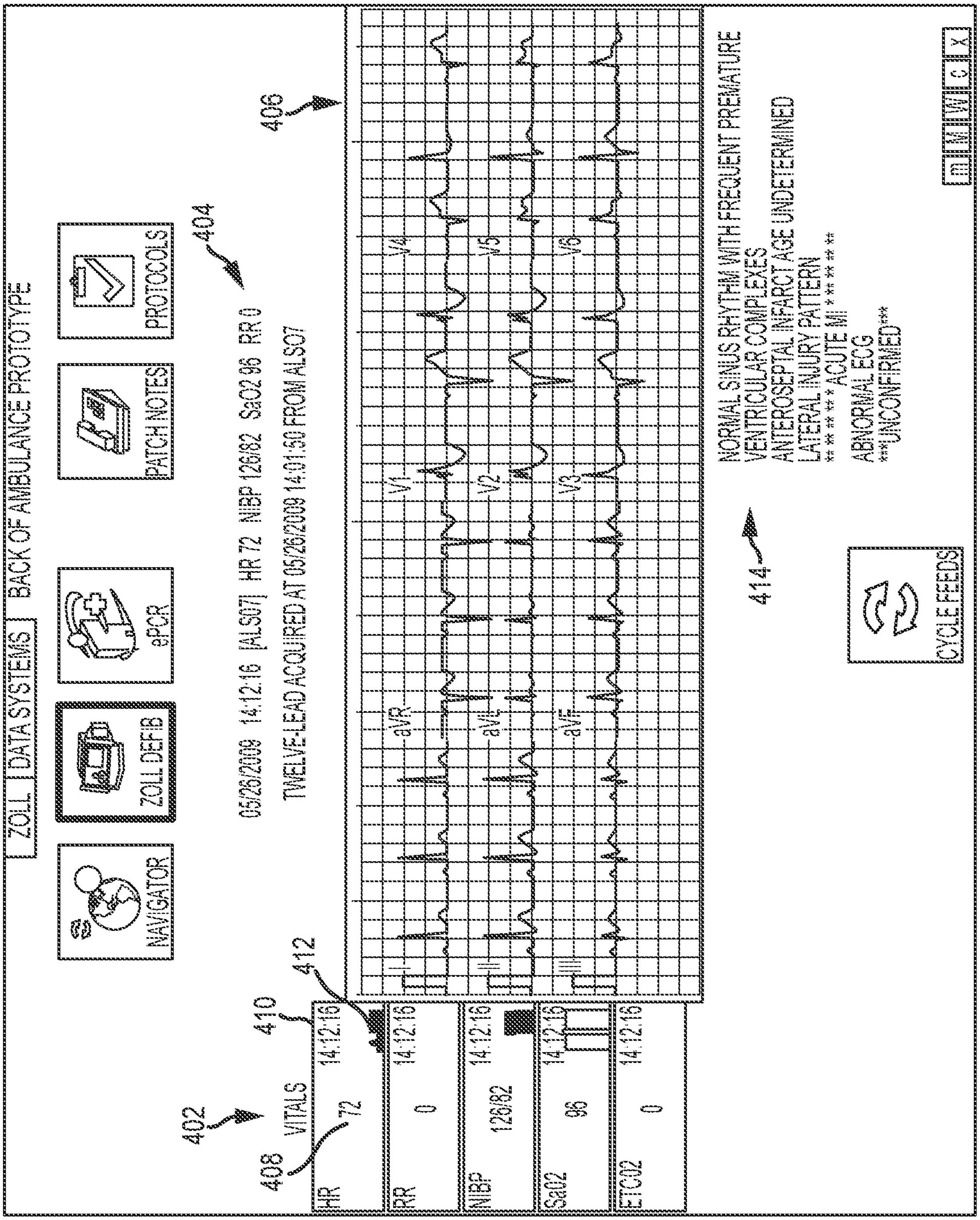
FIG. 4 illustrates a display and graphical user interface displayed when the user selects the patient monitoring button of the menu template, according to embodiments of the present invention.

FIG. 4 illustrates a graphical user interface displayed when the user selects the patient monitoring button 204 of the menu template, according to embodiments of the present invention. FIG. 4 displays information received by the BOA device 104 from a patient monitoring device 106 that is a Zoll E-Series® defibrillator. The display includes a vertical vital signs section 402, a horizontal vital signs summary section 404, a graphical section 406, and interpretation section 414, according to embodiments of the present invention. The vertical vital signs section 402 includes one or more fields indicating a condition of the patient 116 to which the device 106 is attached. For example, the vital signs section 402 includes a heart rate field, a respiration rate field, a blood pressure field, a blood oxygen level field, and an end-tidal carbon dioxide level field. Each field may include a visual indication of a further subset of information. For example, the heart rate field may include a numerical indication 408 of the heart rate, a time indication 410 reflecting the time that the measurement was taken or derived, and a historical graph 412 indicating generally how the heart rate has increased or decreased since the first measurement or a predetermined time, according to embodiments of the present invention. Other fields may include similar indicators, according to embodiments of the present invention. Vital sign trending may also be displayed.

A horizontal vital signs summary section 404 indicates, for example, the numerical values represented simultaneously in the vertical vital signs section 402, according to embodiments of the present invention. The graphical section 406 includes a visual representation of an electrocardiograph, such as that acquired from a twelve-lead sensor placement on the patient 116, according to embodiments of the present invention. Just above the ECG is an indication of when the ECG was acquired. As new vital signs information and/or new ECG information becomes available, the display of FIG. 4 is automatically refreshed to show the most recent data from the patient monitoring device 106, according to embodiments of the present invention. The interpretation section 414 includes automatically-generated information from the device 106, for example, indicating potential causes of the symptoms observed by the device 106, according to embodiments of the present invention.

Figure 5:
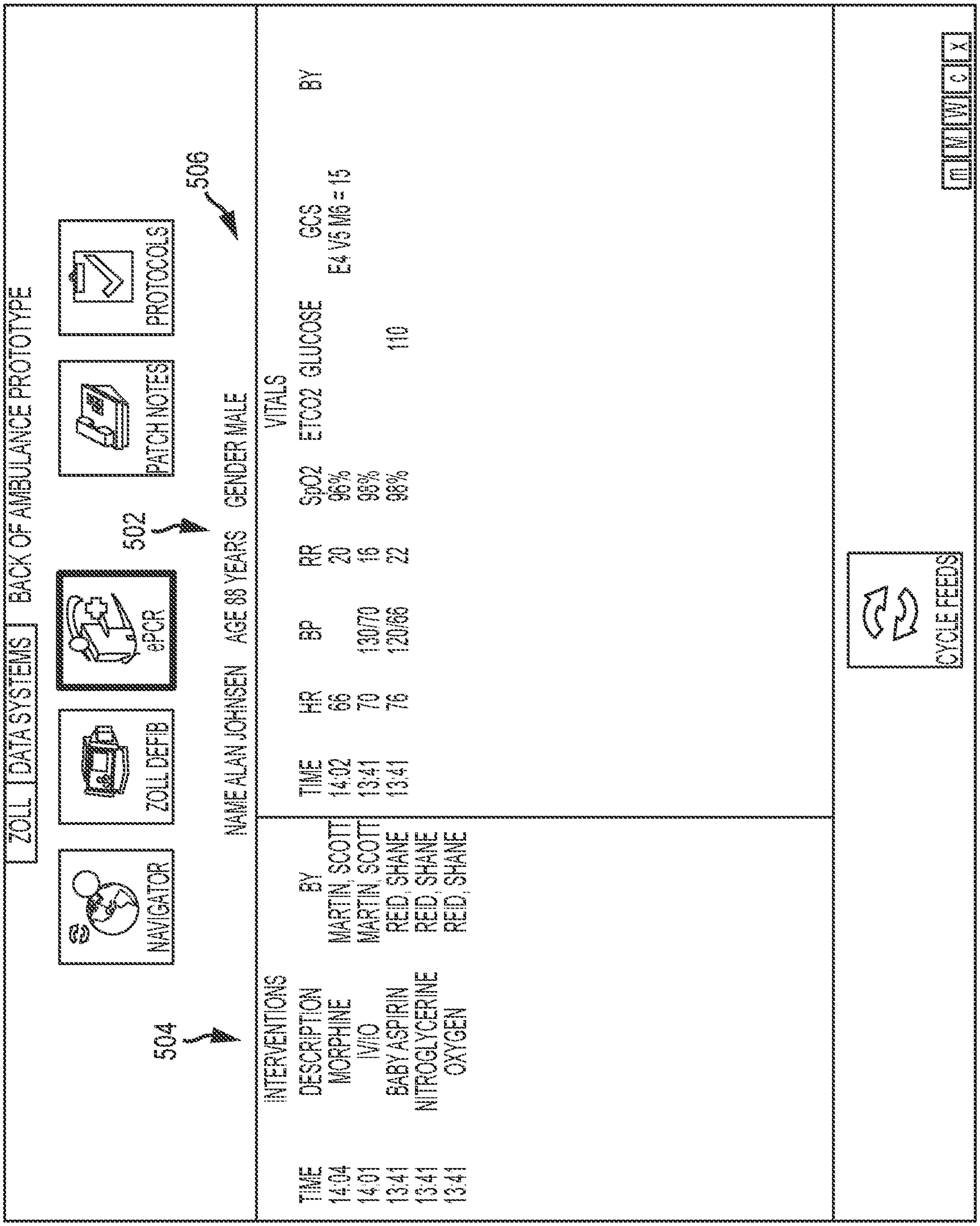
FIG. 5 illustrates a display and graphical user interface displayed when the user selects the patient charting button of the menu template, according to embodiments of the present invention.

FIG. 5 illustrates a graphical user interface displayed when the user selects the patient charting button 206 of the menu template, according to embodiments of the present invention. The display of FIG. 5 includes a biographical summary 502, an interventions section 504, and a vital signs (e.g. vital signs trend) section 506, according to embodiments of the present invention. The biographical summary 502 may display the patient's name, age, and gender as recorded by the EMS technician 114 with the patient charting device 108, according to embodiments of the present invention. The interventions section 504 displays the patient 116 interventions (e.g. treatments administered) recorded with the patient charting device 108, according to embodiments of the present invention. For example, the interventions section 504 includes a listing of each intervention made, the time of the intervention, a description of the intervention (e.g. name of the drug administered), and the name of the person administering the treatment, according to embodiments of the present invention.

The vital signs section 506 includes a historical listing of certain vital signs data observed by the EMS technician 114 and recorded in the patient charting device 108, and stored in the patient charting device 108 and/or the database 118, according to embodiments of the present invention. The historical listing of vital signs data in the vital signs section 506 includes a time stamp, heart rate, blood pressure, respiration rate, blood oxygen level, end-tidal carbon dioxide level, blood glucose level, Glasgow Coma Scale rating ("GCS"), and the name of the technician or device that observed or recorded the vital sign, according to embodiments of the present invention.

Figure 6:
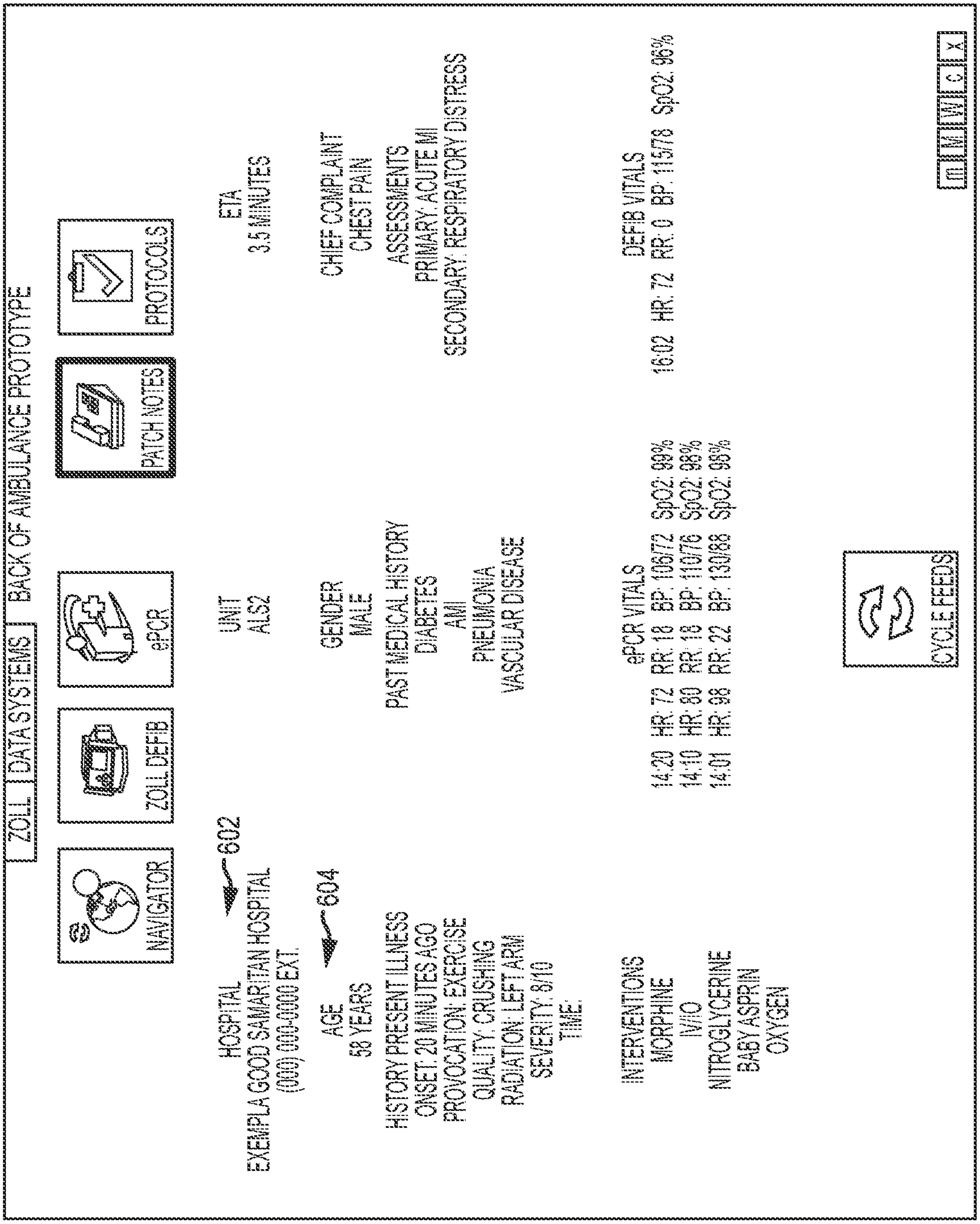
FIG. 6 illustrates a display and graphical user interface displayed when the user selects the "patch notes" button of the menu template, according to embodiments of the present invention.

FIG. 6 illustrates a graphical user interface displayed when the user selects the "patch notes" button 208 of the menu template, according to embodiments of the present invention. Patch notes are notes used by an EMS technician 114 to place a call to a hospital or other treatment facility to confirm that the hospital will accept the patient 116 and/or to provide information about the patient 116 to help the hospital or treatment facility prepare for admission. Because time is typically of the essence for such phone calls (because placing the call can temporarily divert the EMS technician's 114 attention away from patient 116 care), the EMS technician typically consults and interacts with several different devices 106, 108, 110 and/or informal data sources to compile a list of notes to convey to the nurse or other responsible party at the hospital or treatment facility. Such patch notes often take considerable time to assemble, and are often hastily written on a glove, for example, which also results in inaccuracy and in some of the patch notes representing old information by the time the call is placed and the information conveyed to the hospital.

The BOA device 104, on the other hand, automatically creates a display of several different fields that would typically comprise patch notes, according to embodiments of the present invention. The display of FIG. 6 includes fields representing information from multiple different devices, such as, for example, devices 106, 108, 110. The patch notes display may organize the information into a predefined template, and/or may organize the information into a customized template associated with a particular EMS technician 114, according to embodiments of the present invention. Not only does the BOA device 104 automatically receive and display information from multiple different devices 106, 108, 110 in a single display summarized to function as patch notes, but it also automatically refreshes the display to reflect the most recent information, thus permitting real-time conveyance of patient information, according to embodiments of the present invention.

For example, without the BOA device 104, if a patient's heart rate rose from 75 to 115 over the course of three minutes, and if an EMS technician 114 wrote "HR 75" on his glove before consulting his patient chart for name and background information and the driver 112 for location information before calling the hospital three minutes later, the EMS technician 114 might report a heart rate of 75 to the hospital. With the BOA device 104, however, the patch notes are generated automatically and displayed as in FIG. 6, and the Defib Vitals section would list the current heart rate of 115 when the EMS technician 114 conveyed the patient status to the hospital.

In addition to one or more of a Hospital field 602 identifying the name and phone number of the hospital to which the patient 116 is en route and an age field 604 identifying the patient's age, the display of FIG. 6 may also include one or more of a History Present Illness field, an Interventions field, a Unit identification field (e.g. identifying the particular EMS vehicle), a Gender field, a Past Medical History Field, a patient charting device vital signs field, an Expected Time of Arrival field, a Chief Complaint field, an Assessments field, and a patient monitoring device vital signs field, according to embodiments of the present invention.

Each of the fields may be configured to display either past or current or derived content from one or more of the EMS devices (e.g. devices 106, 108, 110) which are communicably coupled with the BOA device 104, according to embodiments of the present invention. For example, the Hospital, Unit, and ETA fields may be based on information received from the navigation unit 110. The Age, Gender, Chief Complaint, History Present Illness, Past Medical History, and Interventions fields may be based on information received from the patient charting unit 108. The patient charting device vital signs field may be based on information received from the patient charting unit 108 (e.g. GCS score), and the patient monitoring device vital signs field may be based on information received from the patient monitoring device 106 (e.g. ECG), according to embodiments of the present invention. According to embodiments of the present invention, a BOA device 104 may be located in the front of the ambulance to permit the driver 112 or another EMS technician to place the call to the hospital based on the real-time patch notes, thereby providing the attending EMS technician 114 more time and attention for direct patient care.

According to embodiments of the present invention, the BOA device 104 receives information from at least one patient monitoring EMS device and at least one non-patient monitoring EMS device. The patch notes screen of FIG. 6 illustrates one example of EMS information (e.g. information related to an emergency medical encounter or transport) from at least one patient monitoring device and at least one other device that does not directly monitor a patient (e.g. a navigation device and/or a patient charting device) on the same display, according to embodiments of the present invention. Similarly, in another embodiment of the present invention, the BOA device 104 receives information from at least one patient clinical device and at least one non-clinical device, and analyzes, combines, stores, displays, and/or transmits the clinical and non-clinical information in a format useful to the user. As used herein, the term "clinical" is used in its broadest sense to refer to that which is directly implicated in monitoring or treatment or diagnosis of a patient. As used herein, the term "non-clinical" is used in its broadest sense to refer to that which is not directly implicated in monitoring or treatment or diagnosis of a patient. For example, a defibrillator is a clinical device, and a navigation device is a non-clinical device. As another example, a patient's ECG information or heart rate is clinical information, while a patient's address is non-clinical information.

Figure 7:
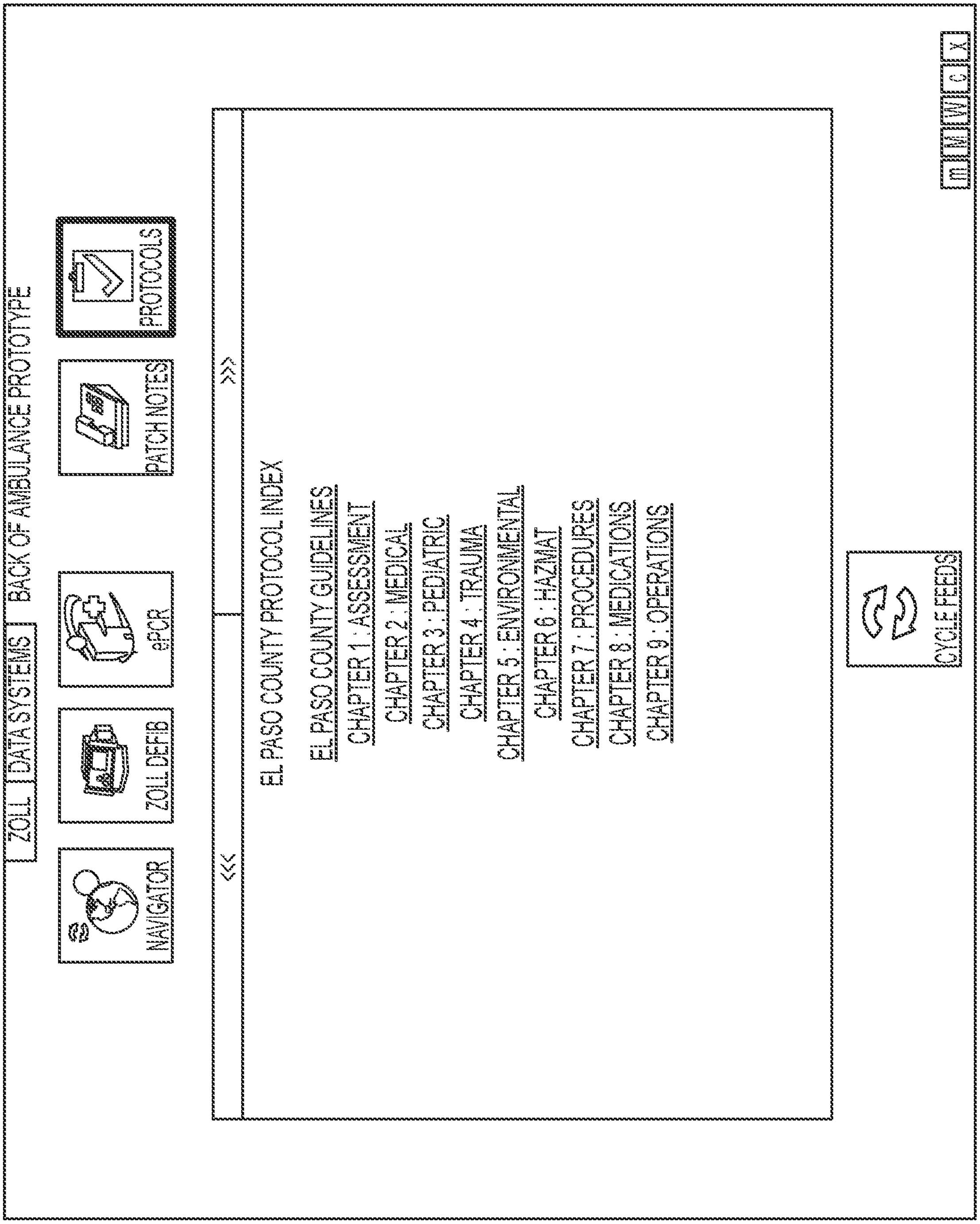
FIG. 7 illustrates a display and graphical user interface displayed when the user selects the protocols button of the menu template, according to embodiments of the present invention.

FIG. 7 illustrates a graphical user interface displayed when the user selects the protocols button 210 of the menu template, according to embodiments of the present invention. The display of FIG. 7 includes an interactive guidelines manual for the particular locale where the medical emergency occurred, where the treatment occurs, and/or where the patient is delivered, according to embodiments of the present invention. Alternatively, the protocols button 210 may link to a manual or guideline document for the use of a particular device and/or the administration of a particular technique and/or information about a drug. For example, the display of FIG. 7 may include an interactive page listing of chapters in a county's protocol index, which may be a locally-stored protocol index and/or a protocol index accessed through an Internet connection. Clicking on one or more of the chapters or links opens a page containing more detail about the particular chapter or subject selected, for example.

Based on the disclosure provided herein, one of ordinary skill in the art will appreciate that the BOA device 104 may be configured to display additional or different subsets of information from one or more EMS devices and/or external data sources. According to embodiments of the present invention, the BOA device 104 not only seamlessly integrates information from a patient monitoring device 106, a patient charting device 108, and a navigation device 110 for display in mobile environment 101, but it also does so for display in a remote environment such as, for example, enterprise environment 102. Enterprise environment 102 may be a hospital and/or dispatch environment, for example.

Data from the BOA device 104 (and therefore data from the devices 106, 108, 110 communicably coupled with the BOA device 104) may be received by one or more enterprise storage servers 126 in an administration environment 103 and stored in an enterprise database 130, and the same information may be accessed and provided by one or more enterprise application servers 128 to a workstation 122 of an enterprise user 124, according to embodiments of the present invention. According to embodiments of the present invention, the BOA device 104 is communicably coupled to the storage server 126 which is communicably coupled to the database 130, and the application server 128 is communicably coupled to the database and to the enterprise workstation 122. Such devices may be communicably coupled via a network 120 such as, for example, the Internet.

When the BOA device 104 receives updated information from one or more of the devices (e.g. devices 106, 108, 110) to which it is communicably coupled, the BOA device 104 sends the updated information to the enterprise storage server 126, which stores the updated information in a database which may be contained on a storage medium 130, according to embodiments of the present invention. Hence, information from one or more devices (e.g. devices 106, 108, 110) may be stored in mobile database 118, remote enterprise database 130, or both, according to embodiments of the present invention. An enterprise user 124, who may be an emergency room nurse monitoring and/or preparing for ambulance arrivals, an emergency room physician, and/or a medical director at home, for example, may access information similar to information displayed by the BOA device 104 by requesting the information via an enterprise workstation 122. For example, the enterprise workstation 122 accesses a web interface and/or thin client web browser application which requests the information over the network 120 from application server 128. Application server 128 queries the database 130 for the information, and returns a display to enterprise workstation 122 that looks the same as or similar to what the EMS technician 114 is currently seeing on the BOA device 104 display, according to embodiments of the present invention.

Figure 8:
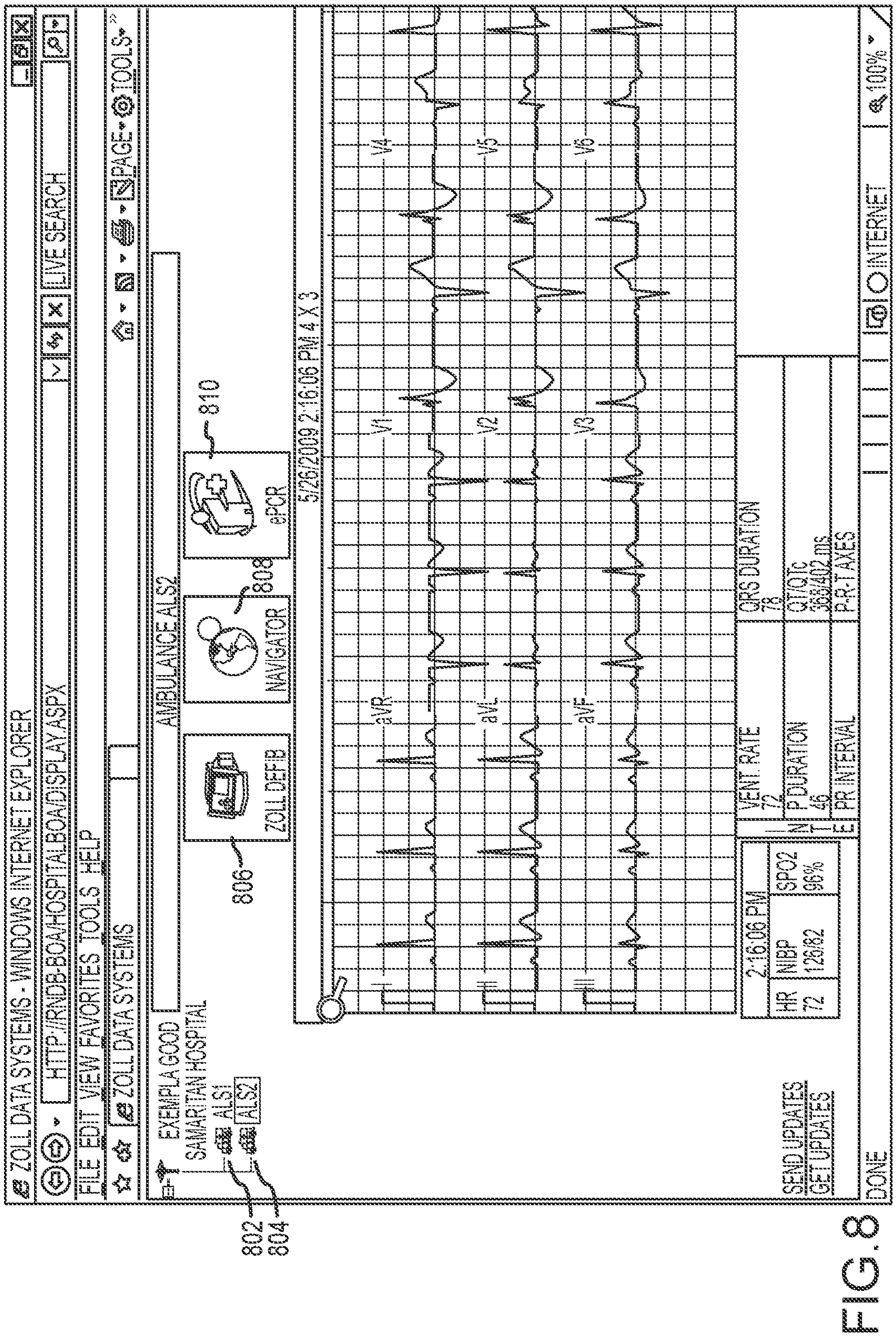
FIG. 8 illustrates an enterprise display and graphical user interface shown when the enterprise user selects the patient monitoring button, according to embodiments of the present invention.
Figure 9:
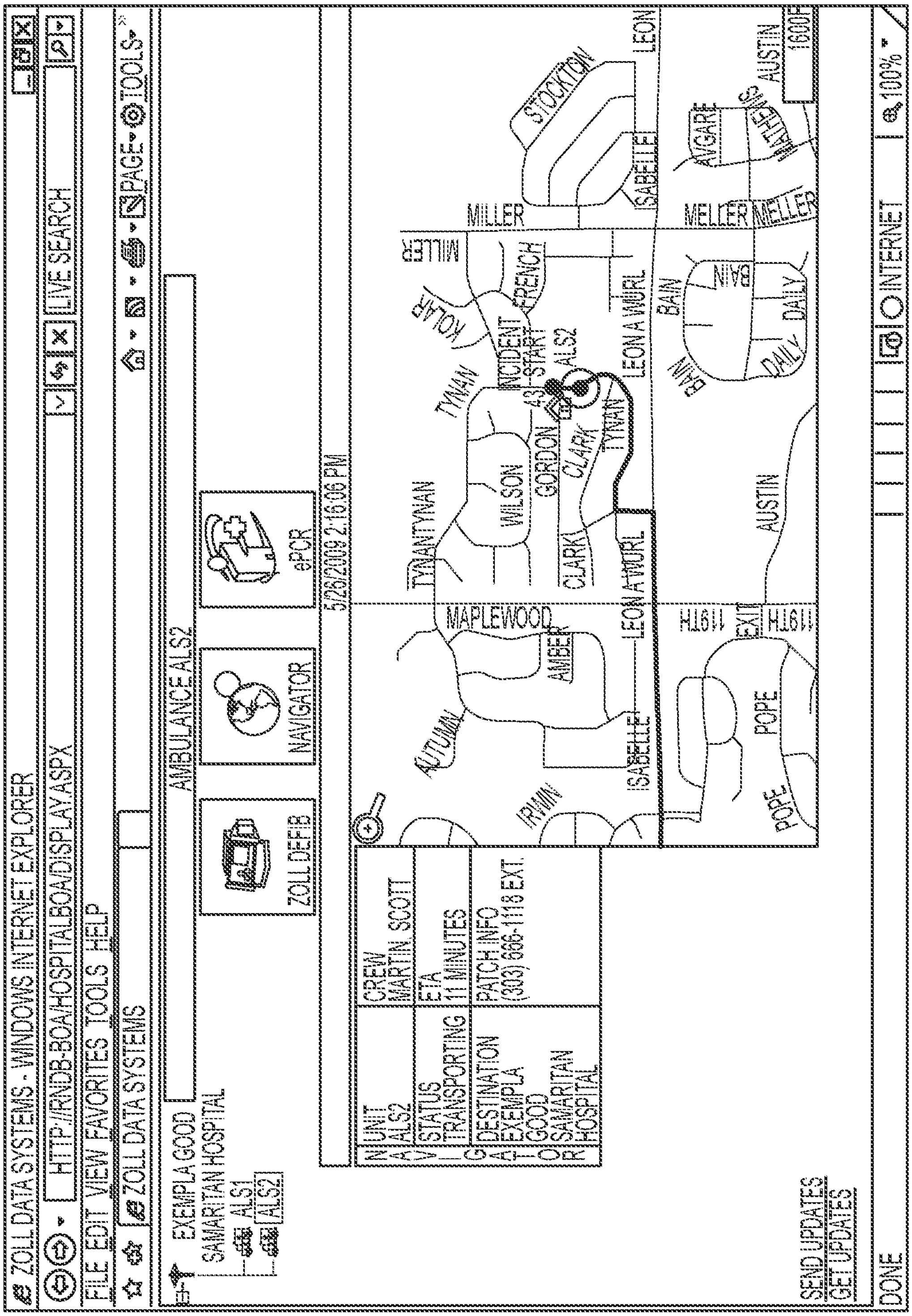
FIG. 9 illustrates an enterprise display and graphical user interface shown when the enterprise user selects the navigation button, according to embodiments of the present invention.
Figure 10:
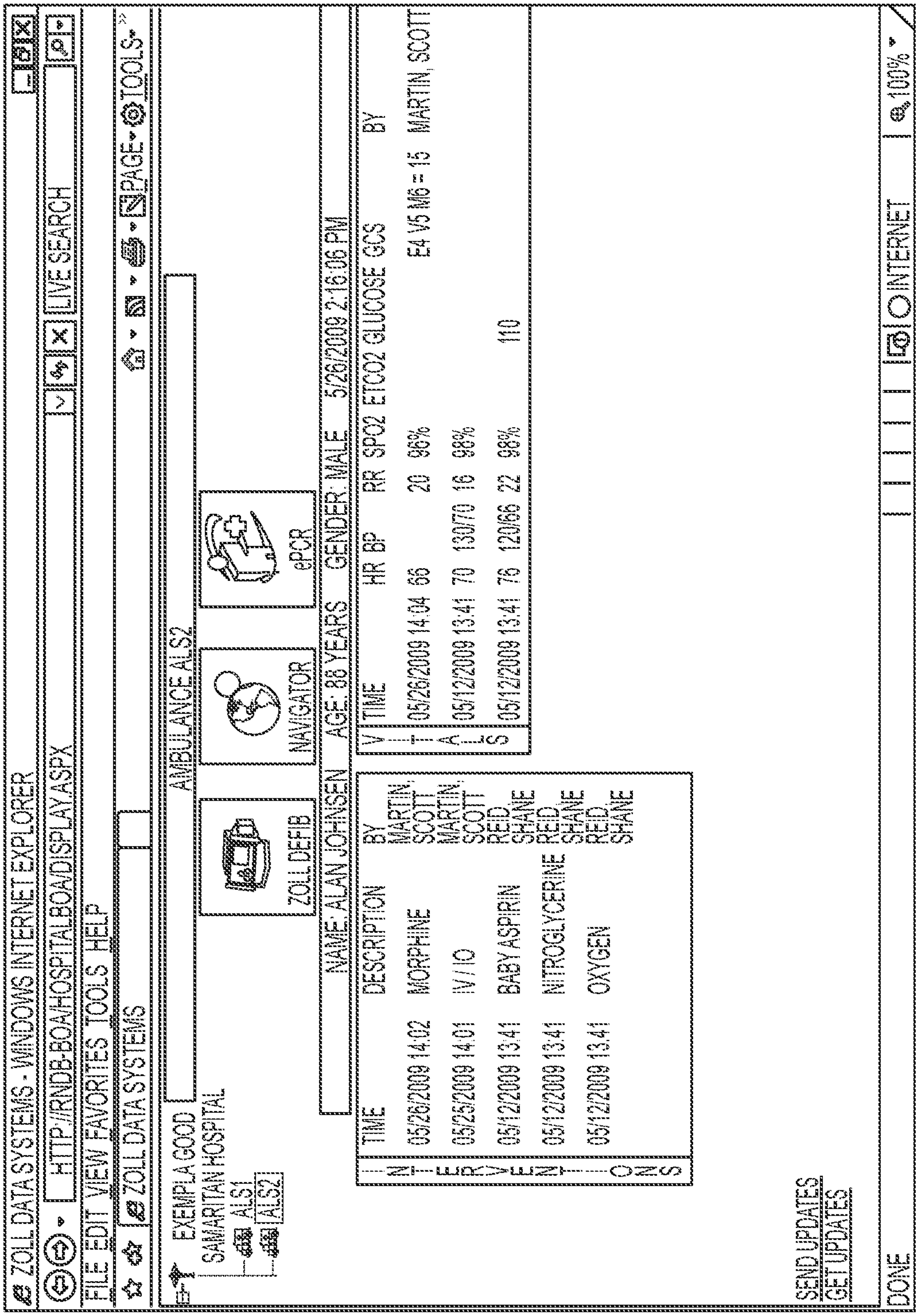
FIG. 10 illustrates an enterprise display and graphical user interface shown when the enterprise user selects the patient charting button, according to embodiments of the present invention.

FIGS. 8-10 illustrate examples of user interface and display screens available to the enterprise user 124 via the enterprise workstation 122, according to embodiments of the present invention. FIG. 8 illustrates a web browser based client interface including, in one portion of the display, a list of available EMS vehicles 802, 804 for which EMS device data is available, according to embodiments of the present invention. Clicking on ALS2 804, for example, brings up a screen similar to FIG. 8 which allows the enterprise user 124 to select one of the buttons, including but not limited to the patient monitoring button 806, the navigation button 808, and/or the patient charting button 810. When user 124 clicks on the patient monitoring button 806, the screen display of FIG. 8 is presented and includes current information from the patient monitoring device 106 of ambulance ALS2, according to embodiments of the present invention. According to embodiments of the present invention, the patient monitoring display of FIG. 8 is automatically updated continuously or semi-continuously; according to other embodiments of the present invention, the user 124 selects "get updates" or the browser's "refresh" button in order to obtain the most current information available. The enterprise display of FIG. 8 contains information similar to the mobile display of FIG. 4, according to embodiments of the present invention.

According to embodiments of the present invention, the website display in the enterprise environment 102 is accessed via a generic internet browser by a doctor waiting in the emergency room for the patient to arrive by ambulance. The website may be secured by logon username and password, for example. Each ambulance may be identified by a vehicle name; the doctor chooses from a list of incoming vehicle, after which the data for that patient is displayed. The data may be shown just as it appears on the mobile screen, also in "clinical time." According to embodiments of the present invention, the enterprise environment 102 website displays data only for those patients whose destination is the same as the destination logged on the user's facility.

When the user 124 clicks on the navigator button 808, the screen display of FIG. 9 is presented and includes current information from the navigation device 110 of ambulance ALS2, according to embodiments of the present invention. The enterprise display of FIG. 9 contains information similar to the mobile display of FIG. 3, according to embodiments of the present invention.

When the user 124 clicks on the patient charting button 810, the screen display of FIG. 10 is presented and includes current information from the patient charting device 108 of ambulance ALS2, according to embodiments of the present invention. The enterprise display of FIG. 10 contains information similar to the mobile display of FIG. 5, according to embodiments of the present invention.

Although FIG. 1 depicts a single BOA device 104 in the mobile environment 101, more than one BOA device 104 may be used in the mobile environment 101 to communicably connect to the same or a different set of devices 106, 108, 110. And although FIG. 1 depicts one mobile environment 101, more than one mobile environment 101 and/or more than one BOA device 104 may be communicably coupled with the administration environment 103 and/or the enterprise storage server 126, according to embodiments of the present invention. According to embodiments of the present invention, the enterprise storage server 126 receives EMS device information from BOA device 104 and stores it in database 130 along with an authenticated time stamp and an identifier associating the information with a particular EMS device and/or a particular EMS vehicle. In this way, data from multiple vehicles and/or multiple devices may be accessed by the enterprise user 124.

Also, the enterprise storage server 130 may securely store the information received from one or more BOA devices 104 for longer periods of time to permit later use of the information. For example, the BOA device 104 may receive patient-identifying information such as name, address, and/or social security number via the patient charting device 108 or directly through the BOA device 104, and then may convey some or all of the patient-identifying information to enterprise storage server 126 with a request for the enterprise storage server 126 to query the database 130 for past records involving the same patient 116. The enterprise storage server 126 may then forward any such records or portions of such records back to the BOA device 104 (e.g. for display in the patient charting screen or the Past Medical History in the patch notes screen) to assist the EMS technician 114 with the current emergency. Similarly, such past EMS encounter record information may also be accessed by the enterprise user 124, according to embodiments of the present invention. A system administrator 134 may access and/or monitor the data in database 130 and/or modify the instructions of the servers 126, 128 via administration workstation 132, which may be communicably coupled to the servers 126, 128, according to embodiments of the present invention.

According to some embodiments of the present invention, the BOA device 104 may connect with (e.g. automatically or manually or selectively) a wearable medical device, such as, for example, a Lifevest® wearable defibrillator, to receive and display patient monitoring information therefrom. The BOA device 104 may also be configured to receive patient-identifying information from such a wearable device, to permit the BOA device 104 to query an external database, for example across network 120, to retrieve additional information about the patient. The BOA device 104 may also be configured to connect with an implantable cardioverter-defibrillator ("ICD") in a similar fashion, according to embodiments of the present invention.

Figure 11:
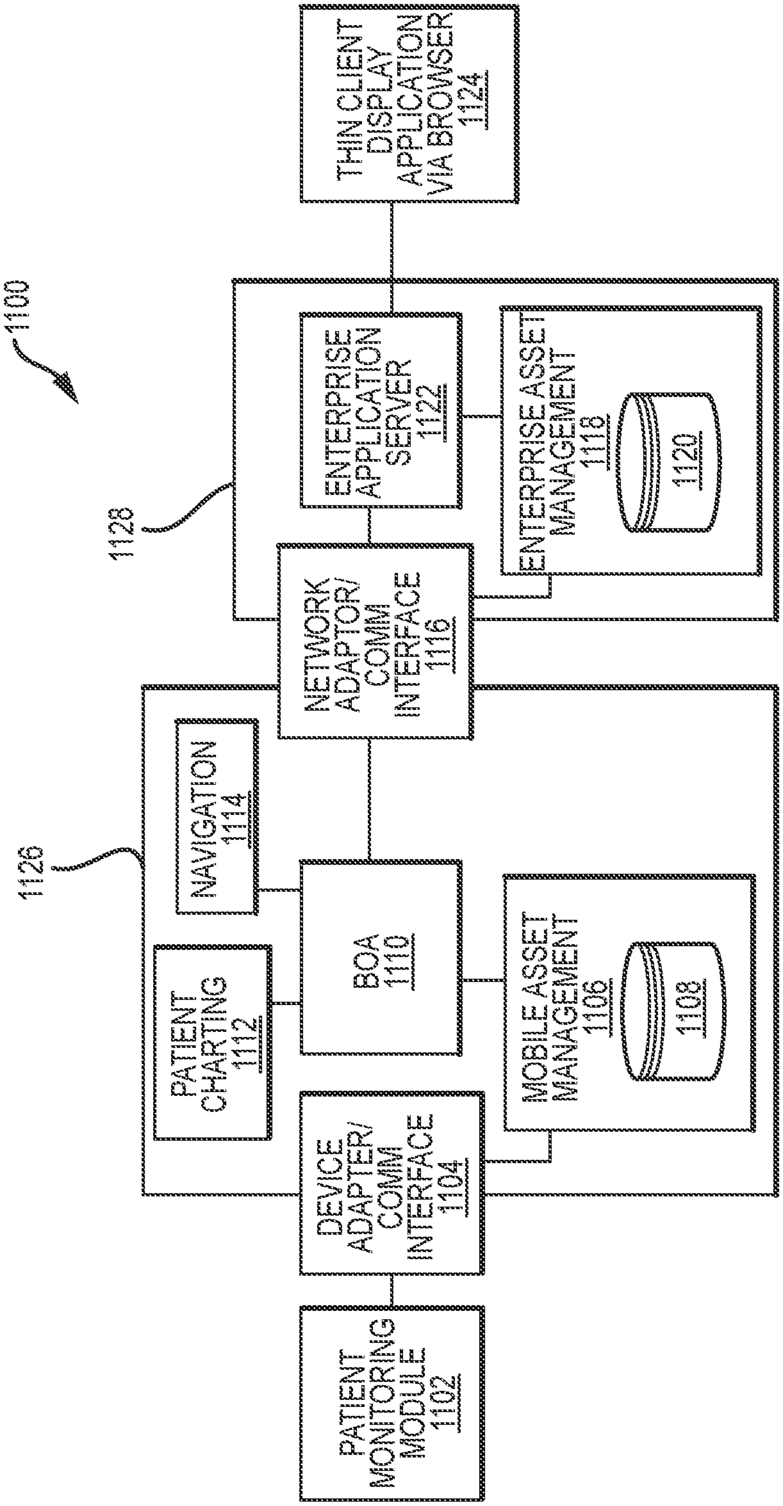
FIG. 11 illustrates a treatment domain system overview for real-time display of medical information collected from multiple different EMS devices, according to embodiments of the present invention.

FIG. 11 illustrates a treatment domain system 1100 overview for real-time display of medical information collected from multiple different EMS devices, according to embodiments of the present invention. System 1100 includes a patient monitoring device module 1102 communicably coupled with mobile domain modules 1126 communicably coupled with remote or enterprise domain modules 1128 communicably coupled with a thin client display module 1124, according to embodiments of the present invention. According to embodiments of the present invention, the database 130 may be accessed by multiple hospitals throughout a region, state, country, and/or the world.

The mobile domain modules 1126 includes the device adapter 1104, a mobile asset management module 1106 which may access a mobile database 1108, a BOA module 1110, a patient charting module 1112, a navigation module 1114, and a network adapter 1116, according to embodiments of the present invention. The remote/enterprise modules 1128 include the network adapter 1116, an enterprise asset management module 1118 which may access an enterprise database 1120, and an enterprise application server module 1122, according to embodiments of the present invention.

The patient monitoring device module 1102 operates the patient monitoring device 106 and generates one or more data pipes containing information about a patient 116 condition. The device adapter/communication interface module 1104 manages data communications between a computing device and one or more medical devices such as, for example, between the patient monitoring device module 1102 and the mobile asset management module 1106 and/or BOA module 1110. The device adapter module 1104 includes one or more of the following attributes, according to embodiments of the present invention:

- Supports multiple communications transports (e.g., devices can use Bluetooth, 802.11, Ethernet, Serial cable).
- Supports multiple data transfer protocols.
- Supports multiple medical device types.

- Supports multiple data storage profiles (e.g., storage to file system, storage by asset management module 1106 to database 1108).
- Allows administrator or user to associate transport, protocol, device and multiple storage profiles together to represent a communication "pipe" over which data can be exchanged with medical devices.
- Supports multiple pipes at the same time.
- Allows administrators or users to specify one or more specific medical devices to which it communicates in which case the module 1104 will use transport specific discovery protocols to find and attach to the devices.
- Allows administrators or users to specify ANY as a medical device in which case it will use transport specific discovery protocols to find and attach to any compatible medical device found.
- When a pipe is configured to use a protocol which does not support discovery (e.g. serial cable), module 1104 will allow the device to initiate the connection and then allow or deny it based on whether the specific medical device is selected or not.
- Supports multiple client applications (local or remote) by allowing them to connect to module 1104 and receive asynchronous notification of data arrival from medical devices and a means to retrieve the data.
- Maintains a communications 'pipe' should the medical device have a data asset to communicate, regardless of whether any application is running or ready to receive the data asset.
- A user may configure the medical device(s) applications communicate with, and such configuration may be persistent and easily changed.
- Communications policies may be configurable. For instance, Bluetooth may require pairing with a device before communications occur. A user may configure whether the pairing is 'automatic' or 'manual' or 'continuously reacquired', for example.
- Applications may access previously received data assets via a relatively simple, expressive API.
- Applications may be notified of newly received assets and may filter those notifications based on specific devices and/or asset type.
- Applications may query the communications layer for status, available devices, and the like, for customizable user interface elements.
- The communications layer may be controllable from a notification icon which also indicates status.
- Configurable items may be protected from malicious or erroneous alteration by common users through the use of a privileged 'admin' mode and a common user mode in the notification area icon applet.
- Configuration may be 'portable' and 'distributable,' such that one configuration may be created and copied to each device rather than having to actually configure each device through a notification applet.
- Particular features or limitations of the communications 'pipe' may be hidden from the application by default.
- The communications layer may itself be layered and support multiple plug-in style transport drivers for managing different communications transports and multiple plug-in style protocol drivers for handling the receipt of data assets from different devices and different asset types. This may allow for the rapid extension of the communications layer to new transports or to new protocols as they are developed.

Figure 12:
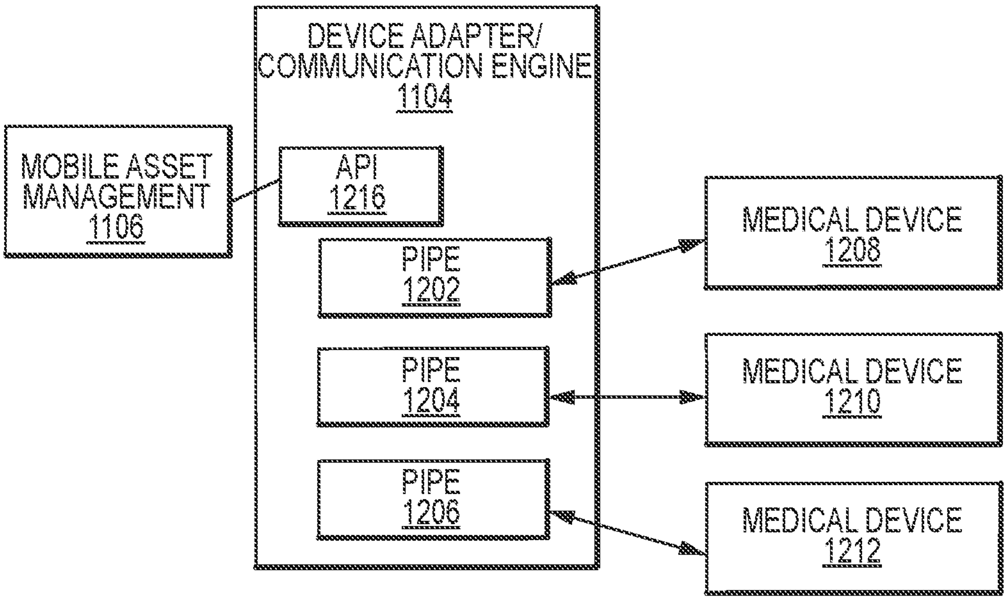
FIG. 12 illustrates a device adapter/communication engine and medical device interface, according to embodiments of the present invention.

FIG. 12 illustrates a diagram of the device adapter/communication module 1104, which includes one or more pipes 1202, 1204, 1206 each associated with a medical device 1208, 1210, 1212. The communication module 1104 may be a PELICAN™ communication interface available from Zoll Data Systems of Broomfield, Colo., according to embodiments of the present invention. According to embodiments of the present invention, the communication engine 1104 is an "always on" operating system service which implements the communications pipes 1202, 1204, 1206 and handles the incoming data from medical devices 1208, 1210, 1212. Communication engine 1104 also includes an API 1216, which is a collection of objects and methods exposed by the communications engine 1104 which can be used by an application to configure and interact with the engine 1104 for tasks like getting data assets and configuring the engine 1104, according to embodiments of the present invention. For example, the mobile asset management module 1106 may interact with the API 1216 to receive medical device data.

Figure 13:
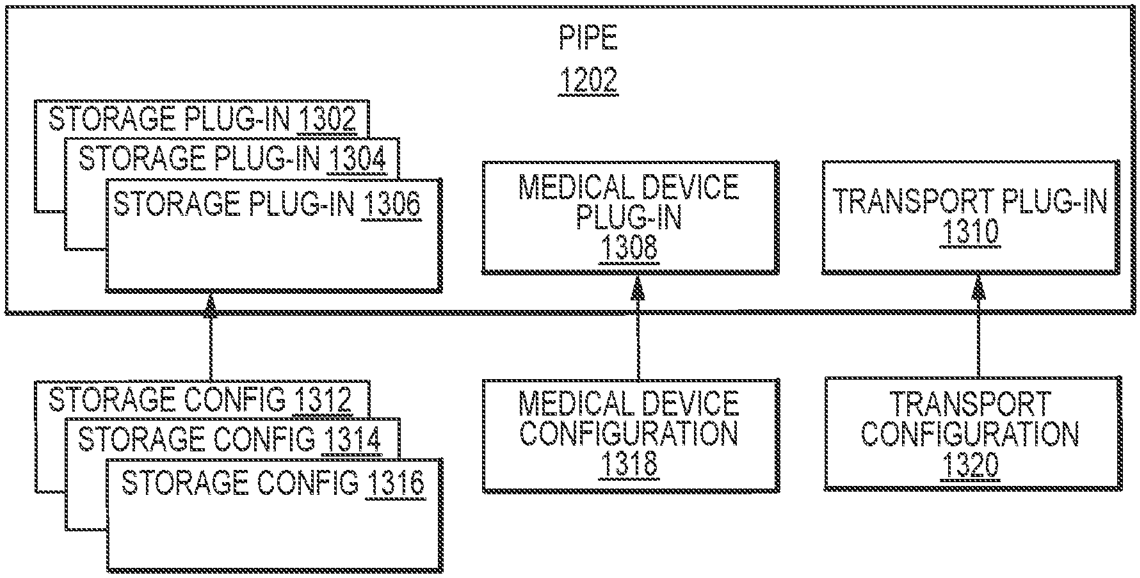
FIG. 13 illustrates an exemplary pipe, according to embodiments of the present invention.

FIG. 13 illustrates a diagram of pipe 1202, according to embodiments of the present invention. Pipe 1202 includes one or more storage plug-ins 1302, 1304, 1306 associated with one or more storage configurations 1312, 1314, 1316 of the medical device; a medical device plug-in 1308 associated with a medical device configuration 1318 of the medical device, and a transport plug-in 1310 associated with a transport configuration 1320 of the medical device, according to embodiments of the present invention. As used herein, a "transport" is an operating system supported underlying communications medium, for example TCP/IP, Bluetooth, and Serial. Some transports are packet oriented (e.g. TCP) while others are stream oriented (e.g. Serial). Some support discovery, some do not. Some support pairing, some do not. Each transport may include unique configurations.

A transport plug-in may be a .NET assembly that is dynamically loaded by the communications engine 1104 and which provides data communications support for a specific transport (e.g. Serial Port, Bluetooth, TCP/IP, and File System). The communications engine 1104 may be configured for auto-pairing (e.g. for transports that support pairing, the engine 1104 uses rules specific to the transport to automatically create and maintain pairings with medical devices depending on configuration and user preference) and/or for auto-discovery (e.g. for transports that support discovery, the engine 1104 may be configured to automatically find new medical devices and enter them into the known device list), according to embodiments of the present invention.

A medical device plug-in may be a .NET assembly that is dynamically loaded by the communications engine 1104 which provides transport independent data communications services for a particular type of medical device, for example ZOLL M/E-Series ZOLLModem or ZOLL E-Series DUN. A storage plug-in may be a .NET assembly that is dynamically loaded by the communications engine 1104 which provides storage services to the engine.

As shown in FIG. 13, a pipe may be a combination of transport, medical device, and storage configurations which represent a medical device from which the user has indicated data will be received, and which allows communications to occur. Pipes may be configured by the user and/or may be predefined. For example, a pipe may specify Transport Serial Port with configuration (COM1, Baud=9600), Medical Device E/M Series ZOLLModem (Any Medical Device) and Storage (Local File System). This configuration would accept data assets from any device connected to COM1 at 9600 baud and store them to the local file system. As another example, a pipe may specify Transport Bluetooth (Baud=115200, Auto-Pair), Medical Device E/M Series ZollModem (ZOLL005611), Storage (Local File System) and Storage (Asset Management). This configuration would cause Bluetooth to pair to ZOLL005611, maintain that pairing even when broken and accept any data assets from that specific device and store them both to the local file system and submit them to Asset Management (e.g. mobile asset management module 1106 and/or enterprise asset management module 1118).

As yet another example, a pipe may specify Transport Bluetooth (Baud=115200, Auto-Pair), Medical Device E/M Series ZOLLModem (Any Device). This configuration would cause Bluetooth to automatically pair with any medical device found during periodic discovery and accept any data assets from any paired device and store them via all loaded and enabled storage plug-ins. As yet another example, a pipe may specify Transport TCP/IP (LocalIP=192.168.1.20, Port=7743), Medical Device E/M Series DUN (Any Device), Storage (Asset Management). This configuration would cause the engine 1104 to start listening on the specified IP address and port for DUN traffic and store it via Asset Management (e.g. by sending it to mobile asset management module 1106 and/or enterprise asset management module 1118), according to embodiments of the present invention.

Figure 14:
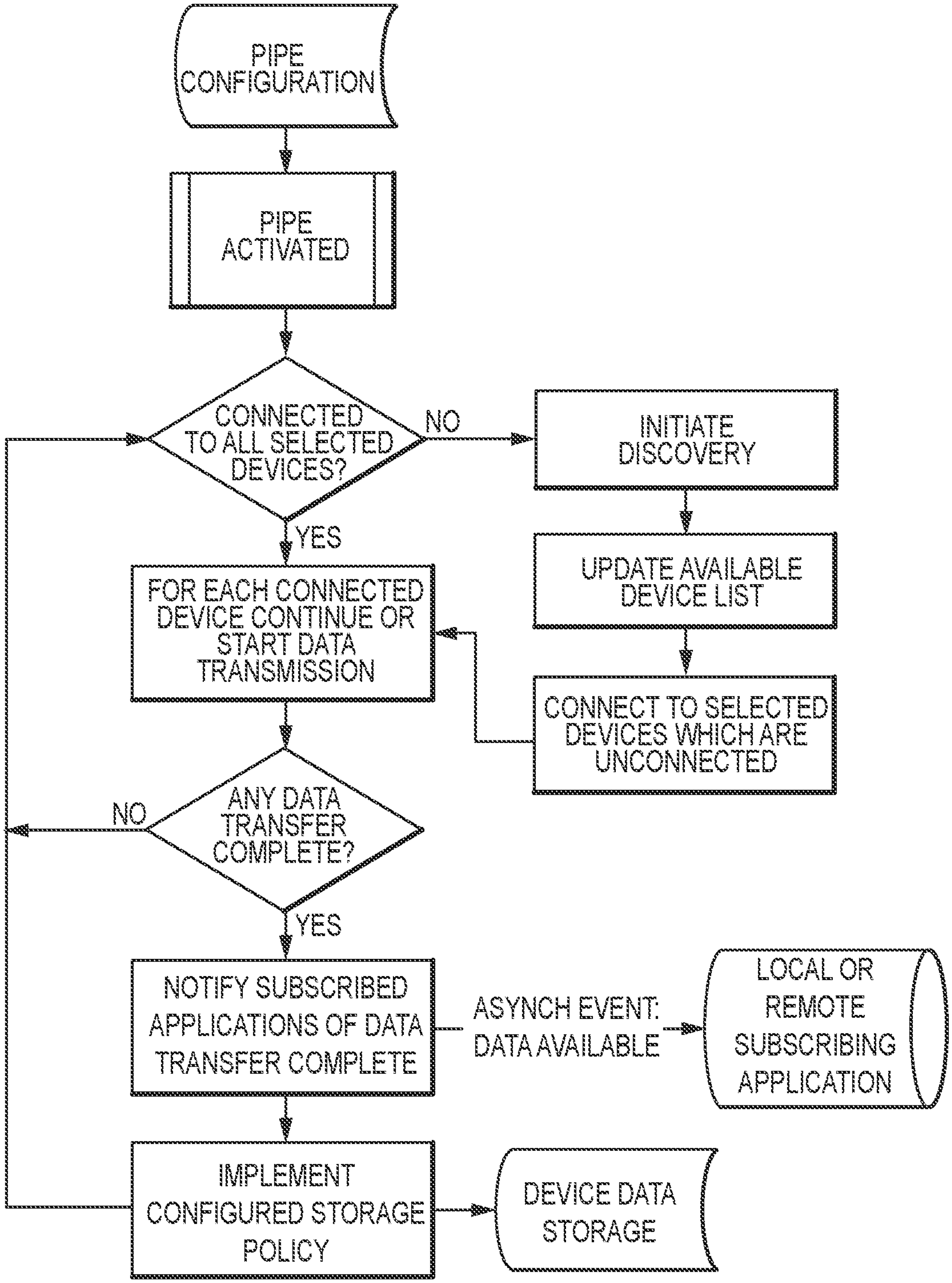
FIG. 14 illustrates a method performed by a pipe of the device adapter that uses discovery supporting transport, according to embodiments of the present invention.
Figure 15:
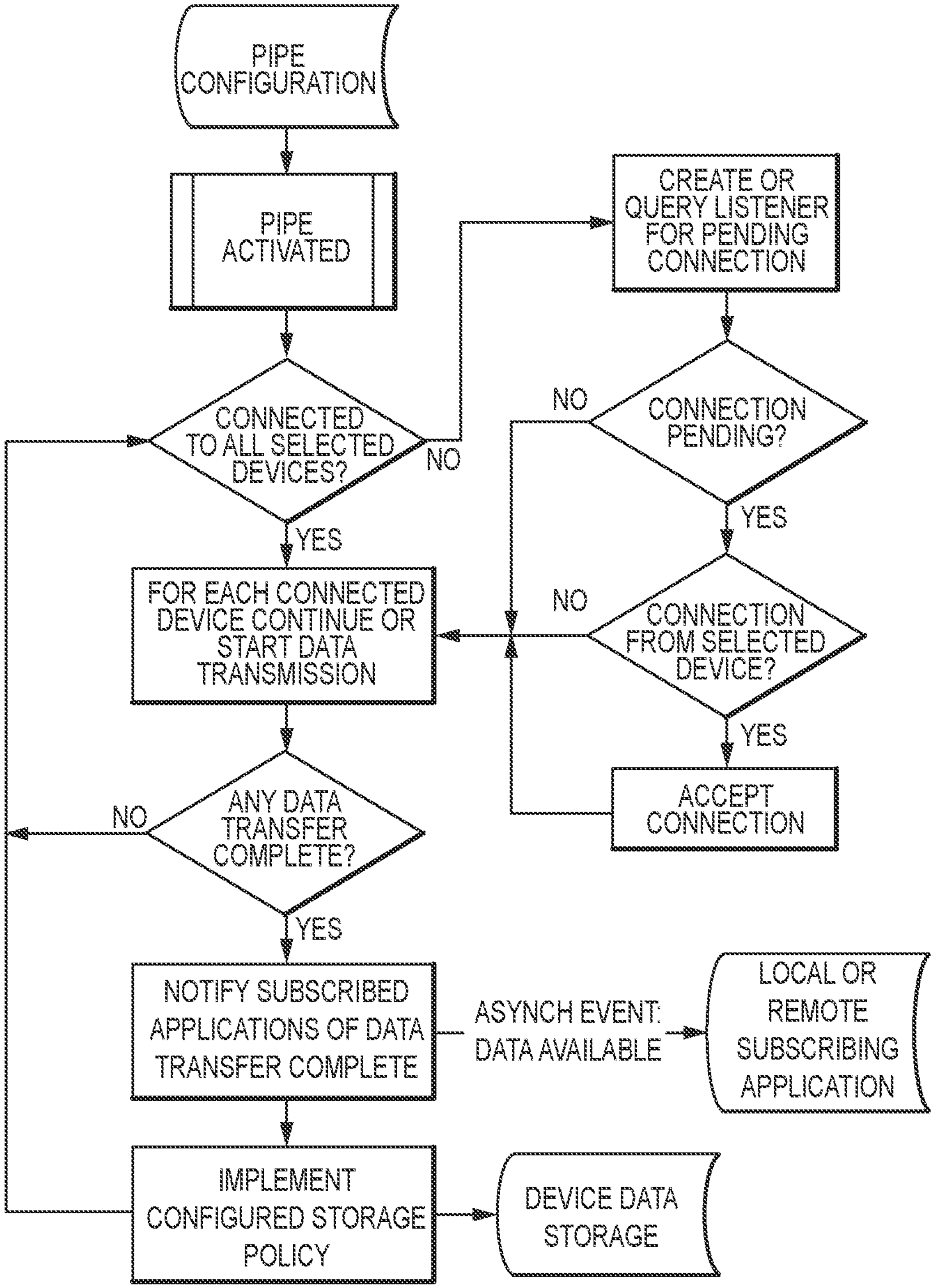
FIG. 15 illustrates a method performed by a pipe of the device adapter that uses non-discovery supporting transport, according to embodiments of the present invention.

For each "pipe" of device adapter 1104 that uses Discovery Supporting Transport, the adapter 1104 performs the method outlined in FIG. 14, and for each pipe of device adapter 1104 that uses Non-Discovery Supporting Transport, the adapter 1104 performs the method illustrated in FIG. 15, according to embodiments of the present invention.

As described above, the mobile asset management module 1106 receives medical device data from the device adapter and communications interface 1104, according to embodiments of the present invention. The mobile asset management module 1106 performs the secure storage, retrieval and management of medical device data together with asynchronous events informing other applications of the storage or modification of these data assets. The mobile asset management module 1106 supports local or remote service oriented API to store, retrieve and modify medical device data, and provides local or remote asynchronous message-based notification of events to applications which subscribe for them, according to embodiments of the present invention. These events may include notification of the arrival of medical device data.

The BOA module manages data feeds from multiple data providers (including but not limited to, the device adapter 1104, the patient charting module 1112, and the navigation module 1114) and presents these feeds on a touch-screen flat panel, according to embodiments of the present invention. The BOA module 1110 also communicates these aggregated data elements to a back-office module (e.g. the enterprise asset management module 1118). The patient charting module 1112 controls the patient charting device 108 and the information sent and received by it, and the navigation module 1114 controls the navigation device 110 and the information sent and received by it, according to embodiments of the present invention. The BOA module 1110 includes one or more of the following attributes, according to embodiments of the present invention:

- Allows the user to configure the device adapter/communication interface module 1104, including but not limited to selection of a medical device.
- Allows the user to select a patient charting device from which it will receive a data feed containing medical record information as it is entered in patient charting device.
- Allows the user to select a navigation device from which it will receive a data feed containing navigational and dispatch information on a periodic basis.
- Receives notification from the communication interface module 1104 and/or the mobile asset management module 1106 about the arrival of new medical device data including but not limited to 12-lead ECG and vital trend records.
- Receives asynchronous messages from a selected patient charting device which contain data about the currently open patient record including but not limited to: patient demographics, medical history, current assessments, interventions performed and/or vital signs.
- Receives asynchronous messages from a selected navigation device which contains data about the current dispatch state, destination, crew, location, route and/or map of current position.
- Cyclically presents a graphic display of each of the received data feeds for viewing in the back of the ambulance on the flat panel, or elsewhere on another display device.
- Allows the caregiver or EMS technician 114 to temporarily freeze the cycling display on a feed for more careful examination of that particular data in that particular information template.
- Aggregates the data feeds into a data construct which is sent periodically to the enterprise asset management module 1118.
- Presents a customer customizable view of the aggregated data feed for the purpose of facilitating a verbal report to the receiving facility (e.g. a report in the Patch Notes information template displayed on the BOA device 104).
- Presents the user with the ability to view the regional EMS protocols for reference.

Figure 16:
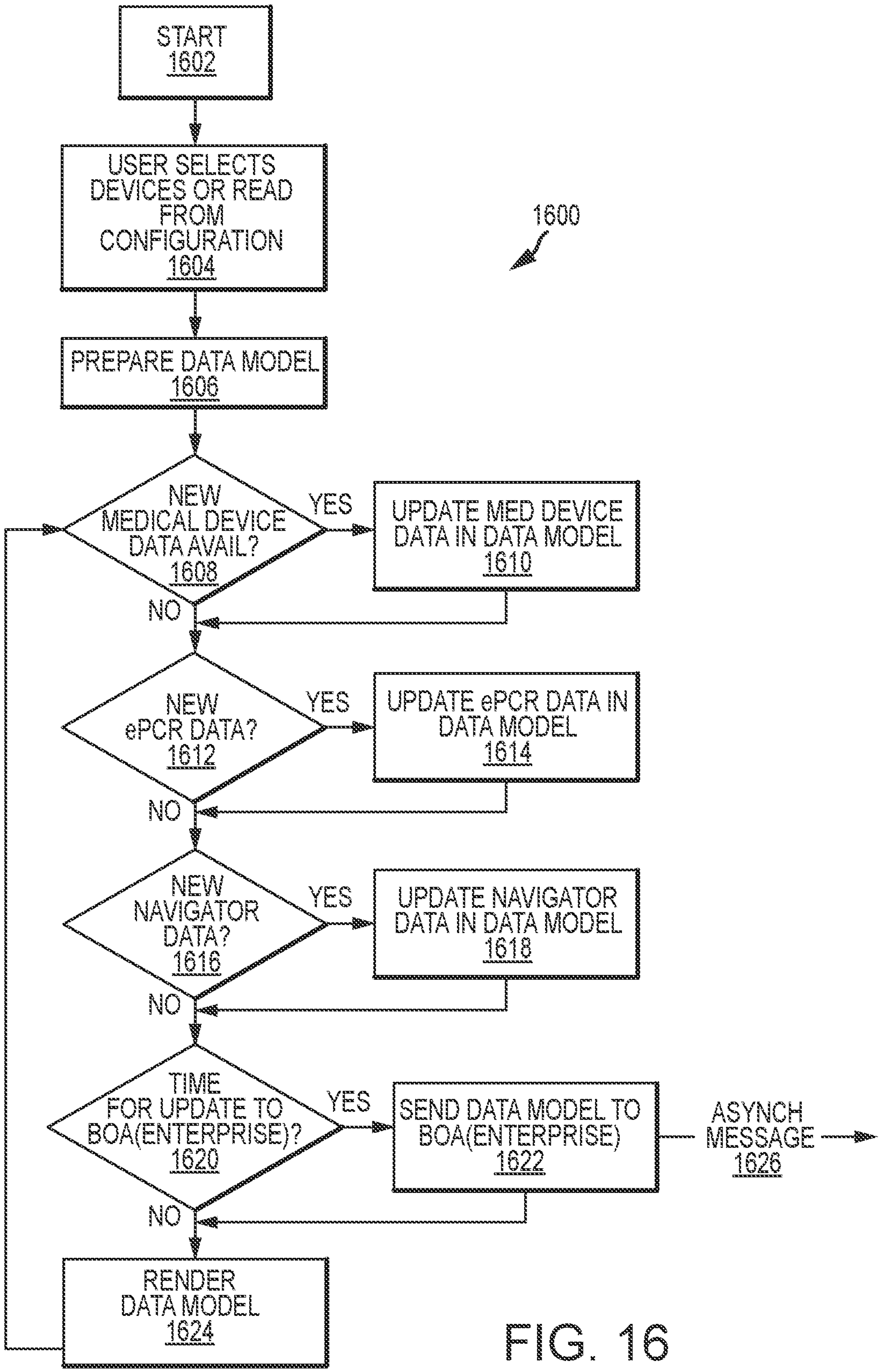
FIG. 16 illustrates a method performed by a BOA module, according to embodiments of the present invention.

FIG. 16 illustrates a logic flow chart 1600 executed by the BOA module 1110, according to embodiments of the present invention. The logic flow chart 1600 starts at block 1602. A user selects particular devices or selects a "read from" configuration to determine which devices' data will be read and displayed by the BOA device 104 (block 1604). A data model is prepared (block 1606), for example the current state of the system that will be displayed on the BOA device 104 and which may eventually be communicated to the enterprise environment 102 and/or enterprise application server 128. The data model may expand to contain other data elements as feeds are added, and may contract to eliminate container properties for unused data feeds (e.g. installations that do not include a patient charting device 108), according to embodiments of the present invention. The BOA module 1110 queries the mobile asset management module 1106 to determine whether new medical device data is available (block 1608) and, if so, updates the medical device data in the data model (block 1610). The BOA module 1110 queries the mobile asset management module 1106 to determine whether new patient charting data is available (block 1612) and, if so, updates the patient charting data in the data model (block 1614).

The BOA module 1110 queries the mobile asset management module 1106 to determine whether new navigation data is available (block 1616) and, if so, updates the navigation data in the data model (block 1618). The BOA module 1110 determines whether it is time to send updated information to the enterprise asset management module 1118 (block 1620) and, if so, sends the data model to the enterprise asset management module (block 1622) and generates an asynchronous message (block 1626). According to embodiments of the present invention, the asynchronous message generated at block 1626 is destined for the enterprise application server 128; according to alternative embodiments of the present invention, the asynchronous message generated at block 1626 is destined for the enterprise storage server 126 which, in turn, stores the data and notifies the enterprise application server 128 of the data's availability. The data model is then rendered (block 1624), for example in the form of a display update on the BOA device 104, according to embodiments of the present invention. According to embodiments of the present invention, the procedures indicated by blocks 1608, 1612, 1616, and 1620 are not executed as "stages" but are instead each events which trigger a different thread of execution that modifies a data model, which in turn triggers the update of the BOA device 104 display.

The network adapter/communication interface module 1116 is a communications channel that includes one or more of the following attributes, according to embodiments of the present invention:

- General purpose and data format independent. Each application may be responsible for the format of its messages.
- Message addressing may be by name rather than transport address (IP address for instance) so that messages can be sent to entities for which no route currently exists (e.g. when the sender is disconnected from the Internet). Name resolution into actual machine address may be deferred until a route actually exists.
- Tree relationship between entities that use communication interface module 1116, in which name information may be "percolated" up the tree but not down. As such, each node has a simple routing choice: if the name is the current device or below, route there, otherwise route to the current device's parent. The root of the tree may be the primary message broker and it accumulates all name information. The primary message broker is the unique node in the communications tree which contains all name information and thus can perform routing from one sub-tree to another, according to embodiments of the present invention.
- Message delivery may be deferred until the recipient actually appears. Messages may be stored until the recipient becomes routable.
- Messages may be stored in a transaction safe database at each node so that even a node unexpectedly failing does not risk message loss.
- Full encryption of messages may be maintained until the recipient actually receives them. While stored in databases, the messages may remain encrypted.
- Robust operation over intermittently connected wireless connections. Messages may be stored until a connection is resumed. Within certain time-limits, if the connection is restored, message transmission may continue from where it left off rather than starting anew.
- Messages intended for machines or applications that are 'local' may be routed locally even when that segment of the tree is disconnected from the primary message broker.
- Messages may be sent with an expiration time after which the message will not be delivered and the sender may be notified of the expiration.

The communications interface 1116 may be a MERCURY™ communication interface available from Zoll Data Systems of Broomfield, Colo., according to embodiments of the present invention.

The messaging components for the BOA module 1110 may be implemented using the communication interface module 1116 as a channel. These messaging components implement one or more of the following characteristics, according to embodiments of the present invention:

- Publish-Subscribe Model: The data feed consumers (e.g. the BOA mobile module 1110) subscribe with the providers (e.g. the patient charting module 1112) to receive the data feed. The subscription request includes the duration of the subscription. As the providers modify the data feed items, the data feed items are sent to all subscribers. According to embodiments, the BOA module 1110 is a data feed consumer for feeds from the patient charting module 1112 and the navigation module 1114 but a data feed provider for the aggregated feed going to the enterprise asset management module 1118.
- Message Queue Throttling: Using the message expiration feature of the communications interface module 1116, all messages may be sent with a short expiration time and then a new, current copy is sent upon expiration notification. This keeps the system from having a large queue of stale data feed messages when components are disconnected; at most, one current message is in the system.
- Complex message format: The data feed messages include graphical, textual and binary data which may be turned into objects by the recipient for ease of use.

The enterprise asset management module 1118 receives an aggregated data feed from multiple BOA modules 1110 and provides presentation of those aggregated data feeds on displays remote from the originating ones. For example, such aggregated data feeds may be fetched from the database 1120 associated with the enterprise asset management module 1118 by the enterprise application server module 1122 and displayed to an enterprise user via a thin client display application module 1124 running on a web browser, according to embodiments of the present invention. Such a web page may be secured, encrypted, password-protected, and/or HIPAA compliant, according to embodiments of the present invention. The enterprise asset management module 1118 includes one or more of the following attributes, according to embodiments of the present invention:

- Receives asynchronous messages from multiple BOA modules 1110 containing aggregated data feeds including but not limited to data feeds from patient charting modules 1112, navigation modules 1114, and medical devices.
- Uses destination data from the BOA module 1110, set either by the navigation module 1114 or manually by the user on the flat panel BOA device 104, creates a web page for each hospital destination containing the feeds from each BOA module 1110 with that hospital as the destination.
- Asynchronously updates the web page as new versions of the aggregated data feeds arrive for each BOA module 1110 sending data regarding a patient 116 en route to the hospital or treatment facility.
- Renders the aggregated data feeds with diagnostic resolution of the 12-Lead data.
- Prevents unauthorized access by employing hospital specific logins to the secured EMS data feed web page module 1124.

Although FIG. 1 illustrates the BOA device 104 communicably coupled with a patient monitoring device 106, a patient charting device 108, and a navigation device 110, in alternative embodiments of the present invention the BOA device 104 is communicably coupled with additional EMS-related devices not shown in FIG. 1, and/or is communicably coupled with multiple devices of the kind shown in FIG. 1, and/or is communicably coupled with different models or versions of the devices of the kind shown in FIG. 1. For example, the BOA module 1110 may be configured to communicate EMS-related device data to and from, either directly and/or indirectly via a device adapter/communication interface module 1104, one or more of the following devices: a defibrillator, a patient charting device, a navigation device, a GPS device, a pulse oximeter, an automatic cardiopulmonary resuscitation device (e.g. Autopulse® non-invasive cardiac support pump), a driver safety monitoring system, a standalone blood pressure monitor, a blood glucose measurement device, an inventory control system, a blood alcohol monitor, a breathalyzer instrument, a fusion pump, a ventilation device, a wearable defibrillator device (e.g. LifeVest® device), and a crew scheduling system. A defibrillator or patient monitoring device may be one of a broad range of defibrillators or patient monitoring devices made and/or sold by a number of different manufacturers, according to embodiments of the present invention. The BOA device 104 may also be communicably coupled with, and configured to aggregate with patient data, data obtained from a CodeNet Writer™ device manufactured by Zoll Medical Corporation, or the like, according to embodiments of the present invention.

According to embodiments of the present invention, the BOA device 104 is communicably coupled to only one or two of the patient monitoring device 106, the patient charting device 108, and the navigation device 110, and is configured to organize and display EMS information from only the one or two such devices.

Although the modules and applications described with respect to FIG. 11 can roughly correspond to the hardware devices with similar designations in FIG. 1, one of ordinary skill in the art, based on the disclosure provided herein, will understand that the various modules and/or instructions for performing the described procedures may be located on different and various hardware devices and/or on hardware devices not depicted, in different combinations, according to embodiments of the present invention. For example, although the BOA device 104 may be a touch-screen PC including and configured to perform the tasks of the BOA module 1110, the BOA device 104 may alternatively be a simple display device such as a monitor, with the computational functions of the BOA module 1110 and/or mobile asset management module 1106 performed by other hardware, such that only the display information is communicated to the BOA device 104, according to embodiments of the present invention.

The BOA device 104 according to embodiments of the present invention may be configured to facilitate data entry via a touch screen device with software that permits rapid and easy data entry, similar to the Quicklog capability of the Zoll Data Systems RescueNet® ePCR Suite. In addition, the BOA device 104 may be configured to permit selection and display of patient monitoring data (e.g. 12-lead ECG data) from prior transports and/or other agencies retrieved from mobile database 118 and/or enterprise database 130, according to embodiments of the present invention. Such historical and/or shared patient data may also be made available to hospitals, and/or stored by hospitals or other care institutions as part of a data management program. The BOA device 104 may also be configured to display streaming ECG information similar to the "live" display of such information by a defibrillator device, for example. The BOA device 104 may also be configured to display feedback to the EMS technician 114 about cardiopulmonary resuscitation being performed, to evaluate the CPR technique during and/or after it is administered. According to embodiments of the present invention, the BOA device 104 may be configured to communicably couple with and receive information from an accelerometer and/or other CPR evaluation device, such as a device configured to detect the presence of and/or the timing of and/or the depth/displacement of and/or the velocity of and/or the acceleration of chest compressions, for example the devices and methods described or referenced in U.S. Pat. No. 6,390,996 issued on May 21, 2002, U.S. Pat. No. 6,827,695 issued on Dec. 7, 2004, U.S. Pat. No. 7,122,014 issued on Oct. 17, 2006, and U.S. Pat. App. Pub. No. 2006/0009809 published on Jan. 12, 2006, which are incorporated by reference herein in their entireties.

Figure 17:
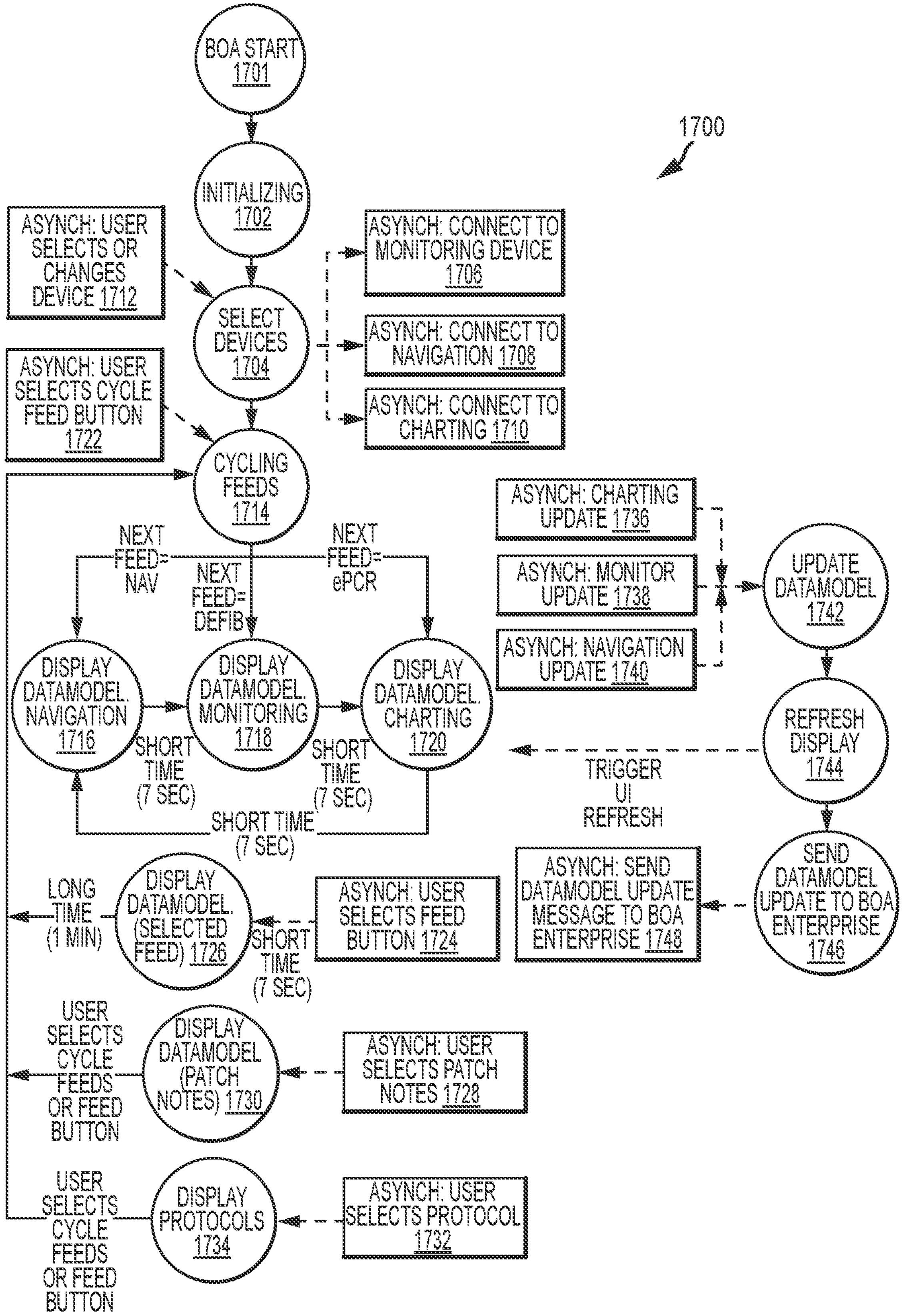
FIG. 17 illustrates a method performed by a BOA module, according to embodiments of the present invention.

FIG. 17 depicts a flow chart 1700 illustrating a method performed by BOA module 1110, according to embodiments of the present invention. The process begins at block 1701. The BOA module 1110 is initialized (block 1702), and the user may then select devices (block 1704) from which medical and/or EMS information will be received. For example, such device selection may involve generating an asynchronous message to be received by the patient monitoring module 1102 for establishing a connection (block 1706), an asynchronous message to be received by the navigation module 1114 for establishing a connection (block 1708), and/or an asynchronous message to be received by the patient charting module 1112 for establishing a connection (block 1710). A different subset of devices (different devices, fewer devices, or more devices) may be selected at any time when the user initiates an asynchronous event to select or change devices (block 1712).

Once devices have been selected, the BOA device 104 cycles through a series of different displays (block 1714). This cycling may be programmed to occur at preset intervals; for example, the BOA device 104 may be configured to cycle the display between different data models every seven seconds. For example, a navigation device data model may be displayed (block 1716), which may be similar to the data model depicted in FIG. 3, for example. After a preset time, the display may be switched to a patient monitoring device data model (block 1718), similar to the data model depicted in FIG. 4, for example. After another preset time, the display may be switched to a patient charting device data model (block 1720), similar to the data model depicted in FIG. 5, for example. Once the display has cycled through each data model, it may return to the first data model displayed and repeat the cycle, according to embodiments of the present invention. Such a cycling may be initiated or re-initiated during other tasks when the user initiates an asynchronous event (block 1722) by selecting the cycle feed button (similar to the button 318 of FIG. 3), for example.

When a user selects one of the "feed" buttons (block 1724), an asynchronous event is generated causing the data model corresponding to that feed to displayed (block 1726) for a longer predetermined period of time, for example one minute. As an example, if the user selects the patient charting button 206 (see FIG. 2), the patient charting data model similar to FIG. 5 will immediately be displayed and will remain displayed for a period of time longer than the default cycle time. When a user selects the patch notes button 208 (block 1728), an asynchronous event is generated causing the patch notes data model similar to FIG. 6 to be displayed (block 1730) until the user next selects the cycle feeds button 318 or a particular feed button 202, 204, 206, according to embodiments of the present invention. When a user selects the protocols button (block 1732), an asynchronous event is generated causing the protocols data model similar to FIG. 7 to be displayed (block 1734) until the user next selects the cycle feeds button 318 or a particular feed button 202, 204, 206, according to embodiments of the present invention.

When one of the EMS devices receives or generates new data, it may be configured to generate an asynchronous notification to be received by the BOA module 1110, according to embodiments of the present invention. For example, the patient charting module 1112 may generate an asynchronous message when it has new information to share (block 1736), the patient monitoring module 1102 may generate an asynchronous message when it has new information to share (block 1738), and the navigation module 1114 may generate an asynchronous message when it has new information to share (block 1740), according to embodiments of the present invention. These asynchronous messages may include within them the new or updated data itself. When the BOA module 1110 receives one or more of these notifications, it updates the data model or data models that correspond to the particular device and/or information received (block 1742). For example, if new patient charting information is received from the patient charting module 1112 (which may be running on the patient charting device 108), the BOA module 1110 will update the patient charting data model to reflect the most recent data. The BOA module 1110 then refreshes its display (block 1744), which results in the currently displayed data model being replaced with the new data model immediately if any data in the data model was updated in block 1742. The data model update may then be sent to the BOA enterprise module which may reside on enterprise application server 128 (block 1746), which may result in an asynchronous message being generated to the BOA enterprise module (block 1748), according to embodiments of the present invention.

Some embodiments of the present invention include various steps, some of which may be performed by hardware components or may be embodied in machine-executable instructions. These machine-executable instructions may be used to cause a general-purpose or a special-purpose processor programmed with the instructions to perform the steps. Alternatively, the steps may be performed by a combination of hardware, software, and/or firmware. In addition, some embodiments of the present invention may be performed or implemented, at least in part (e.g., one or more modules), on one or more computer systems, mainframes (e.g., IBM mainframes such as the IBM zSeries, Unisys ClearPath Mainframes, HP Integrity NonStop servers, NEC Express series, and others), or client-server type systems. In addition, specific hardware aspects of embodiments of the present invention may incorporate one or more of these systems, or portions thereof.

Figure 18:
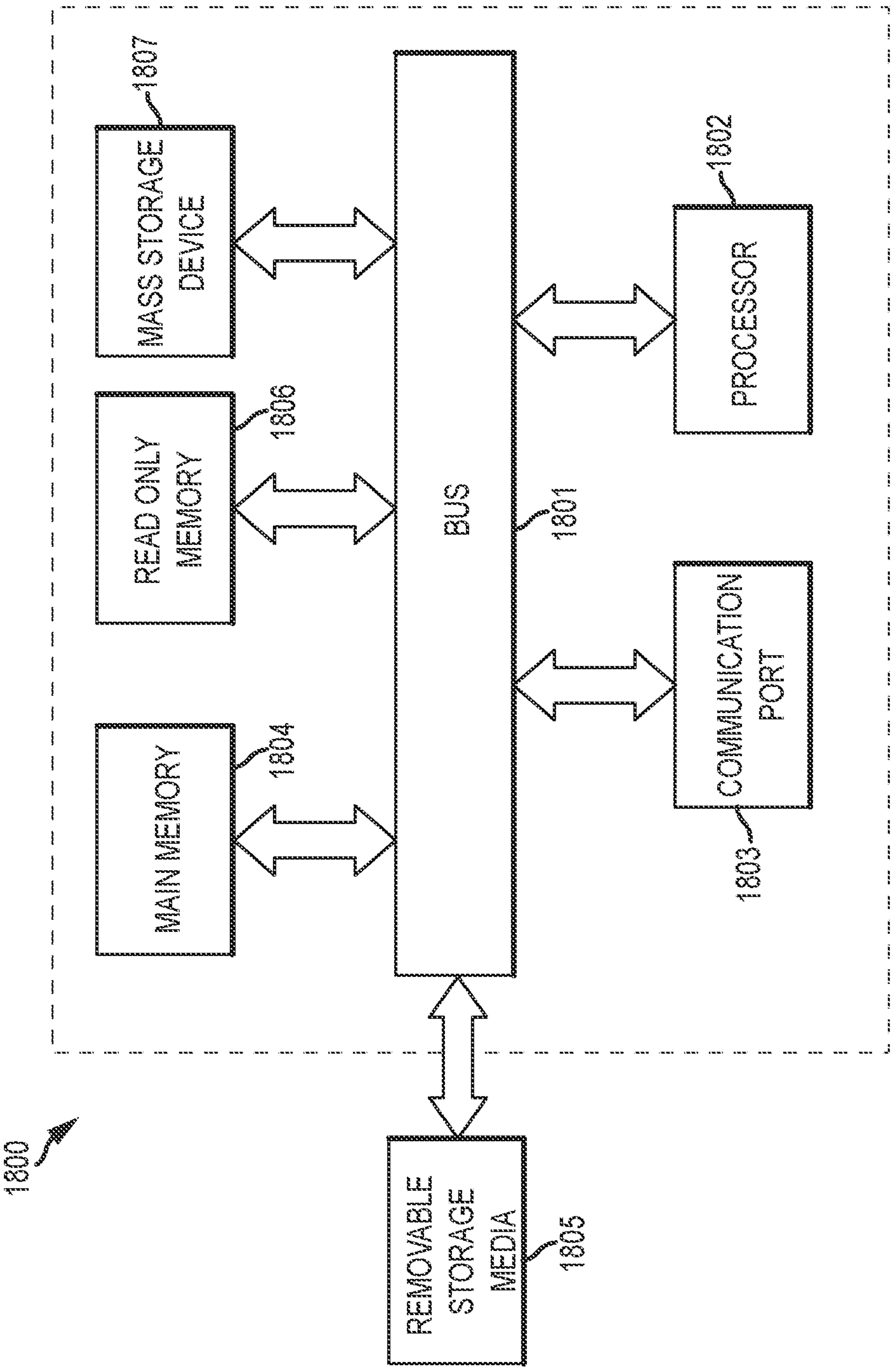
FIG. 18 illustrates an exemplary computer system, according to embodiments of the present invention.
Figure 19:
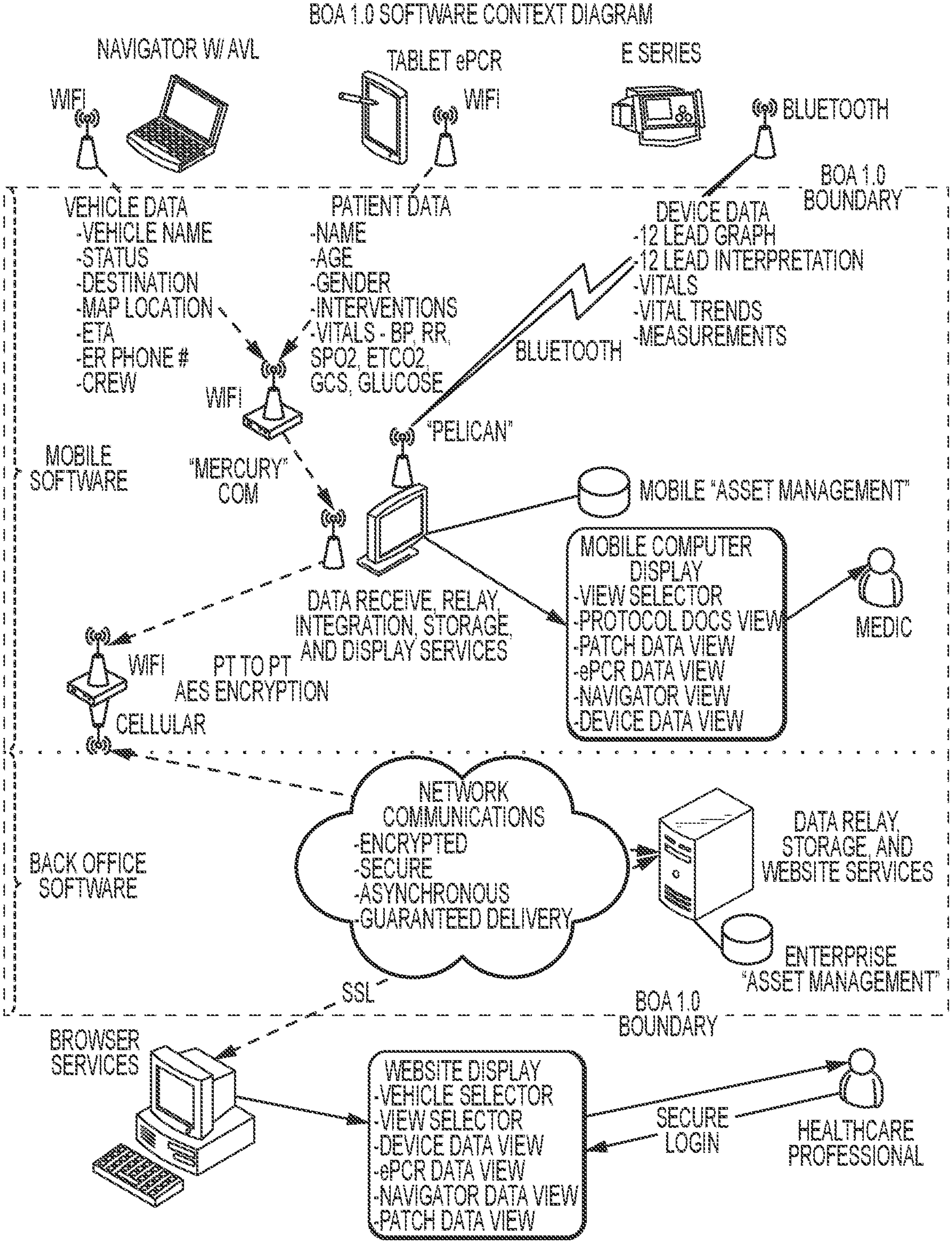
FIG. 19 illustrates a system for mobile and enterprise user real-time or clinical time display of medical information collected from multiple different EMS devices, according to embodiments of the present invention.

As such, FIG. 18 is an example of a computer system 1800 with which embodiments of the present invention may be utilized. According to the present example, the computer system includes a bus 1801, at least one processor 1802, at least one communication port 1803, a main memory 1804, a removable storage media 1805, a read only memory 1806, and a mass storage 1807.

Processor(s) 1802 can be any known processor, such as, but not limited to, an Intel® Itanium® or Itanium 2® processor(s), or AMD® Opteron® or Athlon MP® processor(s), or Motorola® lines of processors. Communication port(s) 1803 can be any of an RS-232 port for use with a modem based dialup connection, a 10/100 Ethernet port, or a Gigabit port using copper or fiber, for example. Communication port(s) 1803 may be chosen depending on a network such a Local Area Network (LAN), Wide Area Network (WAN), or any network to which the computer system 1800 connects. Main memory 1804 can be Random Access Memory (RAM), or any other dynamic storage device(s) commonly known to one of ordinary skill in the art. Read only memory 1806 can be any static storage device(s) such as Programmable Read Only Memory (PROM) chips for storing static information such as instructions for processor 1802, for example.

Mass storage 1807 can be used to store information and instructions. For example, hard disks such as the Adaptec® family of SCSI drives, an optical disc, an array of disks such as RAID (e.g. the Adaptec family of RAID drives), or any other mass storage devices may be used, for example. Bus 1801 communicably couples processor(s) 1802 with the other memory, storage and communication blocks. Bus 1801 can be a PCI/PCI-X or SCSI based system bus depending on the storage devices used, for example. Removable storage media 1805 can be any kind of external hard-drives, floppy drives, flash drives, (OMEGA® Zip Drives, Compact Disc-Read Only Memory (CD-ROM), Compact Disc-Re-Writable (CD-RW), or Digital Video Disk-Read Only Memory (DVD-ROM), for example. The components described above are meant to exemplify some types of possibilities. In no way should the aforementioned examples limit the scope of the invention, as they are only exemplary embodiments.

Embodiments of the present invention may be configured to achieve various other solutions in an emergency medical services environment. For example, the BOA device 104, in communication with the navigation device 110, may be configured to provide additional mapping and/or navigation information. The BOA device 104 may display status information about a hospital destination, and may indicate diversion or alternative destinations to direct the ambulance 101 to an appropriate destination, according to embodiments of the present invention. The BOA device 104 may also display characteristics about hospitals and/or other destinations, such as the hospital's capabilities (e.g. heart specialty, burn specialty), insurance accepted, patient capacity and current patient capacity status, according to embodiments of the present invention. The BOA device 104 may also be in communication with the enterprise workstation 122 of the hospital or other destination to permit preregistration or partial preregistration of the patient 116. According to embodiments of the present invention, a hospital without availability shows up for the ambulance driver 112 as not available. The BOA device 104 may be configured to display such information simultaneously with a map and/or during navigation, to facilitate destination selection. This information may be obtained over the network 120 from an enterprise server 126 or 128 and/or from an enterprise workstation 122 and/or from the navigation device 110, according to embodiments of the present invention.

The BOA device 104 may also be configured to communicate in various ways with the user, including with the EMS driver 112 and/or the EMS technician 114, according to embodiments of the present invention. For example, the BOA device 104 may be configured to provide audio prompts, alarms, scheduling, timing, and/or audio streams to EMS users. The BOA device 104 may be configured with Bluetooth® connectivity or capability, such that a user may connect or pair a unique Bluetooth® device with BOA 104 to receive audio information and/or to communicate voice prompts. An alarm may be configured to sound or to display visually upon a triggering event, for example upon receipt by the BOA device 104 of an asynchronous event signal from a sensor indicating that a detected parameter is outside an acceptable range or value, according to embodiments of the present invention. Audio and/or visual cues may be used to alert a user to a particular dosage schedule, for example beeping when a certain amount of time has elapsed since a first administration of a drug. Such alarms and/or schedules may be set or customized by the users, or may be selected from a predetermined set of alarm and scheduling options, according to embodiments of the present invention.

According to embodiments of the present invention, the BOA device 104 may provide role-based data and/or audio streams; for example, a technician administering CPR may receive audio and/or visual information about the patient's cardiac condition, but the BOA device 104 may filter out other information such as mapping and/or routing information for that user. Private, customized feedback and/or information may be provided to EMS users based on their roles, according to embodiments of the present invention.

The BOA device 104 may further provide decision support for an EMS technician, according to embodiments of the present invention. Based on information entered by the technician 114 (e.g. via a patient charting device 108) and/or information received from a patient monitoring device 106, BOA device 104 may compare the information with internal or external databases to display or otherwise convey a differential diagnosis, and/or predictive diagnosis (e.g. based on vectors or EKG information), according to embodiments of the present invention. For example, the BOA device 104 may present the EMS technician 114 with a decision matrix based on symptoms and/or responses to treatments to help the EMS technician 114 determine, for example in an interactive format, a potential diagnosis. The BOA device 104 may provide protocols or links to protocols based on the information received, either from the technician 114 or from one of the devices with which it is in communication.

In one embodiment, the data for the patient's history may be entered via the BOA device 104 with patient physiological measures via the monitor of BOA device 104. As the differential diagnosis requires both patient history, patient examination findings, and measures of the patient's physiological state via such monitoring as ECG, capnography and pulse oximetry, these data elements are integrated into a user interface that automatically or semi-automatically integrates the various data elements on a single differential diagnosis screen within the application on the BOA device 104, according to embodiments of the present invention. The interface of BOA 104 begins by asking the rescuer to choose from a list of common presenting symptoms or complaints by the patient, e.g. dyspnea or respiratory distress. The information such as on the screens illustrated in FIGS. 26-28 (taken directly from Am Fam Physician 2003; 68:1803-10, which is incorporated by reference herein) and FIG. 29 (taken directly from the Collier County Common Medical Protocol, revised Feb. 1, 2008), provides a structured approach for rescuers to obtain information. As patient history and physical examination findings are entered into the BOA device 104, the differential diagnosis page may gradually narrow down the possible diagnoses. Heart sound measurement and detection may be incorporated into the monitoring device 106 for the detection of S3 and S4 heart sounds and automatically narrow the differential, or suggest for the rescuer to confirm agreement with the software diagnosis, of heart failure or pulmonary edema. A flowchart for incorporating heart sounds is shown in FIGS. 26-29. Pulse oximetry and capnography are also very helpful measures and may be automatically incorporated into the algorithm for more accurate diagnosis.

In one embodiment, rescuers may be able to simply touch the cursor to the history or physical exam findings listed as possible from the screen-displayed lists of FIGS. 26-29, thereby minimizing unnecessary keying inputs. At the bottom of each list of possible findings or history is a data entry position for "Other", for those findings or history which are not normally consistent with the presenting condition. In one embodiment, these additional findings, history or physiological measurements can be compared with a larger differential diagnosis database to suggest other possibilities to the rescuer based on a calculated probability or if the other possible causes have been ruled out, according to embodiments of the present invention.

In much the same way that twelve-lead data and other BOA 104 device data may be sent to an enterprise environment 102 and displayed and/or retrieved on an enterprise workstation 122 or web-based environment, the BOA device 104 may also be configured to receive, display, and/or store similar information from an enterprise environment 102, according to embodiments of the present invention. For example, in a situation in which a patient is being transported from one hospital to another to receive specialized care, the hospital may send to the BOA device 104 information about the patient's vitals and/or health history and/or physician recommendations. Alternatively, the hospital may grant electronic authorization for the remote EMS technician to query its database or databases where such information is kept, to enable the EMS technician 114 to select, using the BOA device 104 interface, which and how much information he would like to receive. In this way, technicians in an ambulance 101 can see what is happening to a patient at the hospital, for example.

The BOA device 104 may also include speech recognition software and/or text-to-speech software, according to embodiments of the present invention. As such, the BOA device 104 may provide an audio signal that reads text or numeric data received from one or more devices, to convey the data to the EMS technician 114 audibly, such that the EMS technician 114 need not divert visual attention from the patient or from another task, according to embodiments of the present invention. The BOA device 104 may also recognize voice command prompts, to enable the user to operate the BOA device 104 by voice instead of having to divert manual attention from the patient or the task at hand, according to embodiments of the present invention.

The BOA device 104 also be configured to retrieve audio data stored on a device, such as a patient monitoring device 106, to help the EMS technician 114 in treatment or diagnosis, and/or for storage, technician evaluation, quality control, or later playback. For example, the patient monitoring device 114 may be a defibrillator that records a continuous audio stream; the BOA device 104 may access the continuous audio stream and permit selective play back of certain portions and/or transmit the audio stream or audio file for remote access or storage, according to embodiments of the present invention. The BOA device 104 may also be configured to receive audio information from a patient monitoring device 106 or other device even before the EMS technician 114 has reached the patient, to help the EMS technician 114 to prepare for the scene.

The BOA device 104 may be configured to connect with a video monitoring device, for example a webcam, or a standalone video camera, and/or a video capture device that is mounted on or part of another device to which the BOA device 104 connects, according to embodiments of the present invention. For example, a video or still camera mounted in the back of an ambulance 101 may provide visual data to BOA 104 for storage and/or transmission and/or retransmission to the enterprise environment 102 and/or the administration environment 103. Such a video feed may permit a physician waiting at a hospital to view the patient's status before the patient arrives, for example.

With an ability to connect with and interface multiple EMS-related devices, both clinical and non-clinical, and aggregate such EMS-information (both clinical and non-clinical) from multiple devices, the BOA device 104 may also be configured for inventory monitoring and control. For example, the BOA device 104 may be communicably coupled with a bar code scanner, a radio frequency identification ("RFID") receiver or transceiver, or other inventory monitoring device. The BOA device 104 may maintain or communicate with a database that tracks a particular set of inventoried items, whether they be medical devices, supplies, drugs, personnel, or the like.

For example, the BOA device 104 may include a database that tracks the inventory of devices, supplies, and drugs on board a particular ambulance 101. When a new device is placed on the ambulance 101, the new device is equipped with a tag or bar code or some other unique identifier, and the BOA device 104 may be configured to automatically sense, or to be instructed to sense (e.g. by scanning a bar code with the bar code scanner), the presence of a new inventory item. The BOA device 104 may also prompt the user with a status update request, for example: new item, item being removed, item being dispensed, item destroyed, item transferred. Hence, at the beginning of an ambulance 101 shift, the crew may query the BOA device 104 to display the inventory of devices, supplies, and/or drugs on board, and may supplement the inventory for any deficient item. When a drug is administered, it may be scanned into the BOA device 104 system with an indication that it has been dispensed and should be replaced. At the end of a shift, the crew may check the inventory via the BOA device 104 and restock necessary supplies and/or transmit the inventory situation to a third party for any appropriate restocking, monitoring, and/or verification activity.

Such inventory information may also be conveyed by BOA 104 for remote use and/or storage. For example, a defibrillator patient monitoring device 106 may be checked out to each crew of each ambulance 101, and this information may be sent by BOA device 104 through network 120 to the enterprise storage server 126, which may aggregate such information across multiple ambulances 101. A shift supervisor using a remote enterprise workstation 122 may query such database to determine which defibrillators are out in the field on which ambulances 101, according to embodiments of the present invention. In this way, the BOA device 104 may auto-upload inventory information to a central system.

The BOA device 104 may also be configured to connect with devices (clinical and/or non-clinical) that track EMS technician 114 and patient 116 safety, according to embodiments of the present invention. For example, the BOA device 104 may be configured to connect with accelerometer and/or tire pressure sensors, and/or other vehicle-relate sensors to track driving conditions, driving behavior, safety level, and/or event occurrences, according to embodiments of the present invention. According to one embodiment of the present invention, the BOA device 104 may be configured to connect with a breathalyzer device, which may be used to sense and/or estimate the blood alcohol content of the driver and/or patient. The BOA device 104 may collect such data and display it to the user in a feedback format, and/or may send such data through the network 120 for storage and/or remote evaluation, according to embodiments of the present invention. The BOA device 104 may also monitor a vehicle's maintenance schedule and alert the user when maintenance is needed or recommended, according to embodiments of the present invention.

Due to its connection with the network 120 and also with other devices 106, 108, 110, the BOA device 104 may also serve as an ambulance headquarters and/or a type of "repeater" in a trauma or disaster situation, according to embodiments of the present invention. For example, the BOA device 104 may be configured to connect with multiple devices including devices outside the ambulance 101 and/or in a different ambulance 101, to permit the BOA device 104 user to view and manage response treatments, for example. Such a configuration also permits data from multiple devices (e.g. multiple defibrillators or other patient monitoring devices) to be conveyed through the network 120 to an enterprise environment 102 and/or administration environment 103, according to embodiments of the present invention. In another example, a single ambulance 101 equipped with a BOA device 104 system as described above may be deployed to a disaster or trauma situation, and the BOA device 104 may be connected to and aggregating information from multiple patient monitoring devices 106. A supervisor or situation manager may use the BOA device 104 to monitor treatment status, prioritize patient medical needs, transmit relevant information to selected outside caregivers, hospitals, and/or treatment centers, and to distribute resources accordingly.

According to some embodiments of the present invention, the BOA device 104 is configured to perform diagnostics on and/or to initiate self-diagnostics for devices with which it is connected. The BOA device 104 may also be used for training and/or education of EMS technicians 114, by making downloaded protocols available for display, and/or by simulating a medical emergency (e.g. simulating the device feeds from multiple clinical and non-clinical devices during a medical emergency or transport).

According to some embodiments of the present invention, the BOA device 104 provides a visual indication of whether its connection with the navigation device 110 (or other predetermined device) is online or offline. According to some embodiments, the user can select to view historical rather than current patient information; for example, the user may select to view thumbnails of previous twelve-leads, and can send a collection of twelve-lead data snapshots to an enterprise environment 102 (e.g. a hospital), each with a unique serial number, for example. The enterprise user 124 may also view the patch notes from the BOA device 104, so that the EMS technician 114 need not convey them telephonically, according to embodiments of the present invention.

The BOA device 104 may also include a drop-down menu interface, listing each device to which the BOA device 104 is connected and its connection status, according to embodiments of the present invention. The BOA device 104 may also be connected with a biometric device such as a fingerprint reader or a retinal scanner, or a non-biometric device such as a keypad, to assist in verifying the identity of a patient and/or in authorizing access to patient medical records. Such records may be stored in remote databases and/or stored by different entities, for example.

FIGS. 20-23 illustrate an EMS communication interface device 2000, configured to facilitate communication between a patient monitoring module 1102 and a device adapter/communication interface 1104 (see FIG. 11). Not all patient monitoring devices 106 include the hardware necessary for certain kinds of communication (e.g. wireless communication), either with BOA device 104 or with other enterprise environments 103. An EMS communication interface device 2000 may be added as an accessory to the patient monitoring device 106 in order to supplement its communication capability, as well as provide additional functionality, according to embodiments of the present invention.

The EMS communication interface device 2000 may be configured to interface with the patient monitoring device 106 via an existing hardware interface, such as, for example, via a PCMCIA card slot, a USB slot, or the like, according to embodiments of the present invention. The following example illustrates an EMS communication interface device 2000 that interfaces with a patient monitoring device 106 via a PCMCIA card slot in the device 106, according to embodiments of the present invention.

Figure 20:
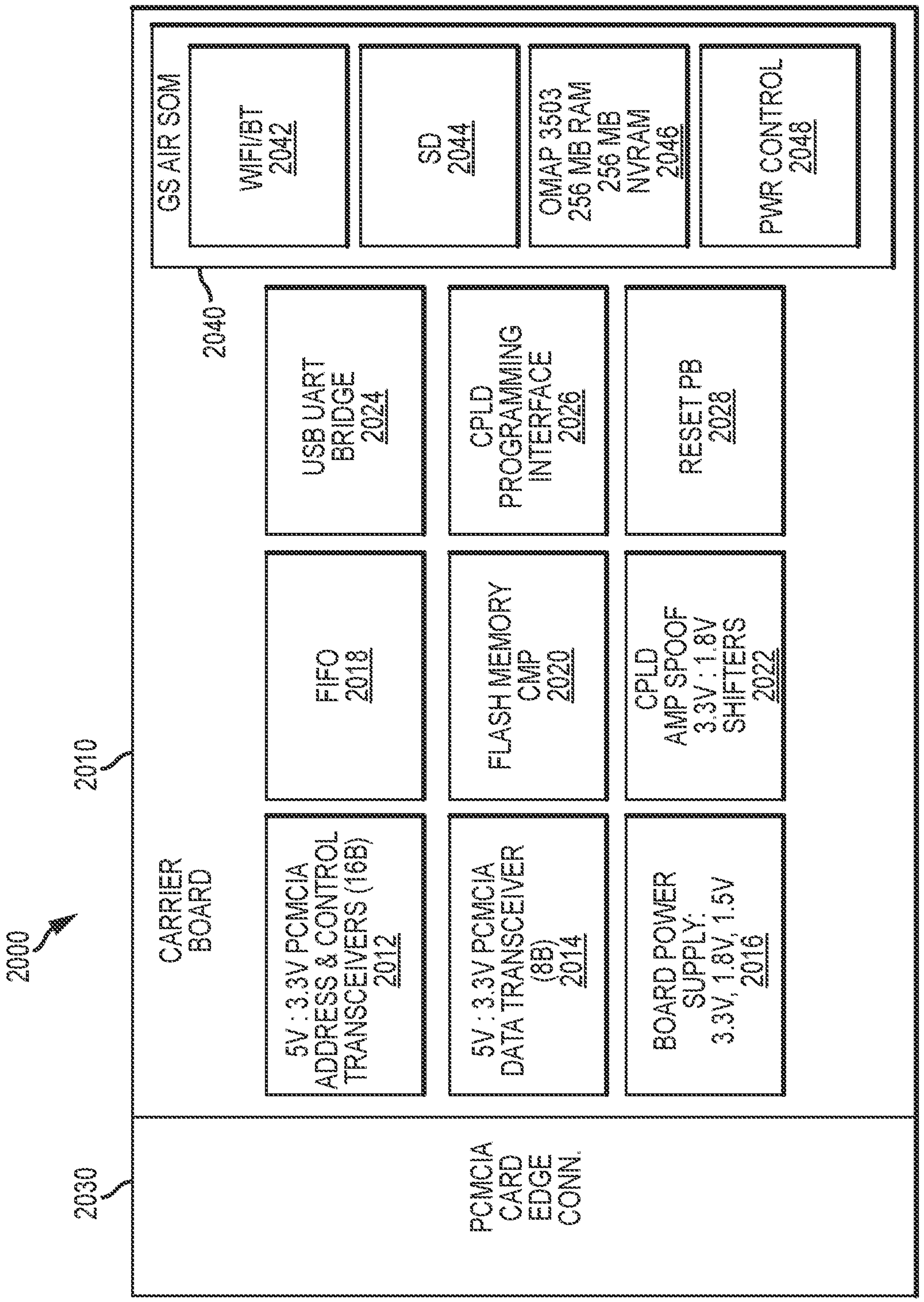
FIG. 20 illustrates a carrier board design for an EMS communication interface device, according to embodiments of the present invention.

FIG. 20 illustrates a carrier board 2010 design for an EMS communication interface device 2000, according to embodiments of the present invention. The carrier board 2010 may be a custom carrier board for a systems-on-module ("SOM") hosting of various subsystems. The carrier board 2010 may host a PCMCIA edge connector 2030, PCMCIA address and control transceivers 2012, PCMCIA data transceivers 2014, a board power supply 2016, a first-in-first-out ("FIFO") co-processor input memory buffer 2018, a flash memory common memory plane ("CMP") 2020, a complex programmable logic device ("CPLD") attribute memory plane ("AMP") spoof shifter 2022; a universal serial bus ("USB") universal asynchronous receiver-transmitter ("UART") bridge 2024, a CPLD programming interface 2026, and a reset push button 2028. The power supplies for 3.3V, 1.8V, and 1.5V levels may be derived from PCMCIA 5V and possibly 12V inputs, according to embodiments of the present invention. Device 2000 may further include a USB 2.0 port.

The carrier board 2010 may also include a SOM coprocessor subsystem 2040 such as, for example, a Gumstix Overo Air SOM or a LogicPD Torpedo SOM. SOM 2040 may include a Bluetooth ("BT") radio and/or antenna and/or a WiFi (e.g. 802.11a/b/g/n) radio and/or antenna 2042. The 802.11 a/g subsystem may be initialized and configured during boot, and may also be configured via terminal session, according to embodiments of the present invention. SOM 2040 may also include a storage device 2044, such as, for example, a removable micro SD storage/memory slot. A micro SD card may be used in such a slot as random access storage as well as a source of the boot strap code to initialize the co-processor subsystem 2040. SOM 2040 may also include a power management integrated circuit ("IC") 2048, such as, for example, a Texas Instruments TPS65950 integrated power management IC. SOM 2040 may also include a processor 2046 such as, for example, a TI Open Multimedia Applications Platform ("OMAP") 3503 processor with 256 MB of random access memory ("RAM") and 256 MB of non-volatile RAM ("NVRAM") in a package-on-package ("POP") package. The coprocessor subsystem 2040 may be communicably coupled to the carrier board 2010 via dual 70-pin headers, according to embodiments of the present invention. The carrier board 2010 may also include a Joint Test Action Group ("JTAG") interface for programming, according to embodiments of the present invention.

The device 2000 may include CPLD firmware, such as, for example, Actel Igloo Nano AGL250V2-VQG100_0. Such CPLD firmware may govern linear flash ("LF") control signals for read/write operations, may govern FIFO control signals for write and read operations in a manner of a FIFO dual-ported implementation, and may employ level shifted address and data buses for LF, FIFO, and the OMAP, according to embodiments of the present invention. The device 2000 may include an operating system, such as, for example, OE 2.6.x Open Embedded Linux. The device 2000 may employ the C# Common Language Runtime (2.6.2), for example the Mono common language runtime ("CLR"), according to embodiments of the present invention. The device 2000 may include persistent data storage using SQLite software library, according to embodiments of the present invention. The device 2000 may perform asset management patterned data storage for framed data, and/or asset management patterned services for parameterized frame retrieval, according to embodiments of the present invention. The device 2000 may accomplish WiFi communications using User Datagram Protocol/Internet Protocol ("UDP/IP") for streaming data output, a .NET remoting service bus, and/or a .NET remoting eventing bus, according to embodiments of the present invention.

Figure 21:
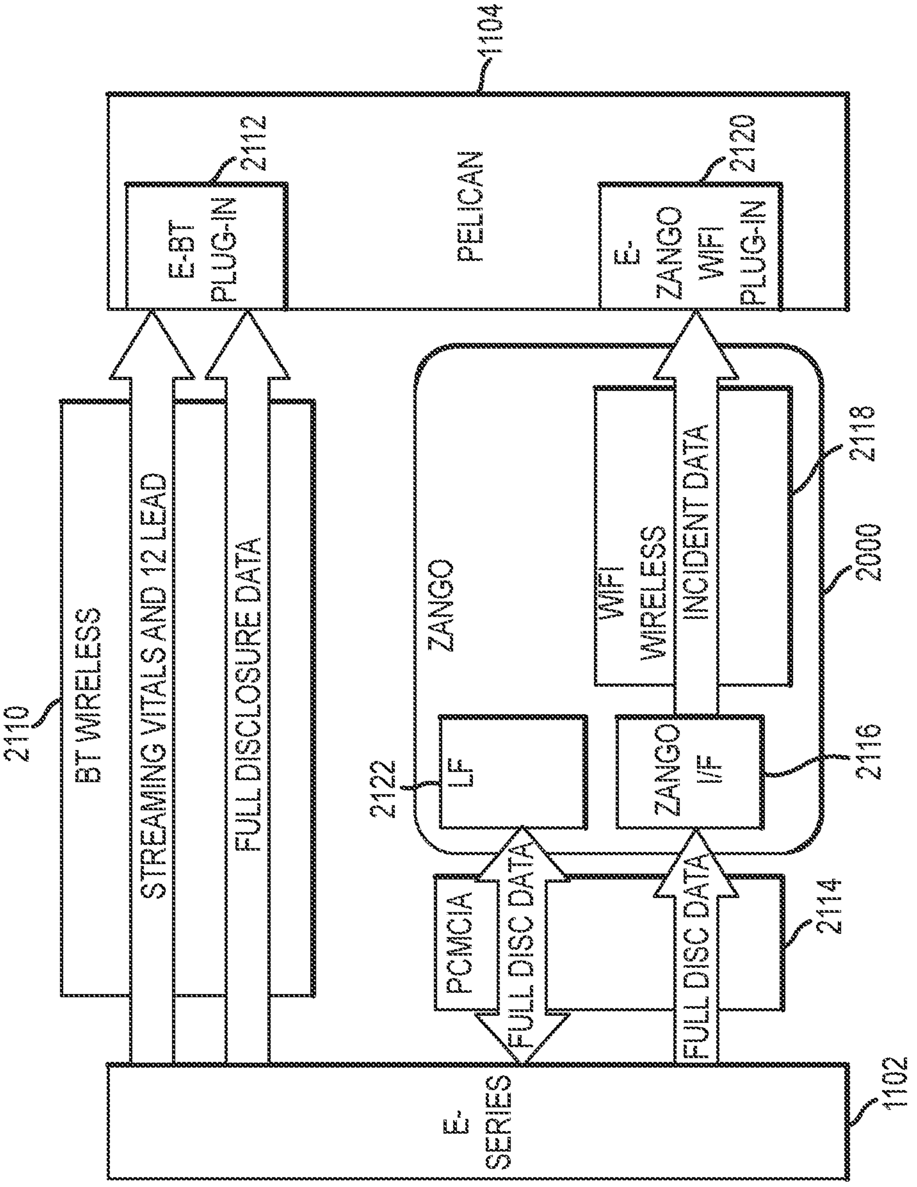
FIG. 21 illustrates a system overview for an EMS communication interface device, according to embodiments of the present invention.

FIG. 21 illustrates a system overview for an EMS communication interface device 200, according to embodiments of the present invention. A patient monitoring module 1102 processes and sends patient monitoring data. The patient monitoring module 1102 may be implemented by a Zoll E-Series Defibrillator, according to embodiments of the present invention. Such patient monitoring module 1102 is configured to transmit streaming patient vital signs and twelve lead information, as well as full disclosure data, over a BT wireless connection 2110, to a BT plug-in 2112 that is part of a device adapter 1104, according to embodiments of the present invention. As used herein, the term "Full Disclosure Data" means all data recorded by a patient monitoring device 106, and includes, without limitation, patient vital signs, twelve-lead data, audio information, ECG information, lead type, gain, defibrillator shock information, system mode, paddle type, heart rate alarm status, heart rate, configuration information, code marker information, non-invasive blood pressure measurements, patient name, patient identification, biphasic defibrillator data, invasive blood pressure information, invasive blood pressure waveform data, temperature data, $SpO_2$ information, $SpO_2$ waveform, sample number information, accelerometer information, accelerometer waveform, impedance waveform, CPR field data, APLS waveform, and/or APLS compression detection.

A WiFi wireless connection has a much higher bandwidth for the transfer of information than a BT wireless connection. However, in some cases, the patient monitoring device 106 on which the patient monitoring module 1102 runs may not include WiFi capabilities, but it may include a personal computer memory card international association ("PCMCIA") card slot with a PCMCIA interface 2114. A PCMCIA card may also be referred to as a PC card. The EMS communication interface device 2000 may be plugged in to the PCMCIA card slot 2114. The device 2000 may include a linear flash memory card 2122 or other memory element for recording full disclosure data from the patient monitoring device 106, according to embodiments of the present invention. The memory card 2122 may be used to replicate all existing memory card functionality of the patient monitoring device 106, by storing in linear flash memory 2122 all data written to the patient monitoring device 106 data slot, by permitting a utility mode user-initiated retrieval of stored data from linear flash memory 2122, and/or by permitting a utility mode user-initiated erasure of the linear flash memory 2122, according to embodiments of the present invention.

The full disclosure data stream from the patient monitoring module 1102 may also be received through the PCMCIA slot 2114 by an EMS communication interface module 2116, which transforms the full disclosure data into incident data, and provides the incident data over a WiFi connection 2118 to a WiFi plug-in 2120 that is part of the communication interface 1104, according to embodiments of the present invention.

Figure 22:
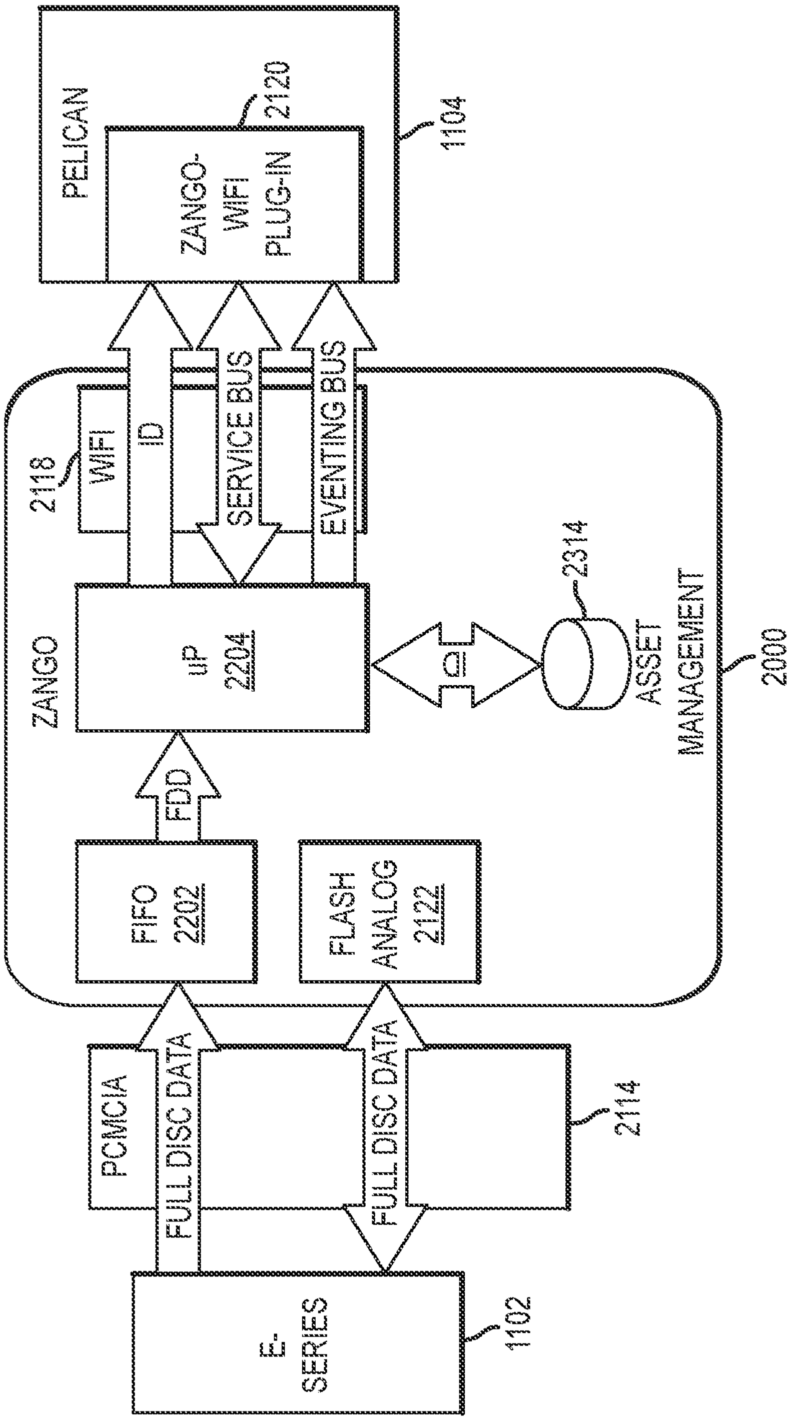
FIG. 22 illustrates another system overview for an EMS communication interface device, according to embodiments of the present invention.

FIG. 22 illustrates another system overview for an EMS communication interface device 2000, according to embodiments of the present invention. As illustrated in FIG. 21, full disclosure data is recorded in a memory module 2122, for example a flash linear analog memory module 2122, according to embodiments of the present invention. The flash analog module 2122 may be read, written, and/or erased by the patient monitoring module 1102 similarly to the fashion in which any memory element permanently associated with the patient monitoring device 106 may be read, written, and/or erased by via the device 106, according to embodiments of the present invention. This may be accomplished by using a utility mode of the device 106, for example. As such, the flash analog 2122 is not interfaced to the SOM (e.g. to microprocessor 2204), but only to the patient monitoring module 1102 in write/read/erase fashion.

According to embodiments of the present invention, the flash analog memory 2122 is designed to resemble the linear flash card that is normally associated with, and which may be embedded within, the patient monitoring device 106. Certain information may be stored in a non-volatile memory area, for example in the attribute memory plane, and certain other information may be stored in the first series of bytes of the common memory plane, to make the memory 2122 resemble the internal memory of the patient monitoring device 106. The communications interface 2116 may be a FIFO buffer 2202, which may receive full disclosure data from the patient monitoring module 1102 via the PCMCIA interface 2114, and pass the full disclosure data to a microprocessor 2204. The FIFO 2202 is uni-directional from the patient monitoring module 106 to the microprocessor 2204, according to embodiments of the present invention. Incident data sent may also be persisted in the asset management database 2314.

According to embodiments of the present invention, the FIFO buffer 2202 and/or the flash analog memory module 2122 are hardware-only solutions that function even when the SOM 2040 is non-operational. This functionality permits data protection in the case in which the SOM 2040 is not functional, and permits data buffering for the SOM 2040 to initialize (e.g. to boot and start the EMS communication interface services), according to embodiments of the present invention. During therapy mode data capture to the card 2122, if the SOM 2040 were to be disabled, device 106 data would not be lost, according to embodiments of the present invention. This also permits users who have been trained on utility modes of a patient monitoring device 106 related to the storage of data on a memory module to continue using such utility modes, even with the data being stored on memory module 2122 instead of a memory module internal to device 106, according to embodiments of the present invention.

Using a plug-in 2120 that is part of the communication interface 1104, incident data ("ID") may be streamed from the microprocessor 2204 over a WiFi connection 2118. Such information may be received and displayed by BOA device 104, for example, and may be displayed in real time and/or in clinically significant time (e.g. with a delay not larger than that which permits a medically accurate and timely observation, diagnosis, and/or treatment decision to be made). According to embodiments of the present invention, the incident data may be streamed on a BOA device 104 with no more than a one-second delay. For example, twelve-lead data generated by a defibrillator patient monitoring device 106 may be updated at least once each second, according to embodiments of the present invention.

The microprocessor 2204 may also be programmed to generate asynchronous (e.g. event based) notifications via an eventing bus, over the WiFi connection 2118, according to embodiments of the present invention. For example, if a patient vital sign falls outside of present parameters, the microprocessor 2204 may be programmed to send an alarm event via eventing bus across the communication interface 1104.

In addition, the microprocessor 2204 may be programmed to permit a two-way service bus/service interface, to permit the requesting of incident data related specific incidents, according to embodiments of the present invention. For example, after a treatment incident, the user may request, via a service bus, from microprocessor 2204 all information associated with the particular incident (using a unique incident identifier, such as a case number, patient name, or the like). The microprocessor 2204 would then query the asset management module 2314 and retrieve any records associated with the particular incident, and send them back out through service bus, according to embodiments of the present invention. In this way, users may retrieve specific incident data rather than having to download all of the card file data (which in many cases will relate to multiple incidents, or information beyond the specific subset of information sought). This is made possible by the conversion of full disclosure data into incident data by the microprocessor 2204 prior to storage and/or forwarding. In some cases, users may wish to request all data stored by asset management module 2314, which would be a similar operation to the request for the card file directly from the patient monitoring module 1102.

Figure 23:
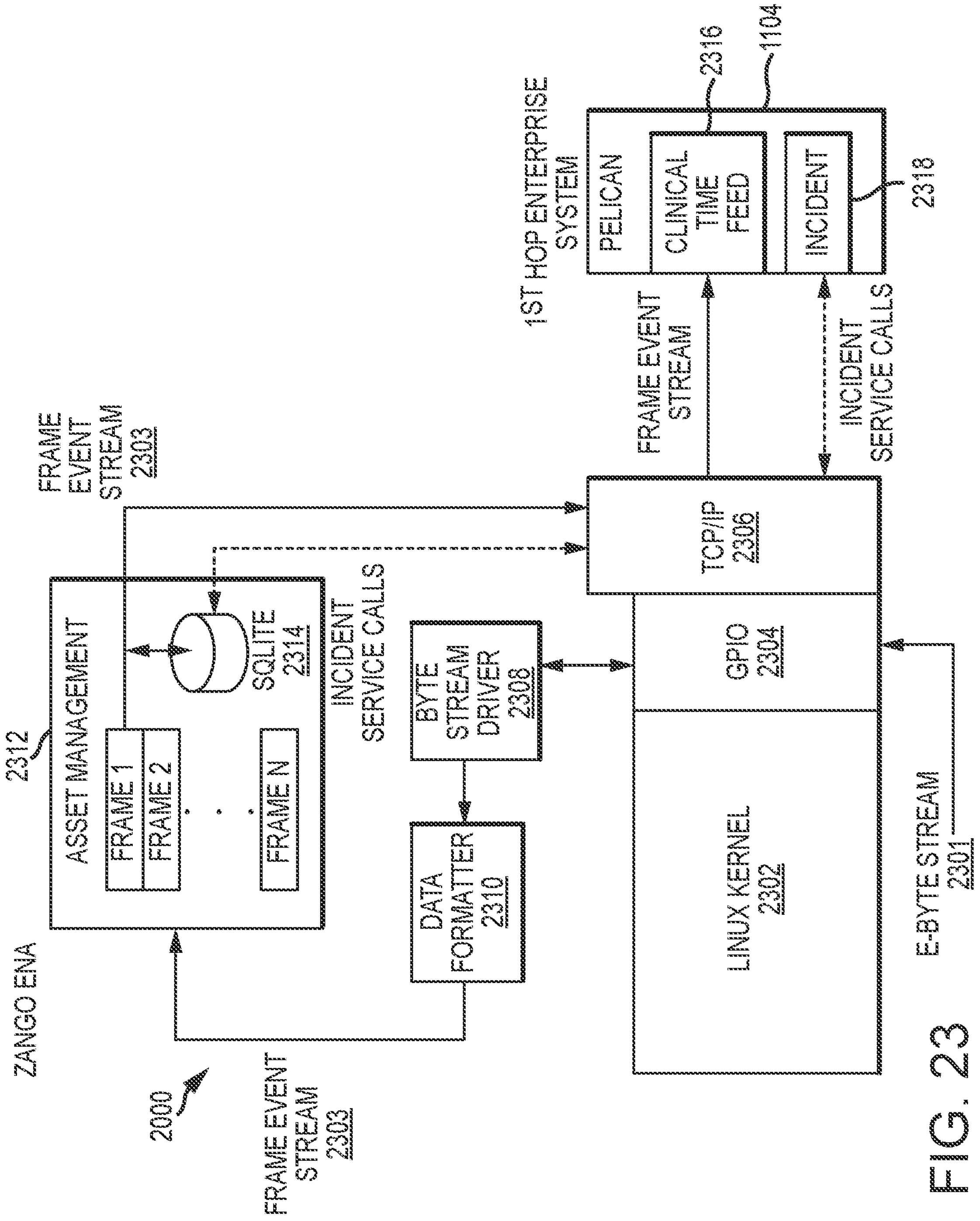
FIG. 23 illustrates a software logic diagram for an EMS communication interface device, according to embodiments of the present invention.

FIG. 23 illustrates a software logic diagram for an EMS communication interface device 2000, according to embodiments of the present invention. A Linux Kernel 2302 may include a general purpose input/output ("GPIO") module 2304 configured to receive the data stream (e.g. the full disclosure data) 2301 from the patient monitoring device 106. The data stream 2301 is interfaced to the system 2000 through the FIFO module 2202 which is controlled with several GPIO 2304 lines, according to embodiments of the present invention. The FIFO is read to the SOM using GPIO status, control and eight bits of data, according to embodiments of the present invention. The byte stream driver 2308 may be implemented in user space rather than a device driver to facilitate debugging, in some embodiments. The byte stream driver 2308 may keep the FIFO 2202 drained by monitoring the FIFO 2202 empty flag (which may be polled as opposed to interrupt driven for debugging efficiency in one embodiment).

Bytes read from the FIFO by the byte stream driver 2308 are re-assembled as blocks similar to those delivered by the patient monitoring device 106 and framed in the data formatter 2310, according to embodiments of the present invention. This results in a frame event stream 2303 from the data formatter 2310. The frame event stream is then sent to an asset management module 2312, which saves the frames to the database 2314 and forwards them out the WiFi channel to the TCP/IP module 2306 of the Linux Kernel 2302. According to some embodiments of the present invention, the frame event stream 2303 is sent over the WiFi connection via an encrypted UDP broadcast, so that it may be received by a wide range of clients (e.g. an iPhone may be configured to receive the UDP broadcast). The frame event stream 2303 may also be received by a clinical time feed plug-in 2316 of the communications interface module 1104, according to embodiments of the present invention.

Asynchronous requests for incident data stored in the database 2314 may be made by authorized external clients, such as via an incident plug-in 2318 of the communications interface module 1104, according to embodiments of the present invention. Such incident service calls are shown in dashed lines in FIG. 23. Although database 2314 is shown as an SQLite database, one of ordinary skill in the art will appreciate, based on the disclosure provided herein, that other database formats may be employed by asset management module 2312, according to embodiments of the present invention.

According to embodiments of the present invention, the byte stream is formatted by data formatter 2310 into blocks of data resembling device 106 data blocks, and these full data blocks are broadcast in a WiFi format upon construction (e.g. as a block is made, it is sent over the WiFi interface). According to embodiments of the present invention, the asset management module 2312 frames the byte stream into consistent blocks of time, for example one second per frame, and each frame is saved into the asset management patterned data storage (e.g. database 2314).

Although FIGS. 21-22 show full disclosure data as two separate feeds, a single full disclosure data feed may be bifurcated and sent to both the flash analog module 2122 and the FIFO 2202 simultaneously, according to embodiments of the present invention.

A user may query the device 2000 to request health information, for example, running time, exceptions detected, and other information from the patient monitoring device 106, according to embodiments of the present invention. A user may also request specific incident-based data from the device 2000; for example, a user may send a query that says "send all of the cases," or "send data relating to a specific case" or "send all twelve-lead data from a specific case." The device 2000 may also stream delivery of case data so as to permit multiple authorized receivers (e.g. multiple BOA devices 104) to obtain the data simultaneously, according to embodiments of the present invention. According to some embodiments of the present invention, device 2000 facilitates data sharing between the patient monitoring device 106 and the enterprise environment 103.

On power up, the device 106 interrogates the occupant of the PCMCIA slot 2114 to ascertain if a valid linear flash card 2122 is present. The validity test may consist of reading a series of bytes from the LF AMP and validating the values against sets of acceptable cards or an acceptable card. If a valid card is found, the device 106 reads a series of bytes from the CMP to test for validity and to determine if the card has been "formatted" according to the requirements of the device 106. In the absence of such a series of bytes, the device 106 may write such information to the card 2122, according to embodiments of the present invention. Once the card 2122 is validated, the device 106 begins to write the device data to the LF card 2122 as byte streams that are formatted into blocks as described, above.

Although the device 2000 is depicted as interacting with device 106 in a one-way fashion, the device 2000 may also be configured to interact bi-directionally with device 2000. For example, the device 2000 may be configured to provide a WiFi user interface similar to the user interface observed directly on the patient monitoring device 106, to permit total or partial remote control of the patient monitoring device 106, according to embodiments of the present invention.

Packaged in a PCMCIA type x housing, each card 2010 contains a connector 2030, an array of flash memories packaged in thin small outline packages ("TSOP") and card control logic. The card control logic provides the system interface and controls the internal flash memories as well as the input FIFO to the SOM, according to embodiments of the present invention. Level shifters are present to adapt PCMCIA logic voltages to card logic voltages.

Card logic voltages of 3.3V, 1.8V, and 1.5V may be derived from the PCMCIA VCC voltage (TTL, +5V, possibly +12V). A single stage for 3.3V and 5V conversions is built using three discrete transceivers. A CPLD is used to perform 3.3V and 1.8V conversions.

| Part | Logic Voltages | Power | Notes |
|---|---|---|---|
| J1 | +5 V | +5 V, +12 V | 2X34 PCMCIA connector |
| U5, U6, U7 | +5 V:+3.3 V | +5 V, +3.3 V | Level Shifters |
| U3 | +3.3 V | +3.3 V | Flash Memory |
| U7 | +3.3 V | +3.3 V | FIFO |
| U1 | +3.3 V:+1.8 V | +3.3 V, +1.8 V | CPLD |
| MCU | +1.8 V | +4.0 V | OMAP SOM |

Data enters FIFO at 3.3V from the PCMCIA byte stream. Reading the FIFO is clocked an 8 bit byte at a time on the read clock shifted between 3.3 and 1.8 to OMAP, through the CPLD. OMAP control and status interface bits may be converted in a similar fashion. Each carrier card 2010 may have a USB2.0 port. OMAP UART signals are connected to a USB to UART serial bridge 2024, according to embodiments of the present invention.

A JTAG interface for programming the CPLD may be provided. A 2×34, A and B sided PCMCIA Connector (J1) may be used, that inter-connects I/O, status and power signals between the device and the card, according to embodiments of the present invention. For the device signals that the card interface is interested in, there is a group of three transceivers (U5, U6, and U7) that inter-convert PCMCIA voltage (VCC) and board voltage (3V3), according to embodiments of the present invention. Device 2000 is interested in 26 address bits, 8 data bits, and 6 control signals that are intended to be level-shifted, according to embodiments of the present invention. U5 and U6 are uni-directional 16b input shifters from device to card for address and control information, according to embodiments of the present invention. U7 is a bi-directional 8b level shifter for 8 bits of data.

According to embodiments of the present invention, the device 2000 reads and writes data through this interface to LF memory. U5 shifting 16 address bits [PCA0:PCA15] to [A0:A15]. U6 shifting 10 address bits [PC16:PC25] to [A16:A25], and 6 control signals {PC_REGn, PC_RESET, PC_CE1n, PC_CE2n, PC_OEn, PC_BWEn} to {REGn, RESET, CE1n, CE2n, OEn, BWEn}.

| Sig | Description | Active |
|---|---|---|
| REGn | Attribute Memory Select | Low |
| CE1n | Card enable 1 | Low |
| CE2n | Card enable 2 | Low |

-continued

| Sig | Description | Active |
|---|---|---|
| OEn | Output enable | Low |
| BWEn | Write enable | Low |
| RESET | Reset | High |

[PCD0:PCD7] 8 data bits (U2). Address shifters may be input only, in which case the card does not generate address information to the device 2000, only outbound addressing (device to card) is exposed, according to embodiments of the present invention. The data shifter is bi-directional as the device can read and write data to and from the card, according to embodiments of the present invention. U5 shifts 16 bits of address and U6 shifts 8 control signals and the upper 8 bits of the address and control signals from PCMCIA VCC to 3V3.

Device 2000 is configured to permit streaming data transmission via WiFi during therapy mode operations of the device 106, as well as post-case upload of device data. The device 2000 has hardware components as well as programmable elements using both firmware and embedded software, including an embedded operating system as described, above. According to some embodiments, the EMS communication interface device 2000 is thicker than a standard Type III PCMCIA card.

An embodiment of the present invention may include one of more of the following features and/or characteristics:

- The carrier may be a PCMCIA card
- The carrier may be inserted into a patient monitoring device PCMCIA data slot.
- The card 2000 interfaces to the patient monitoring device 106 in such a way as to appear to the patient monitoring device 106 as a valid LF card ("linear flash analog") 2122.
- The card 2000 presents the PCMCIA byte stream, written by the patient monitoring device 106, via a buffered hardware interface, to a SOM processor.
- The carrier stores the received PCMCIA byte stream to a non-volatile storage subsystem ("linear flash analog") such that all of the patient monitoring device 106 read/write/erase functionality is preserved in all device 106 modes of operation supporting these operations.
- The SOM provides IEEE 802.11.a/b/g/n wireless communications capability.
- The SOM provides Bluetooth V2.0+EDR wireless communications capability.
- The SOM provides a micro SD card slot.
- The SOM supports watchdog type monitoring to provide for automatic reset if the SOM becomes non-functional.
- During patient monitoring device 106 or SOM reset or initialization, data is captured to flash analog memory.
- Data capture continues uninterrupted during SOM reset.
- The system 5000 is designed such that data being written by the patient monitoring device 106 is saved to the flash analog regardless of SOM state
- The SOM is able to access data saved while the SOM was unavailable.
- The carrier board provides a USB connector.
- The carrier SOM combination supports USB 2.0 On-The-Go ("OTG").
- Device 2000 form factor includes PCMCIA standard dimensions in width and height.
- Device 2000 form factor includes a width of 85.6 mm×54.0 mm×a thickness (in some cases, this thickness is greater than type III which is 10.5 mm)
- Device 2000 thickness is no larger than permitted by device 106 PCMCIA slot.
- All carrier board components are mounted on one side of the carrier card.
- The interface to the patient monitoring device 106 is via slot bay via 68-pin PCMCIA card edge connector.
- Device 2000 is encapsulated to meet medical device requirements for EMC/RFI.
- The SOM is mounted on the carrier using 2 AVX 5602 70 pin connectors.
- Device 2000 is powered from the PCMCIA data slot, which may be on the order of 2.5 W continuous with peak current not exceeding 600 mA.
- Device 2000 may utilize 15 GPIO pins to control reading FIFO byte stream buffer.
- Device 2000 may utilize 3 UART lines from the SOM connected and a USB bridge on the carrier.
- Device 2000 may include an antenna for WiFi.
- Device 2000 may include an antenna for BT.
- Device 2000 may use an Angstrom Open Embedded Linux operating system ("O/S").
- The device 2000 0/S may include Mono for the purposes of running code implemented in C#.
- The device 2000 O/S may include SQLite.
- The device 2000 may support the use of USB for bidirectional serial communications.
- The device 2000 provides secure wireless communications, including end-point authentication, confidentiality, integrity, and/or delivery confirmation.
- External data recipients (external processes to the device 2000) are able to request streaming data delivery.
- Data recipients are able to request complete incident data delivery by incident identifier, e.g. post-incident data.
- Device 2000 software is upgradeable via wireless interface.
- Device 2000 software is verified at run time using a cyclic redundancy code ("CRC")-like mechanism.

A device 2000 according to an embodiment of the present invention may permit individual screens for different receiving devices (e.g. different receiving devices using the communications interface 1104) to permit different users to obtain different data. For example, one user's settings could be configured to receive and display the frame event stream data relating to a patient's twelve-lead data, while an administrative technician user's settings could be configured to periodically request only frames associated with error codes generated by the patient monitoring device 106, according to embodiments of the present invention. Similarly, the same data may be received by and/or displayed by multiple users simultaneously over a WiFi connection, according to embodiments of the present invention.

In this way, the data from a patient monitoring device 106 may be streamed, e.g. over a wireless WiFi connection, from a patient's house to or from an ambulance, and/or from an ambulance to or from a hospital. Various frames in the event stream may be filtered and/or requested, such that a specific subset of data may be obtained. For example, respiration data may be included in a frame event stream generated by device 2000, according to embodiments of the present invention.

A device 2000 according to an embodiment of the present invention may be combined with other types of patient monitoring devices 106, for example an automatic external defibrillator ("AED"). The device 2000 may thus be configured to send status information from the AED, to facilitate software updates for the AED, and/or to remotely test the AED, according to embodiments of the present invention. Such a device 2000 may also be used with a patient charting device, for example to combine the patient charting device 108 information from one vendor/platform with the patient monitoring device 106 information from another vendor/platform, according to embodiments of the present invention. The device 2000 may also function as a data aggregator, to parse, organize, and place streams of information into discrete frames information that are more easily sorted, queried, and supplied at a later, post-incident time frame, according to embodiments of the present invention.

According to embodiments of the present invention, the patient monitoring device 106 (e.g. defibrillator) sends data to the device 2000 in data blocks, for example ECG data, or patient's current heart rate. A collection of data blocks corresponding to one incident may be referred to as incident data. Full disclosure data is the concatenation of data associated with all incidents, and may be broken into sequences of data blocks corresponding to each individual/patient. When a service request is received for an incident, all of the frames stored on device 2000 for that incident are collected and put together in sequence. According to embodiments of the present invention, each ECG block corresponds to 100 ms of ECG data, which provides ten data blocks per second. The defibrillator may add to each data block an incident identifier, time information about when the data block was recorded, and/or a computing hash for data integrity purposes, according to embodiments of the present invention.

Device 2000 (which is referred to in some figures as a "Zango" device) and BOA device 104 (which is referred to in some figures as a RescueNet Link, or RNL, device) work together, according to embodiments of the present invention. Device 2000, by virtue of its embedded computer, embodies a powerful processing engine. This processing engine is used to manage sophisticated data, communications, and applications operations on behalf of BOA device 104 users, according to embodiments of the present invention. According to one embodiment of the present invention, the device 2000 does not have input/output user interfaces (e.g., no keyboard, or display), so it works in conjunction with BOA device 104 to provide users access to the communications and data management services it supports, according to embodiments of the present invention.

FIGS. 20 and 23 illustrate the logical and functional architecture of the EMS communications interface card 2000 processing and the BOA device 104 processing, respectively. When device 2000 is not connected to device 104, device 2000 stores all device data and can transmit it to device 104 when a connection is established or restored.

Figure 30:
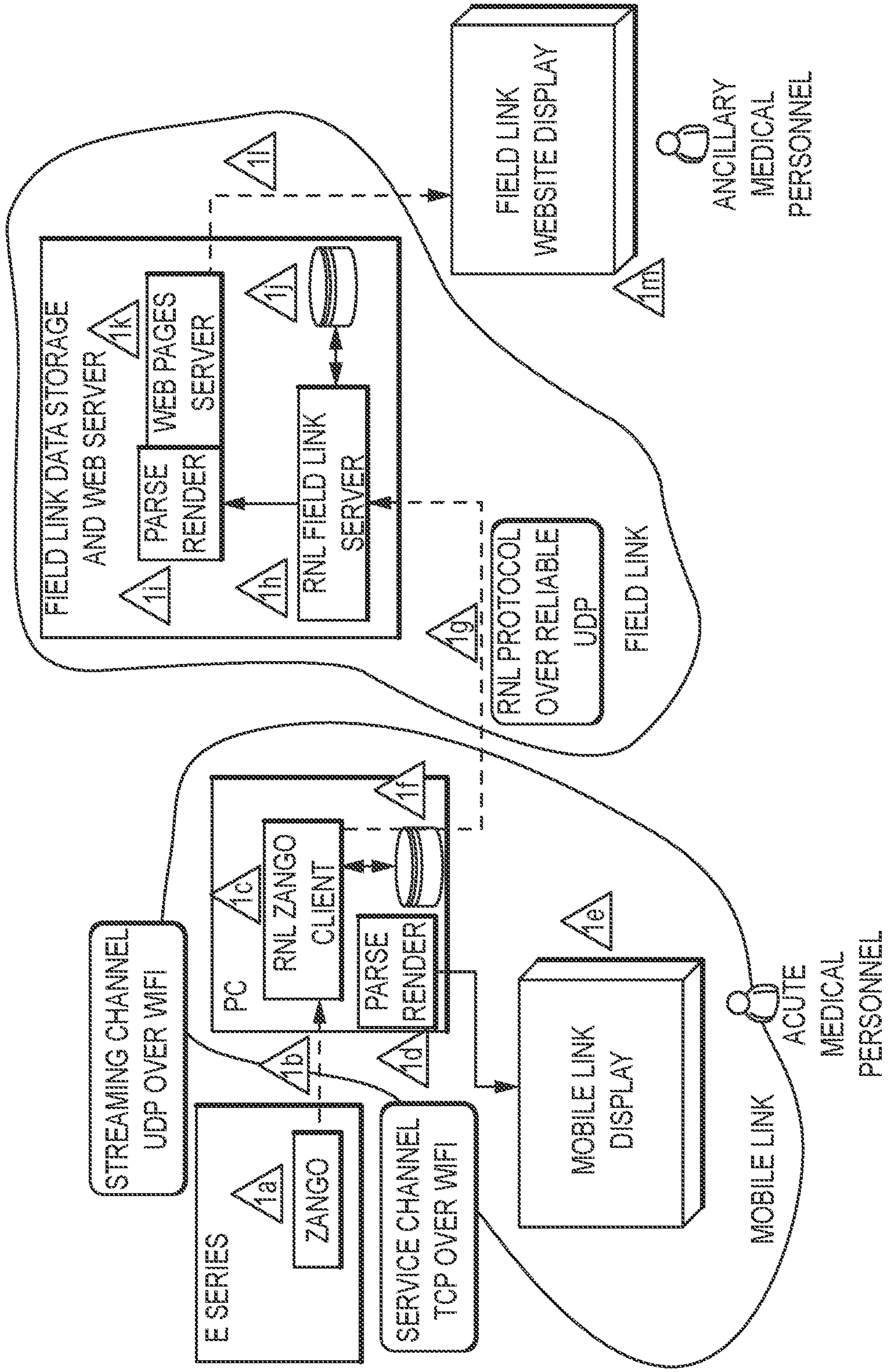
FIG. 30 illustrates a data transmission interface, according to embodiments of the present invention.

FIG. 30 illustrates a data transmission interface, according to embodiments of the present invention. Zango device (1*a*), can be configured to perform a number of functions, according to embodiments of the present invention:

- Frame defibrillator incident data blocks.
- Stream framed incident data.
- Save incident data frames to Zango database.
- Host a set of data management services upon the Zango database.
  - In one embodiment, data management services are read/erase only. Services to modify incident data are not supplied.

The "EMS communications interface channel" (1*a*, 1*b*, 1*c*) provides a means to transmit patient monitoring data (e.g. E Series data) to the BOA device 104. This channel uses the device 2000 to connect to BOA 104.

The RNL Zango Client (1*c*) can be configured to perform a number of functions:

- Receive streamed incident frame data (1*b*).
- Present incident frame data on the Mobile Link Display (1*e*) (parse, render, 1*d*).
- Store incident frame data into the Mobile Link database (1*f*)
- Host a set of data management services upon the Mobile Link database (1*f*).
  - In some embodiments, data management services are read/erase only; and services to modify incident data are not supplied.
- Forward 12 lead ecg and vitals data to Field Link. (1*g*)
- Consume Zango data management services (1*b*).

The following table lists and describes various elements of FIG. 30, described with respect to one embodiment of the present invention.

| Notation (FIG. 30) | Description | Notes |
|---|---|---|
| 1a | Zango accessory | Data management accessory for ZOLL E Series. Captures, stores, and transmits E Series data written to the E Series data slot to connect the E Series data to RNL. |
| 1b | Zango UDP/IP transmissions over WPA2 secured 802.11. | |
| 1b | Zango TCP/IP service invocation response transactions over WPA2 secured 802.11. | |
| 1c | RNL Zango Client | RNL receiver of Zango transmissions. |
| 1a, 1b, 1c | Zango channel | |
| 1d | Zango parsing and rendering engine | Zango messages from the E Series are parsed and rendered for acute medical viewing. |
| 1e | Mobile Link Display | |
| 1f | Mobile Link Storage | |
| 1g | RNL Protocol: Reliable UDP/IP over secured cellular networks. | |
| 1h | RNL Field Link Server | Mobile link message receiver in Field Link environment. |
| 1c, 1g, 1h | RNL Mobile Link to Field Link Communications Channel | The RNL Mobile Link to Field Link Channel connects Mobile Link to Field Link using reliable UDP/IP over secured cellular networks. |
| 1j | Field Link Storage | |
| 1i | Field Link parsing and rendering engine | |
| 1k | Field Link web server | |
| 1l | Secured connection to Field Link users | |
| 1m | Field Link web viewer | |

Figure 31:
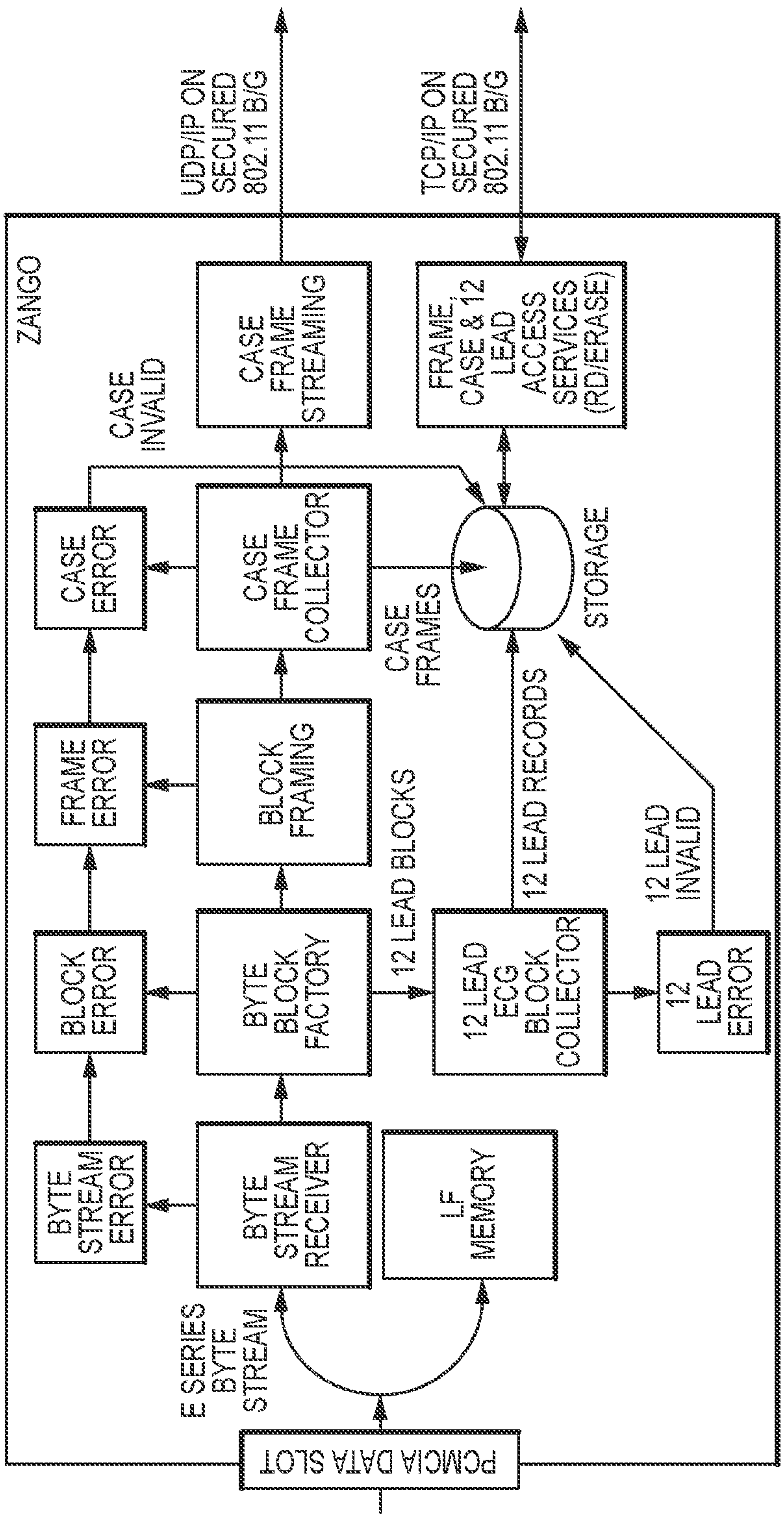
FIG. 31 illustrates an EMS communication interface transmission processing block diagram, according to embodiments of the present invention.

FIG. 31 illustrates an EMS communication interface transmission processing block diagram, according to embodiments of the present invention. The E Series writes a continuous byte stream of data to the PCMCIA Data Slot. The byte stream consists of E Series data block messages some of which are sent periodically and some of which are sent episodically. An example a periodic message is the ecg message. The E Series writes the ecg values for the currently displayed lead once per 100 ms, the message contains 25 data values (250 Hz samples, 4 ms apart), according to embodiments of the present invention.

Examples of episodic messages are the vital sign messages. The E Series sends a particular vital sign message when a particular vital sign parameter value has changed; asynchronous messages are sent with no particular frequency, according to embodiments of the present invention.

The byte stream is bifurcated at the input to the Zango card. One branch stores data into an on board (16 MB) linear flash, replicating all of the E Series linear flash operations. All data written is stored in the linear flash subsystem. The interface is hardware level, instant on prepared to receive and save the E Series byte stream to flash subsystem.

The second byte stream branch goes into the processor side of the Zango card. The processor side of the Zango card functions to process the byte stream performing the logical operations illustrated in FIG. 31. In the non-faulted case the byte stream receiver passes bytes to the byte block factory. The byte block factory re-constructs E Series data block messages from the byte stream. In this operation, 12 lead ecg data blocks are reconstructed and managed on a separate path to the incident path (sets of 12 lead data blocks are collected into entire 12 lead messages). The 12 lead data is entirely preserved in the case stream. One of the reasons for storing them separately is to permit a service user to request to see a 12 lead record on the service channel, rather than uploading the entire incident to get the 12 lead data, according to embodiments of the present invention.

Blocks are then framed into a configurable time interval's worth of data blocks. For example, frames of one second in size might have on the order of 15 data blocks in the one second frame. Frames are collected into constructs of cases or incidents. Frames are stored in the Zango database. Complete incidents are marked (collection of all incident frames) and managed as incidents as they are completed. Frames are also streamed on WiFi where they can be received by authorized client applications, such as the RNL Zango Client described, below, with respect to FIG. 32.

The upper row of boxes in FIG. 31 identify detection and error handling processes for risk control of compromised data faults, according to embodiments of the present invention. Byte stream, block, framing, 12 Lead, or incident error all result in the following behaviors, according to embodiments of the present invention:

- Data is marked as invalid.
- Invalid data is not rendered for a user to view during the acute treatment phase of an incident
- Data is stored marked as invalid for forensic analysis.
- Any one of these faults will cause the incident to be marked invalid.
- Acute medical personnel are informed of data faults, assuming connectivity to RNL.

These are the control measures and behaviors that trace directly to the hazard analysis for data compromised faults, in one embodiment of the present invention.

Figure 32:
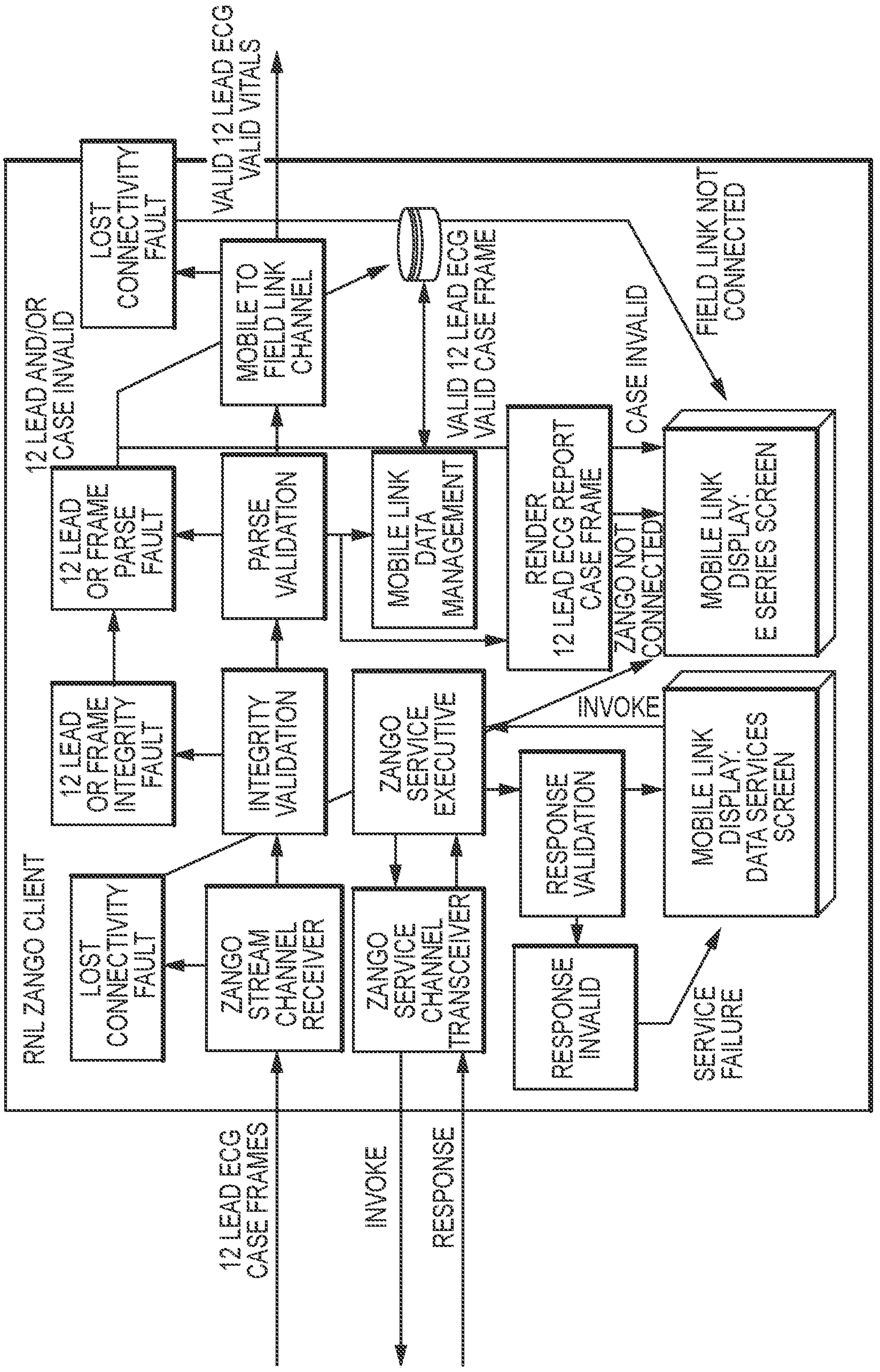
FIG. 32 illustrates a EMS communications interface device client architecture, according to embodiments of the present invention.

FIG. 32 illustrates a EMS communications interface device client architecture, according to embodiments of the present invention. In some cases, Zango connectivity to RNL may be volatile as a result of the nature of wireless communications in mobile environments. For example, an E Series equipped with a Zango card may be moved out of range of the wireless access point to which it had been connected. When the device is back in range and reconnects, processing resumes as illustrated. Data written by the E Series while not connected to RNL is persisted in the Zango database and can be obtained in RNL upon re-connect, according to embodiments of the present invention.

The upper row of boxes in FIG. 32 identify detection and error handling processes for risk control of compromised data faults and communications faults. Integrity or framing faults detected on the streamed data result in the following behaviors, according to embodiments of the present invention:

- Data is marked as invalid.
- Invalid data is not rendered for a user to view during the acute treatment phase of an incident
- Data is stored marked as invalid for forensic analysis.
- Either of these faults will cause the incident to marked invalid.
- Acute medical personnel are informed of data faults for either 12 leads or case frames.
- Acute medical personnel are informed of communications faults.
- Acute medical personnel are informed of service faults.

Service responses are validated and invalid service responses are notified to the user and invalid data is not displayed, according to embodiments of the present invention. Connectivity status between Zango and the Zango Stream Channel Receiver is monitored and reported to users on the Mobile Link Display. Lost connectivity between Zango and RNL does not result in lost data as Zango stores data in the Zango database regardless of connection status. Service channel connectivity is not continuously monitored, service requests will fail (response invalid) if service connectivity is not present.

Figure 33:
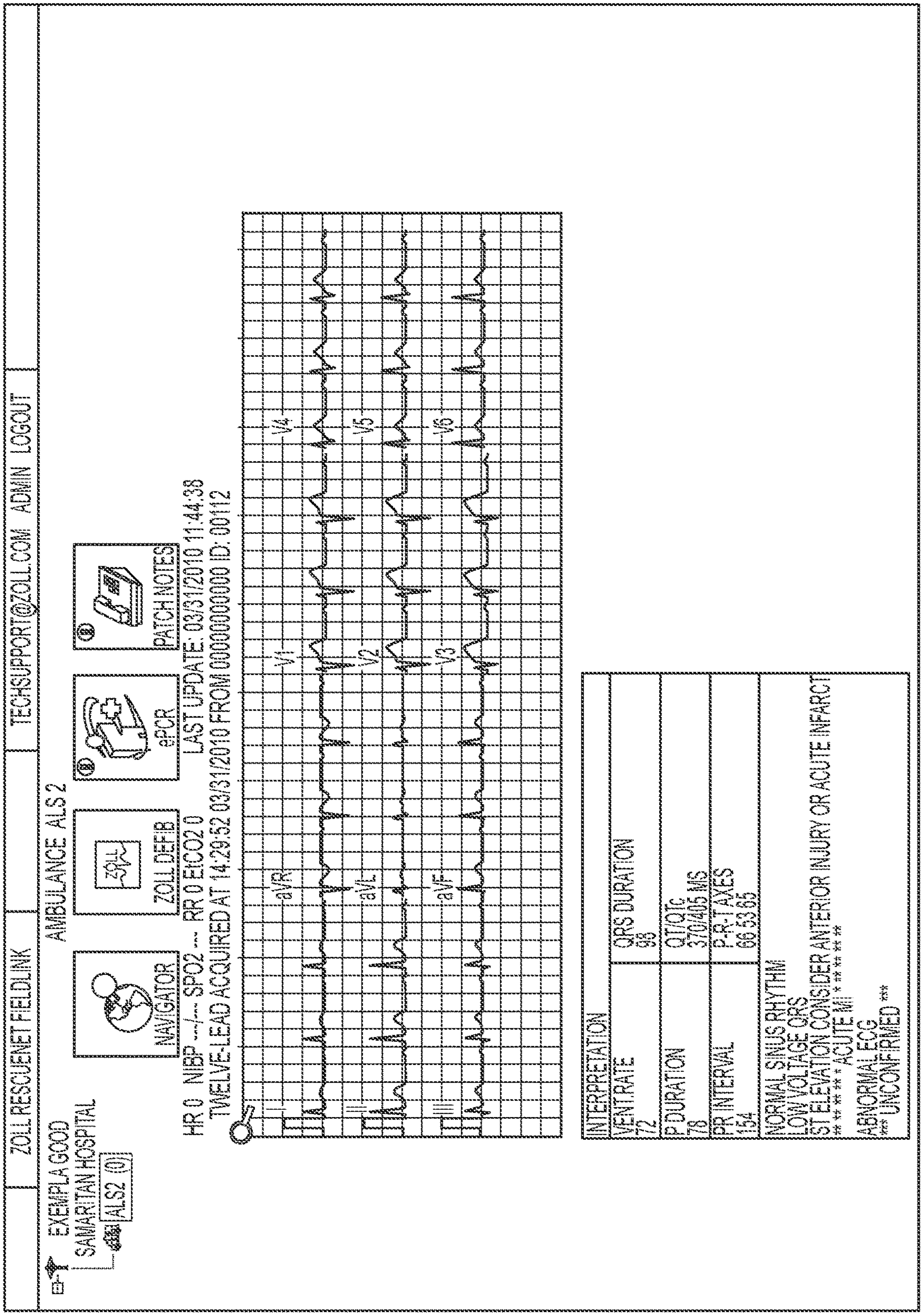
FIG. 33 illustrates an enterprise display and graphical user interface shown when the enterprise user selects the patient monitoring button, according to embodiments of the present invention.
Figure 34:
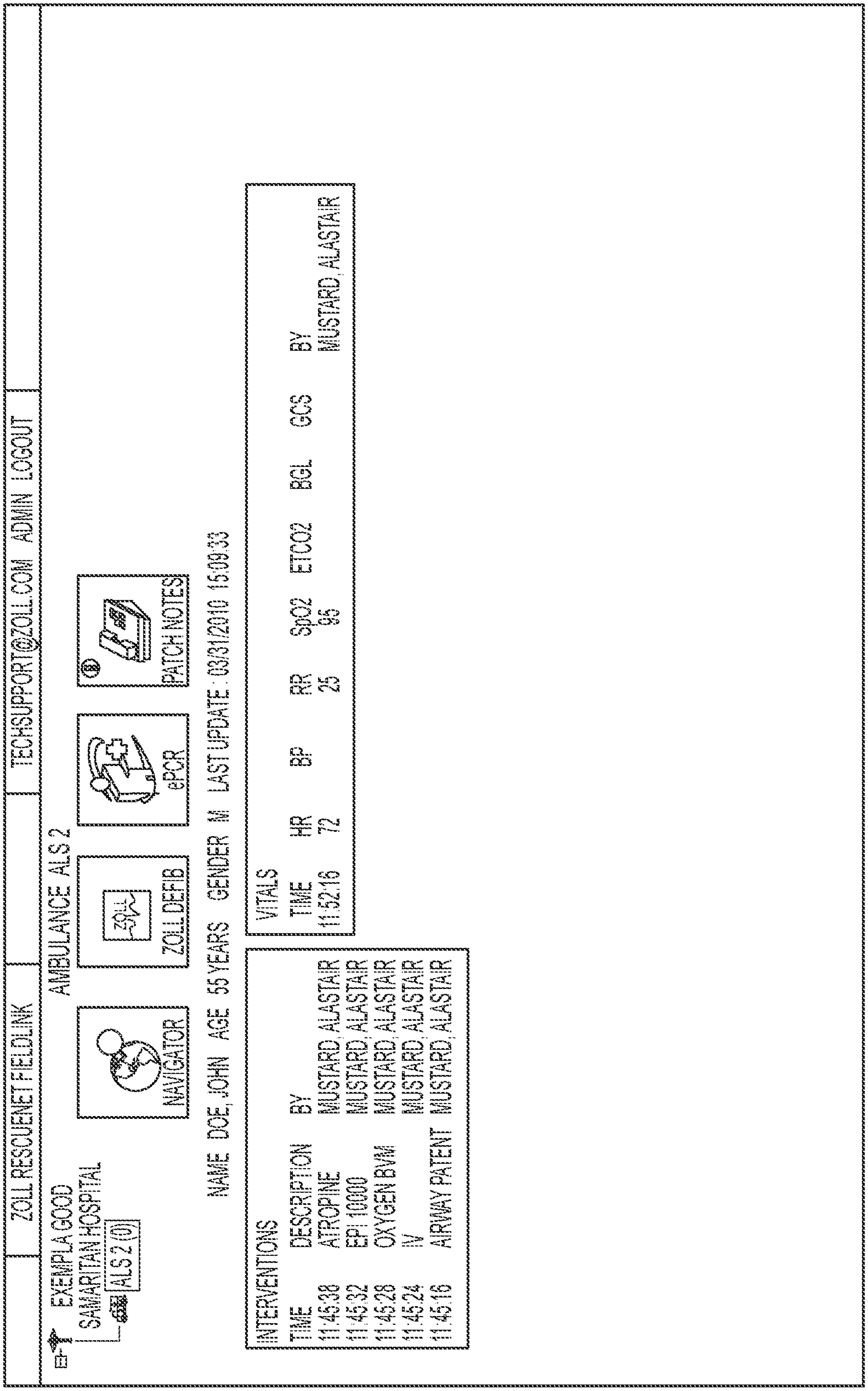
FIG. 34 illustrates an enterprise display and graphical user interface shown when the enterprise user selects the patient charting button, according to embodiments of the present invention.
Figure 35:
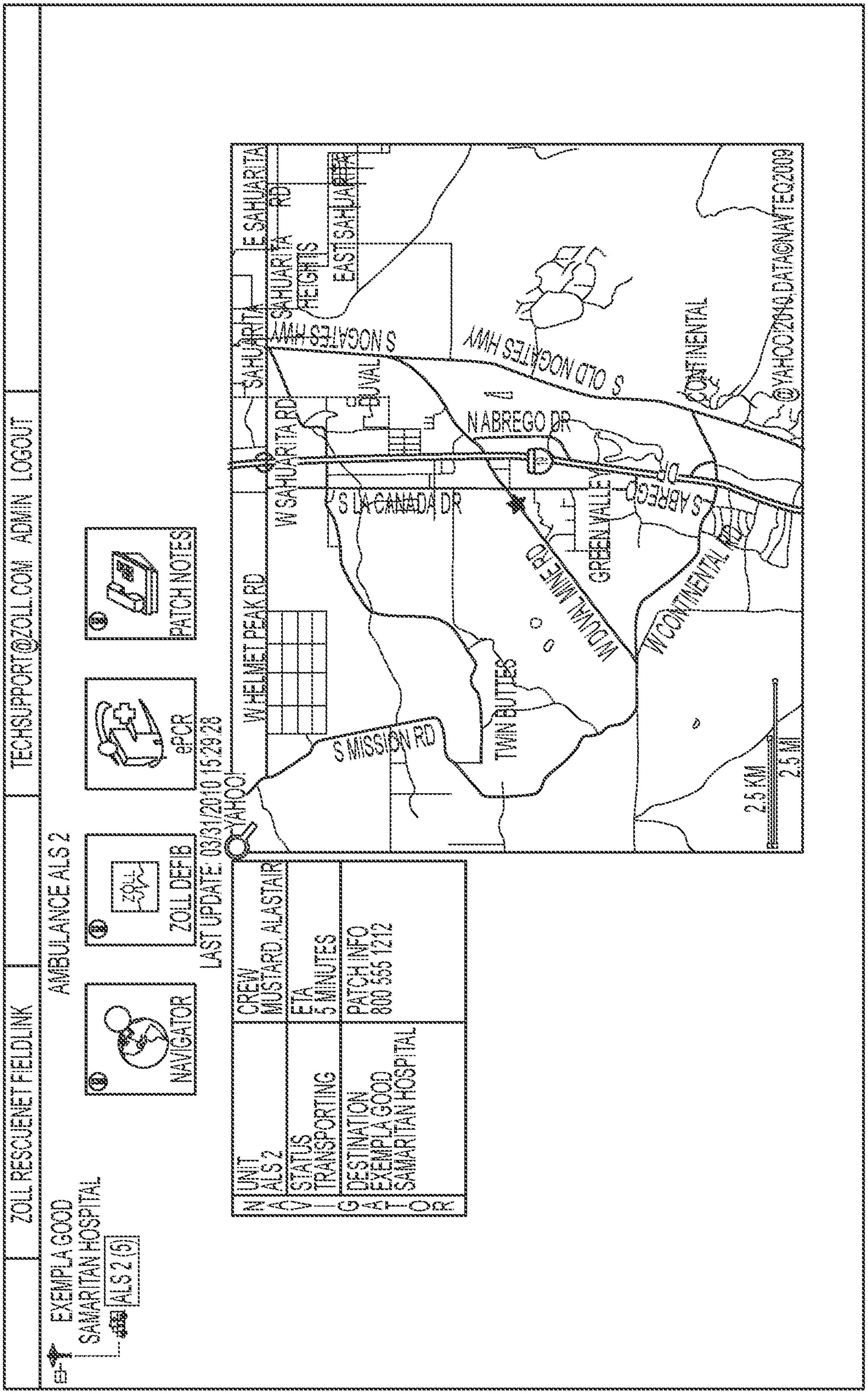
FIG. 35 illustrates an enterprise display and graphical user interface shown when the enterprise user selects the navigation button, according to embodiments of the present invention.

FIGS. 33-37 illustrate various embodiments of screen shots available as viewed by the enterprise user 124 via the enterprise workstation 122, according to embodiments of the present invention. FIG. 33 illustrates an enterprise display and graphical user interface shown when the enterprise user selects the patient monitoring button (e.g. the "Zoll Defib" button), according to embodiments of the present invention. FIG. 34 illustrates an enterprise display and graphical user interface shown when the enterprise user selects the patient charting button (e.g. the "ePCR" button), according to embodiments of the present invention. FIG. 35 illustrates an enterprise display and graphical user interface shown when the enterprise user selects the navigation button, according to embodiments of the present invention.

Figure 36:
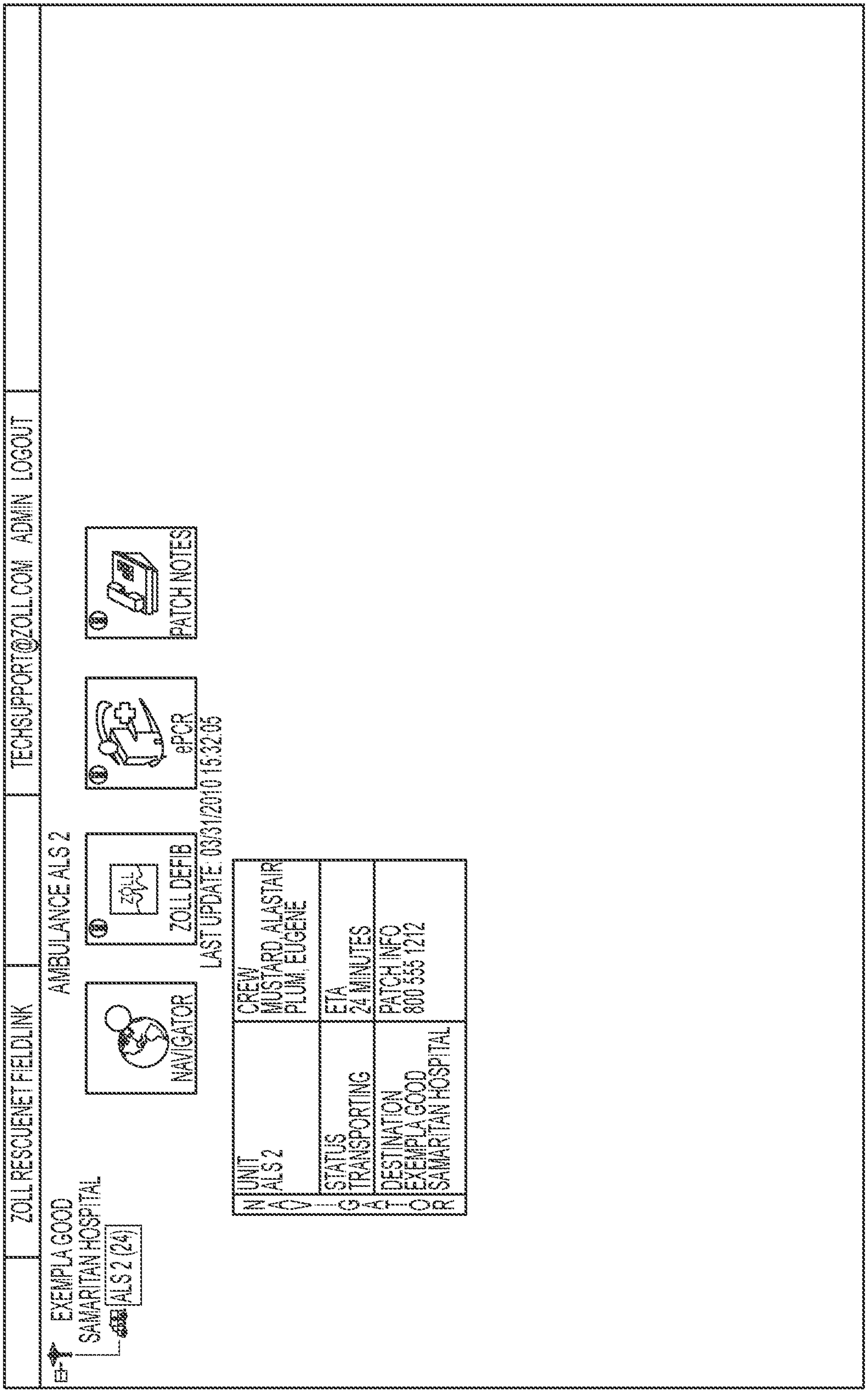
FIG. 36 illustrates an alternative enterprise display and graphical user interface shown when the enterprise user selects the navigation button, according to embodiments of the present invention.
Figure 37:
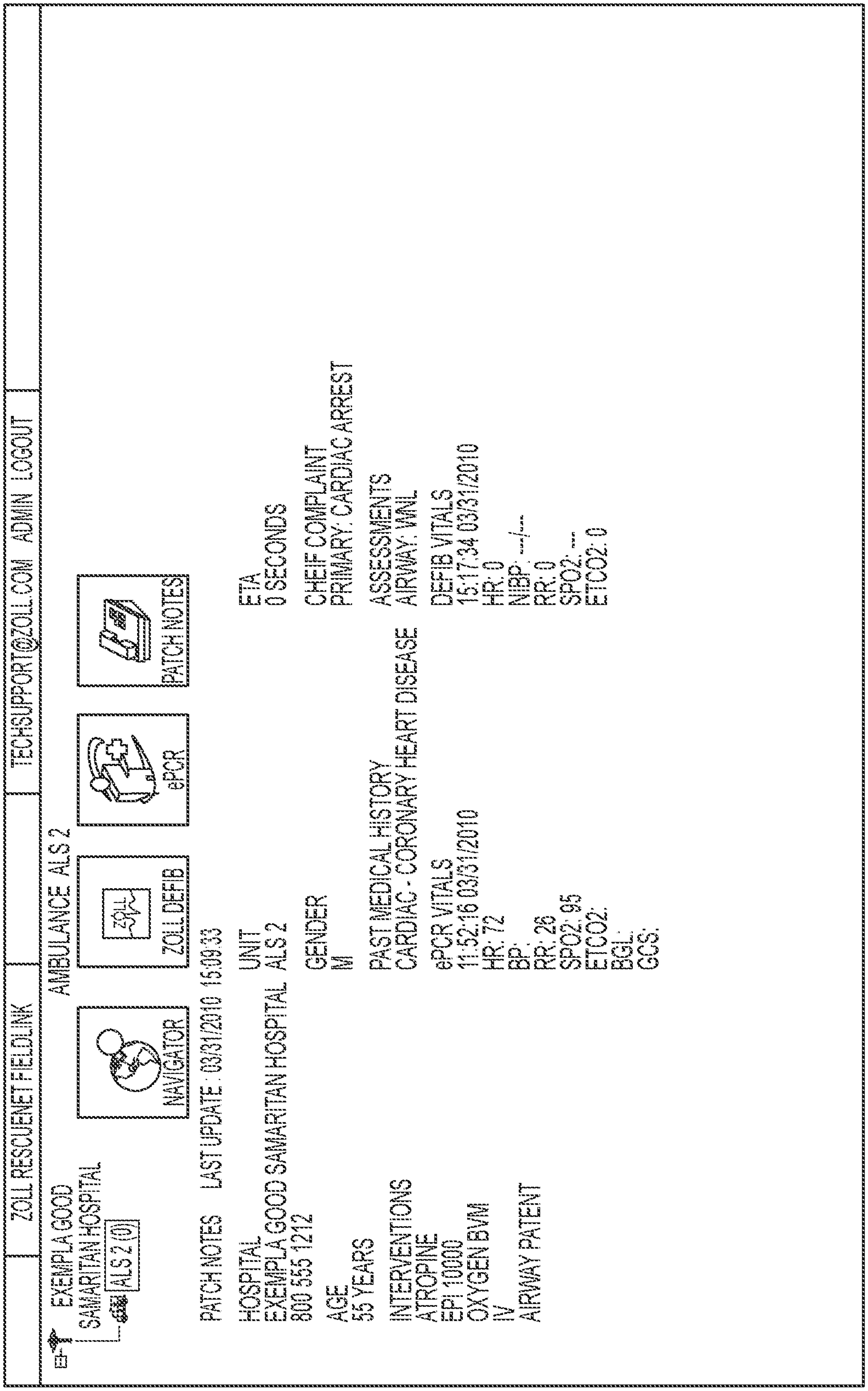
FIG. 37 illustrates an enterprise display and graphical user interface shown when the enterprise user selects the patch notes button, according to embodiments of the present invention.

FIG. 36 illustrates an alternative enterprise display and graphical user interface shown when the enterprise user selects the navigation button, according to embodiments of the present invention. The display of FIG. 36 would correspond to a display created when the BOA device 104 is not communicably coupled with a navigation device; hence, in this situation, the enterprise display lists the positional and/or navigation information as input by the BOA 104 user. FIG. 37 illustrates an enterprise display and graphical user interface shown when the enterprise user selects the patch notes button, according to embodiments of the present invention. According to some embodiments of the present invention, the EMS technician 114 who is interacting with the BOA device 104 need not select the patch notes screen and relay the information to the enterprise user 124; instead, the enterprise user may select the patch notes button via the enterprise workstation 122 to observe the same information.

Figure 38:
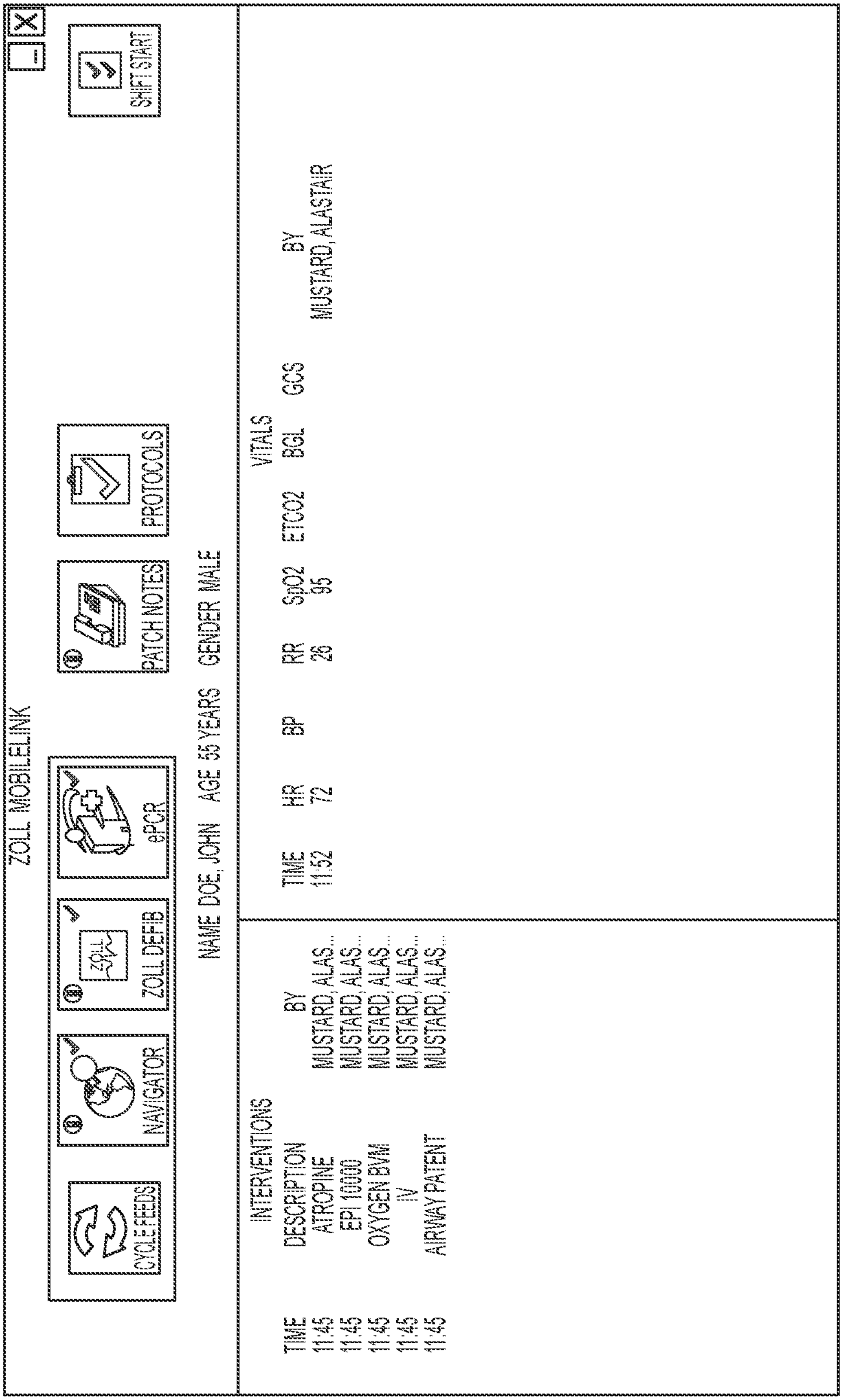
FIG. 38 illustrates a display and graphical user interface displayed when the user selects the patient charting button of a BOA menu template, according to embodiments of the present invention.
Figure 39:
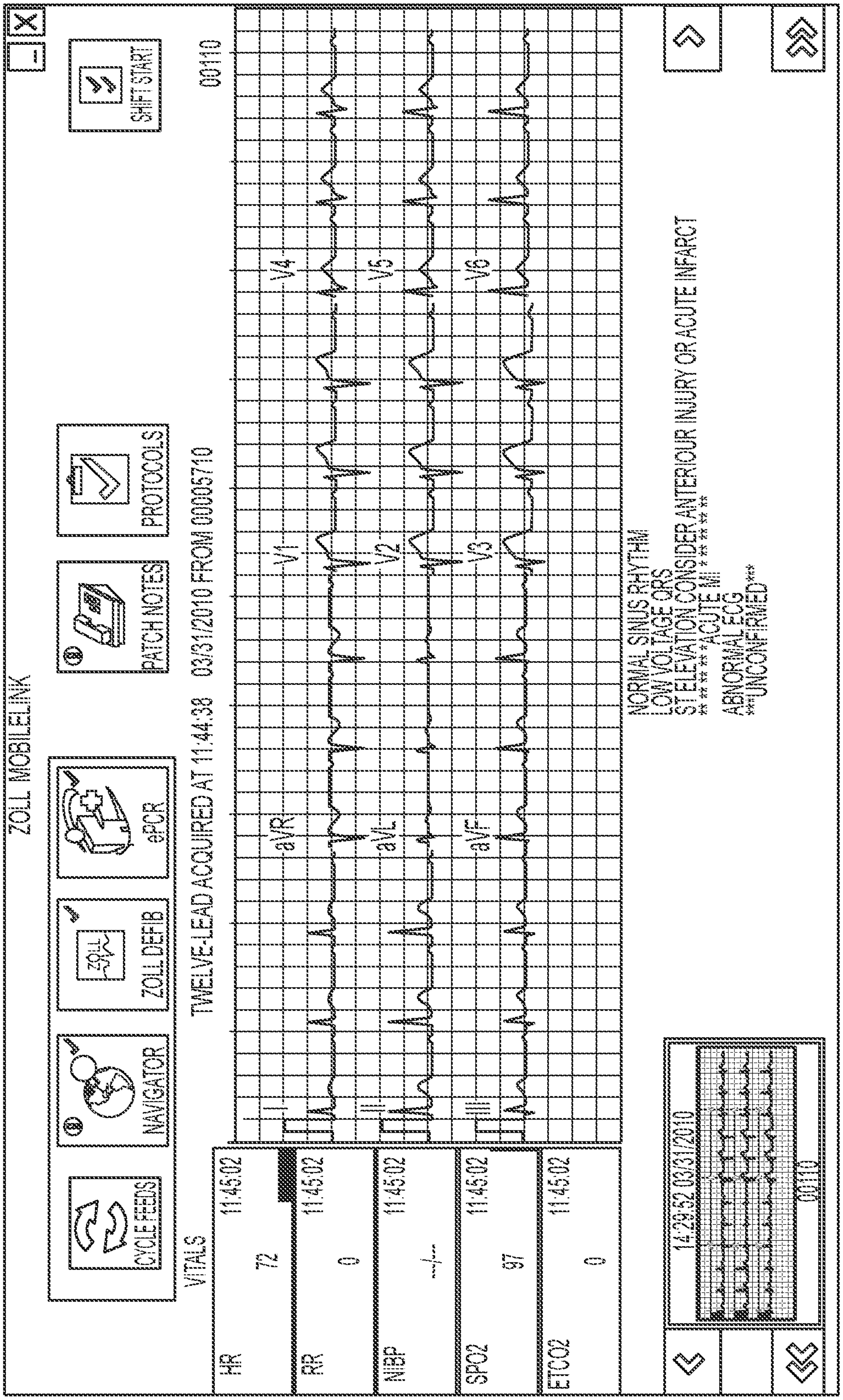
FIG. 39 illustrates a display and graphical user interface displayed when the user selects the patient monitoring button of a BOA menu template, according to embodiments of the present invention.

FIGS. 38-44 illustrate additional examples of screen shots displayed by BOA device 104, according to embodiments of the present invention. FIG. 38 illustrates a display and graphical user interface displayed when the user selects the patient charting button of a BOA menu template, according to embodiments of the present invention. FIG. 39 illustrates a display and graphical user interface displayed when the user selects the patient monitoring button of a BOA menu template, according to embodiments of the present invention. As illustrated by the thumbnail twelve-lead image in the bottom left corner, this BOA device 104 may be configured to display historical snapshots of past twelve-lead data, according to embodiments of the present invention.

Figure 40:
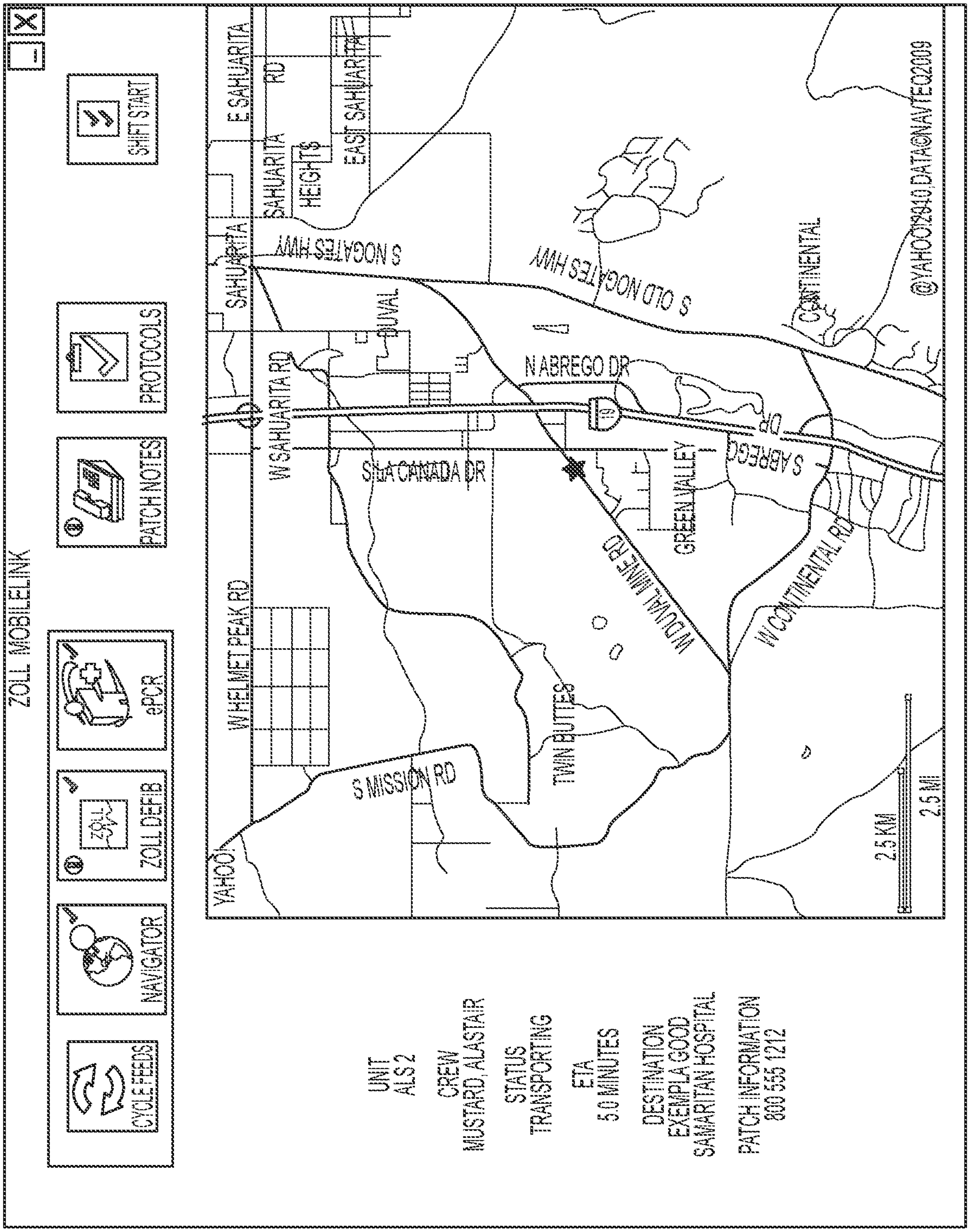
FIG. 40 illustrates a display and graphical user interface displayed when the user selects the navigation button of a BOA menu template, according to embodiments of the present invention.
Figure 41:
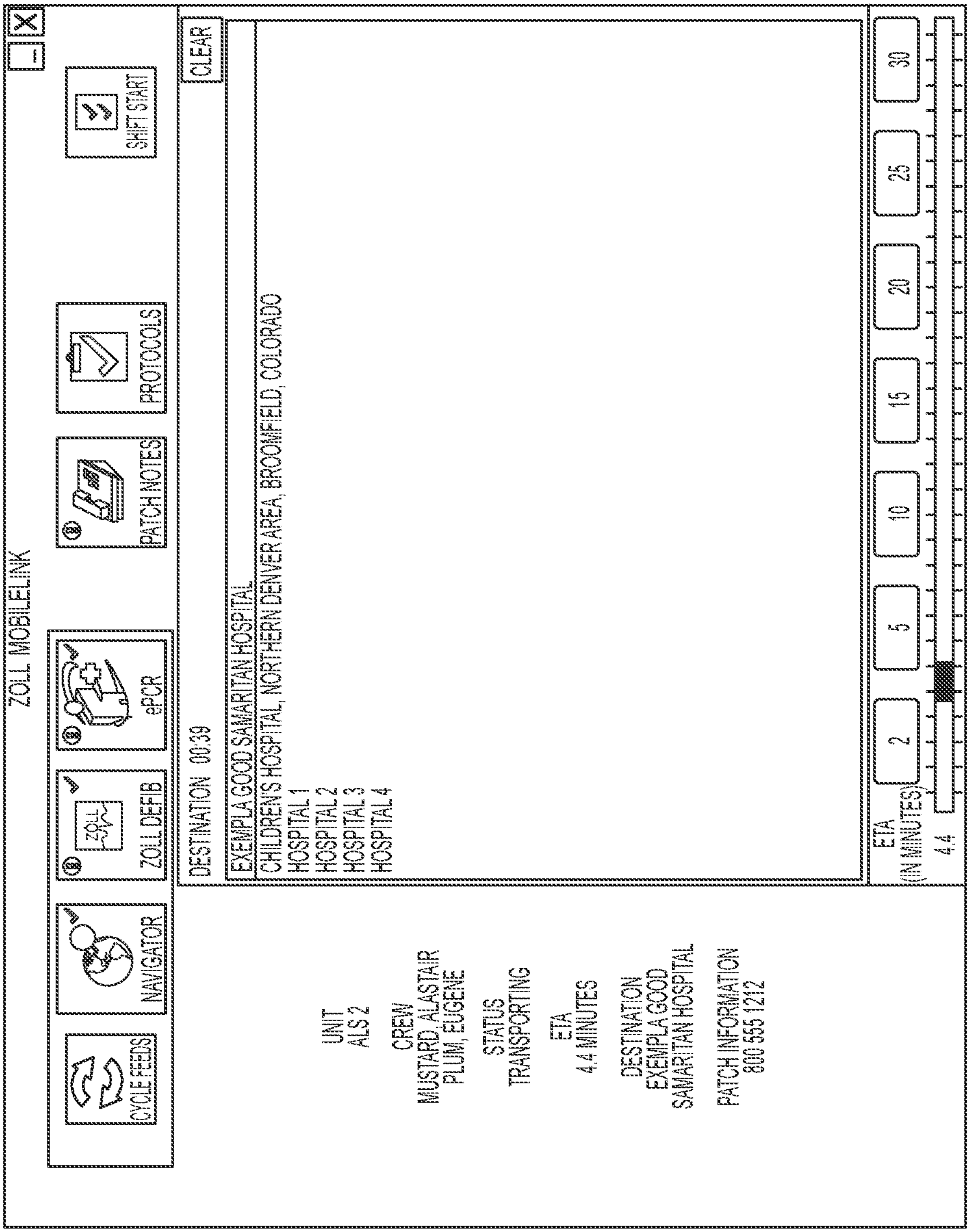
FIG. 41 illustrates an alternative display and graphical user interface displayed when the user selects the navigation button of a BOA menu template, according to embodiments of the present invention.

FIG. 40 illustrates a display and graphical user interface displayed when the user selects the navigation button of a BOA menu template, according to embodiments of the present invention. FIG. 41 illustrates an alternative display and graphical user interface displayed when the user selects the navigation button of a BOA menu template, in situations in which a navigation device 110 is not communicably coupled to the BOA device 104. In such situations, the screen of FIG. 41 is configured to permit a user to manually select a destination, as well as select an estimated time of arrival, according to embodiments of the present invention. This information may be replicated or otherwise transmitted to the corresponding enterprise view (e.g. FIG. 36), according to embodiments of the present invention.

Figure 42:
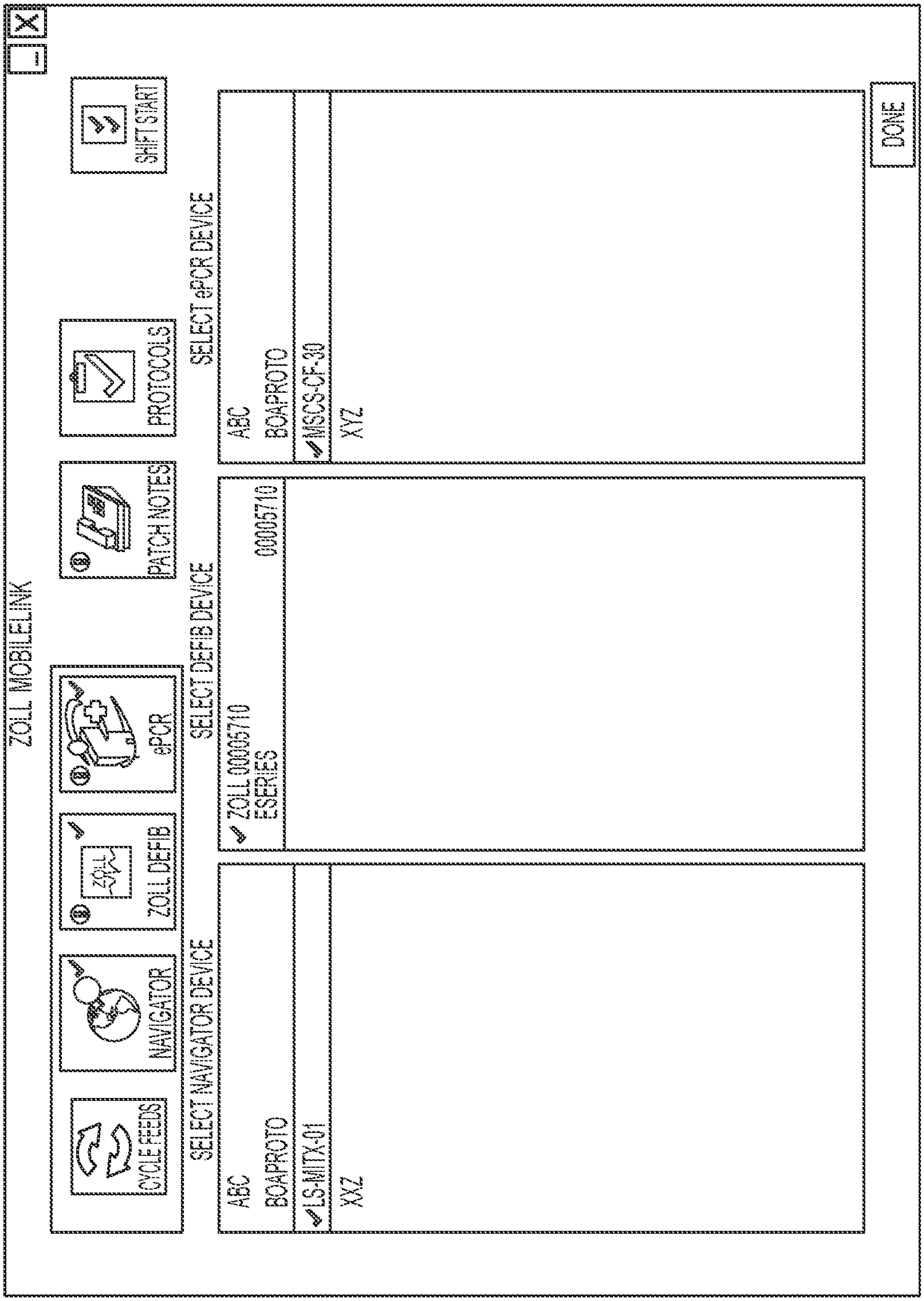
FIG. 42 illustrates a display and graphical user interface displayed when the user selects the shift start button of a BOA menu template, according to embodiments of the present invention.

FIGS. 38-44 illustrate that a "shift start" button maybe included on the BOA device 104 interface. The shift start button may be used, for example, at the beginning of a shift, in order to permit the EMS technician or other user to communicably couple the BOA device 104 with other devices, according to embodiments of the present invention. FIG. 42 illustrates a display and graphical user interface displayed when the user selects the shift start button of a BOA menu template, according to embodiments of the present invention. In this screen, the user is permitted to select a navigation device, a defibrillator device, and a patient charting device; in this screen, the user is also able to confirm the identities of the devices to which the BOA device 104 is already communicably coupled, as indicated in this particular example by a checkmark next to the device name, according to embodiments of the present invention.

Figure 43:
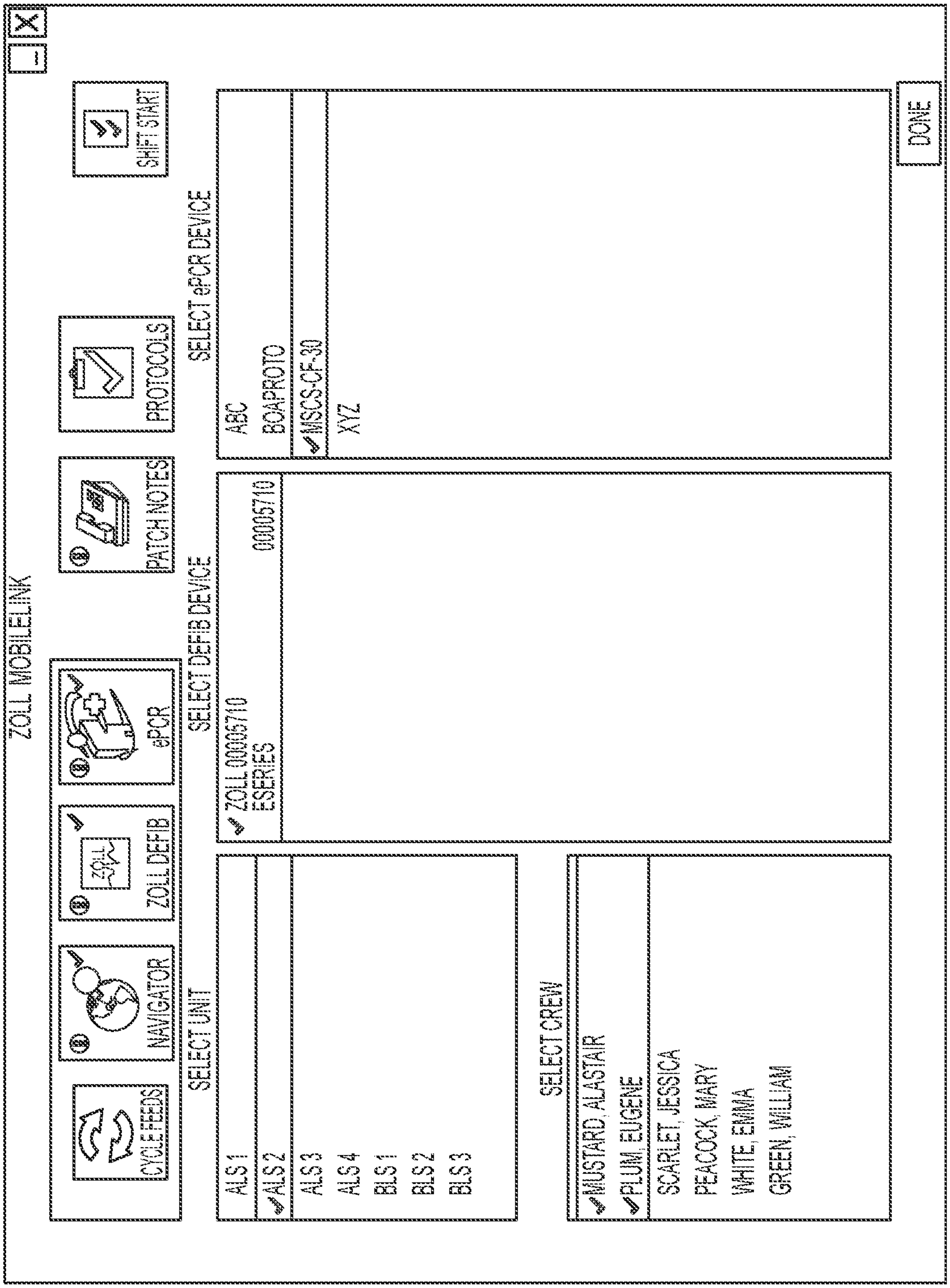
FIG. 43 illustrates an alternative display and graphical user interface displayed when the user selects the navigation button of a BOA menu template, according to embodiments of the present invention.
Figure 44:
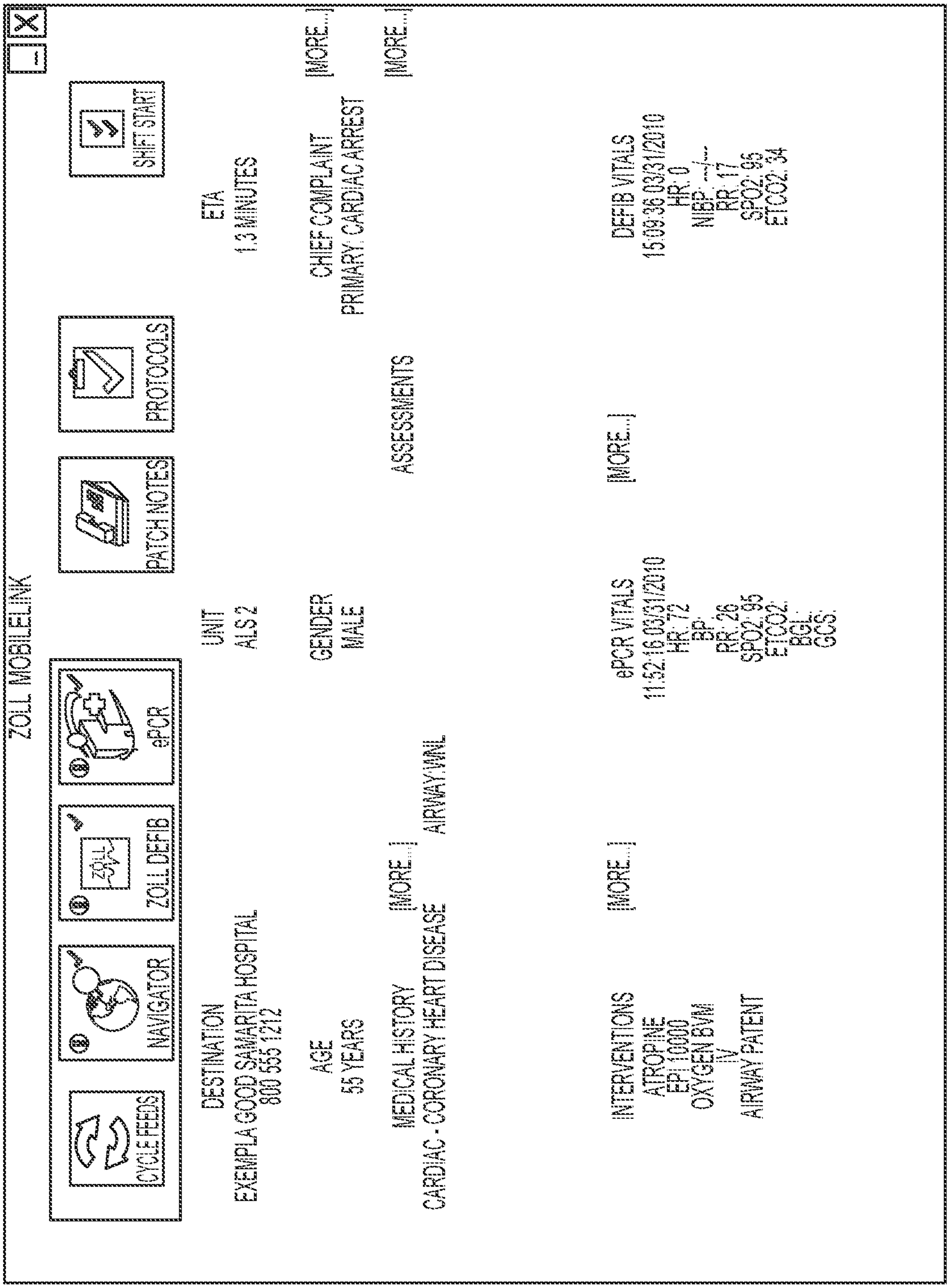
FIG. 44 illustrates a display and graphical user interface displayed when the user selects the patch notes button of a BOA menu template, according to embodiments of the present invention.

FIG. 43 illustrates an alternative display and graphical user interface displayed when the user selects the shift start button of a BOA menu template, according to embodiments of the present invention. In this alternative display, the BOA device 104 has sensed that a navigation device 110 is not available or is disconnected, and thus prompts the user to identify the EMS transport unit and/or the crew members present with the unit. This information may be used in the corresponding navigation screens for the BOA device (FIG. 41) and the enterprise environment 102 (FIG. 36). FIG. 44 illustrates a display and graphical user interface displayed when the user selects the patch notes button of a BOA menu template, according to embodiments of the present invention.

Figure 62:
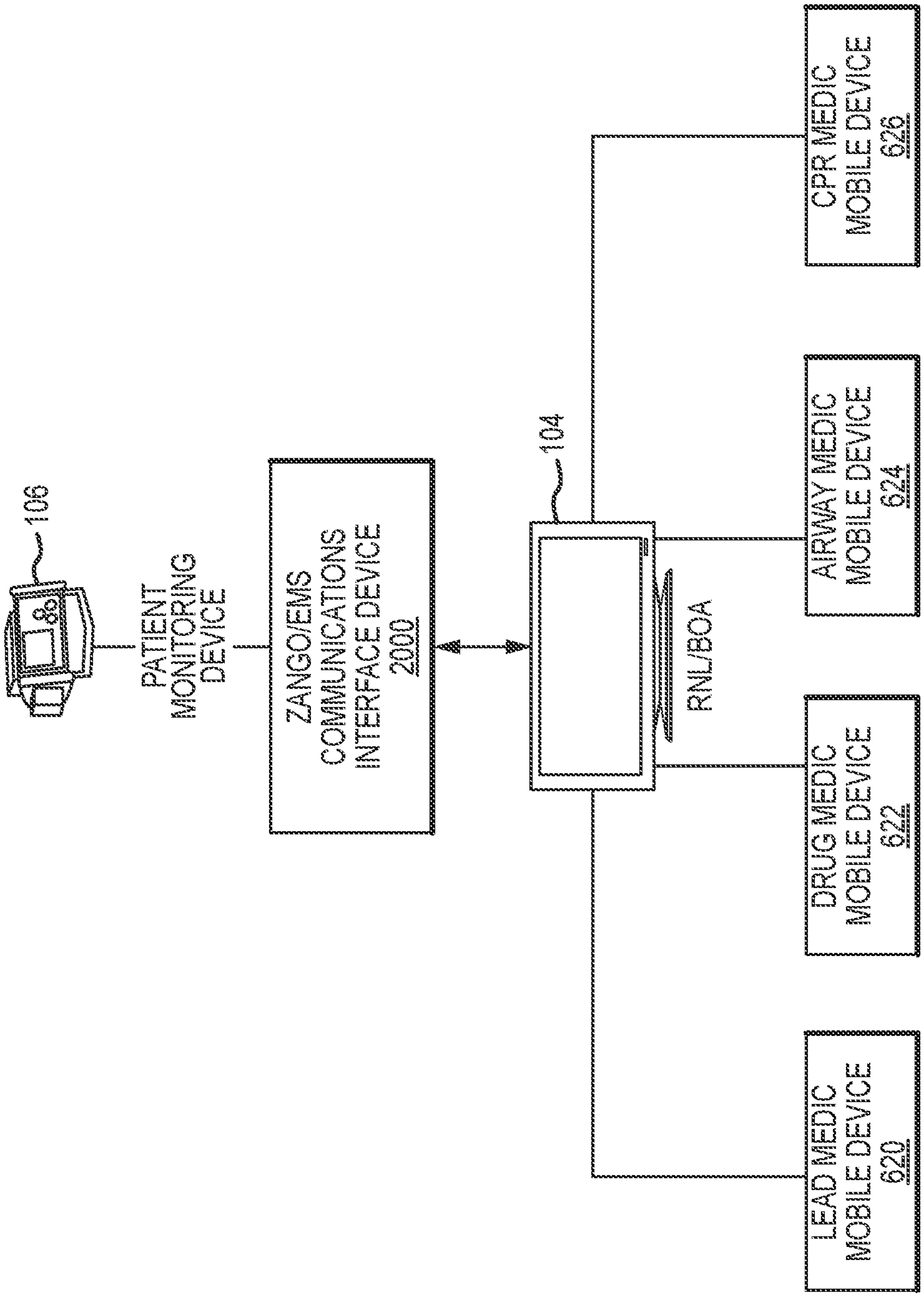
FIG. 62 illustrates a system for role-based data feeds from a BOA device to EMS technician mobile devices, according to embodiments of the present invention.

FIG. 62 illustrates a system for role-based data feeds from a BOA device to EMS technician mobile devices, according to embodiments of the present invention. BOA device 104 receives streaming ECG data and other data from the patient monitoring device 106, which may be accomplished wirelessly via an EMS communications interface device 2000 as described above, according to embodiments of the present invention. The BOA device 104 displays such information on a screen such as the screen illustrated in FIG. 45.

Figure 45:
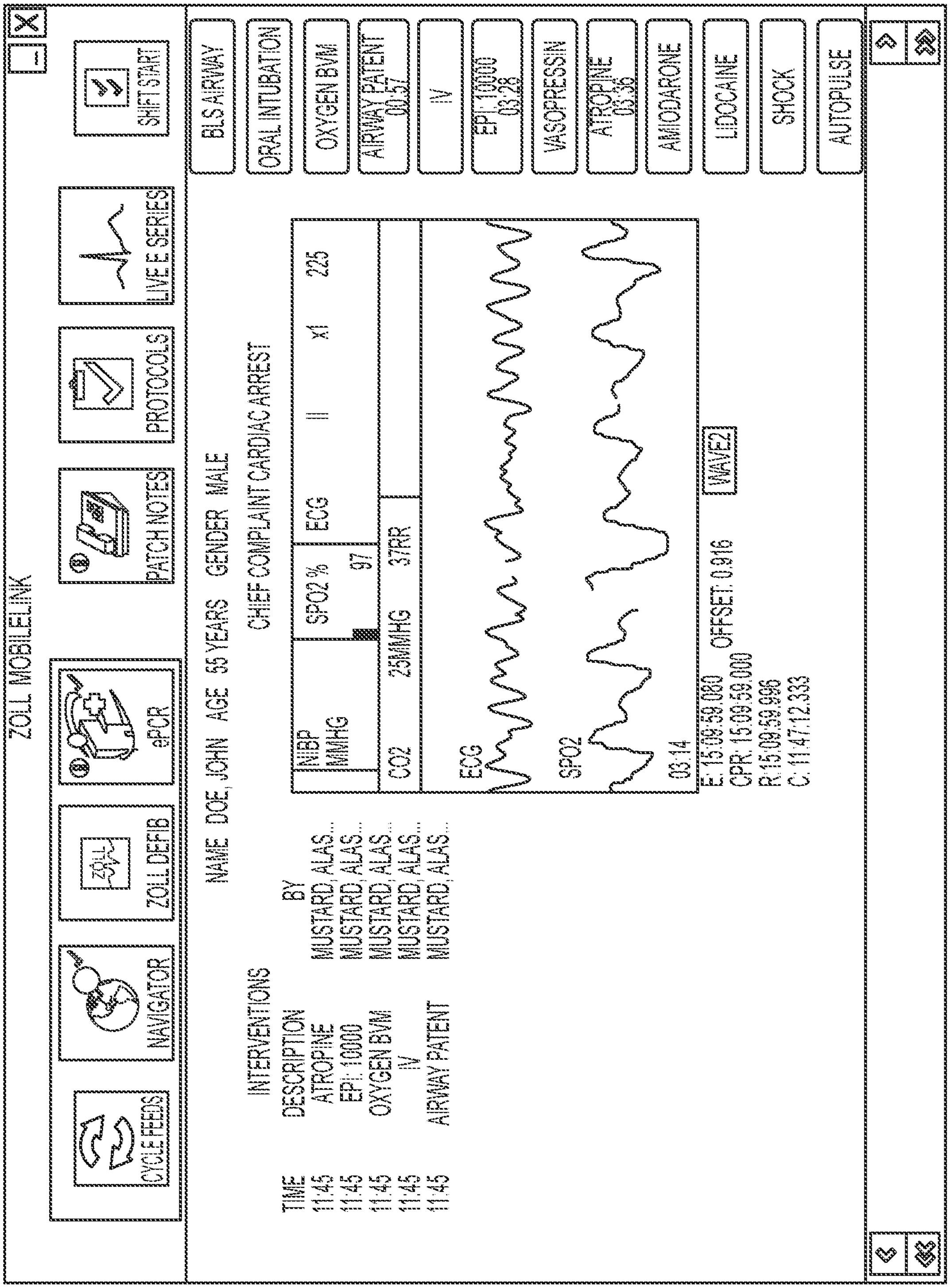
FIG. 45 illustrates a display and graphical user interface displayed when the user selects a live patient data button of a BOA menu template, according to embodiments of the present invention.

FIG. 45 illustrates a display and graphical user interface displayed when the user selects a live patient data button of a BOA menu template, according to embodiments of the present invention. This display includes a list of interventions, a display of patient information, a display of chief complaint, an ECG wave form and/or an SpO2 waveform, as well as a button console (shown as extending vertically on the right side of the screen) listing buttons for available patient interventions, according to embodiments of the present invention. The intervention button console may be dynamic and/or color-coded. The intervention button console may also include timers.

For example, when a patient's airway is checked, the EMS technician activates (e.g. pushes or touches) the "patient airway" button on the intervention button console. The button activates and displays a timer, which counts down to the next time when the patient's airways should be checked. This amount of time may be customized by the user and/or preprogrammed into the BOA module operating the BOA device 104 based on established treatment protocols for the locale in which the patient is treated. Color may also be used; for example, the buttons of the intervention button console may be normally gray, and the "patient airway" button may turn yellow as soon as the button is pushed and the timer activated. The button may turn red within a predetermined amount of time before expiry of the timer, for example one minute before the expiration of the time period being timed. For example, a user may look at the intervention button console of FIG. 45 and see that doses of Epi and Atropine have recently been administered, because those buttons are yellow and their timers activated, while also seeing that the patient's airway was previously checked and is about ready to be checked again, because that button is red. This permits the EMS technician to rapidly visually assess which interventions have been made, as well as which interventions should (or may, according to protocol) be considered in the near future, for any point in time.

Different EMS technicians may have different roles to play in an EMS scenario, based on their training or qualifications, the number of available technicians, and the status of the patient. In the same way, a single EMS technician may need to play multiple roles in an EMS encounter. Such EMS technicians may more effectively and efficiently perform their corresponding tasks if they are presented only with the information related to their particular role, such that they do not see extraneous information which they must mentally process and filter, and such that they are not presented with decision-making or data input options that do not apply to their role. One way in which such role-based information delivery may be accomplished is by providing each EMS technician with a mobile device with software configured to permit an interface with a BOA device 104 based on the user's role.

FIG. 62 illustrates examples of such mobile devices communicably coupled to BOA device 104, including a lead medic mobile device 620, drug medic mobile device 622, airway medic mobile device 624, and CPR medic mobile device 626, according to embodiments of the present invention. According to embodiments of the present invention, each mobile device 620, 622, 624, 626 includes a WiFi transceiver that communicates wirelessly with a WiFi transceiver of BOA device 104.

Figure 46:
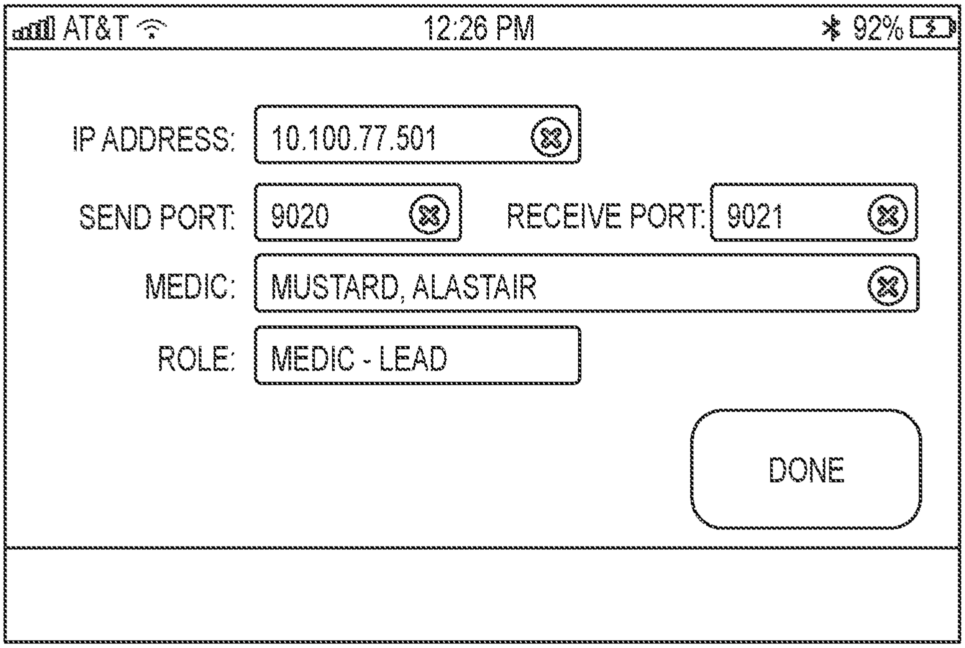
FIG. 46 illustrates a start screen for a role-based EMS technician mobile device in communication with a BOA device, according to embodiments of the present invention.
Figure 47:
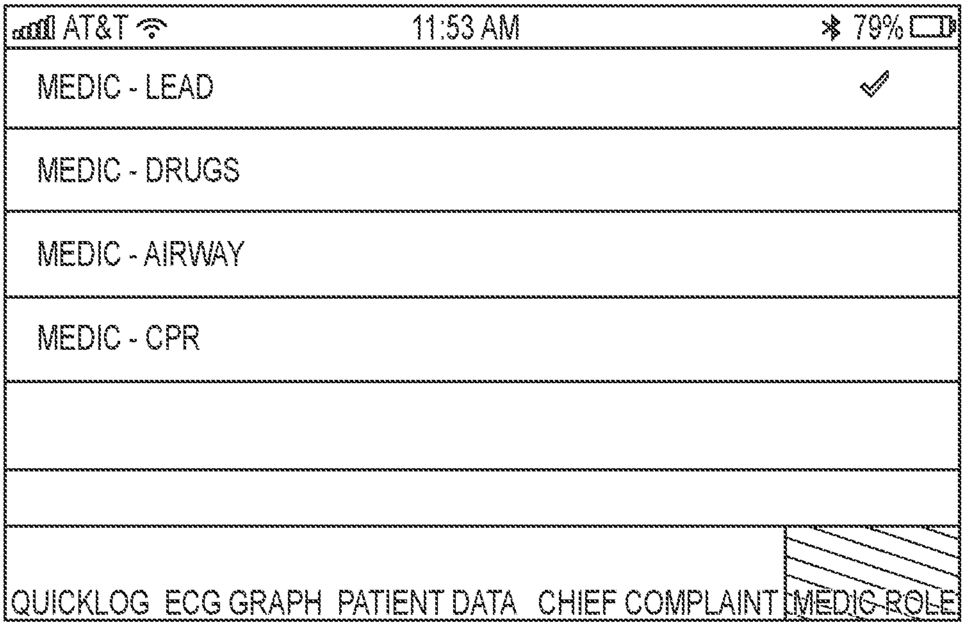
FIG. 47 illustrates a role selection screen for a role-based EMS technician mobile device in communication with a BOA device, according to embodiments of the present invention.

FIG. 46 illustrates a start screen for a role-based EMS technician mobile device 620 in communication with a BOA device 104, according to embodiments of the present invention. The software instructions contained on the mobile device render this start screen to permit the medic to identify the IP Address, send port, receive port, medic name, and medic role, according to embodiments of the present invention. FIG. 47 illustrates a role selection screen for a role-based EMS technician mobile device in communication with a BOA device, according to embodiments of the present invention. A checkmark next to the "Medic-Lead" listing indicates that the user of the mobile device is the lead medic. According to embodiments of the present invention, a password or other authentication may be required in order to restrict role based on identity.

Figure 48:
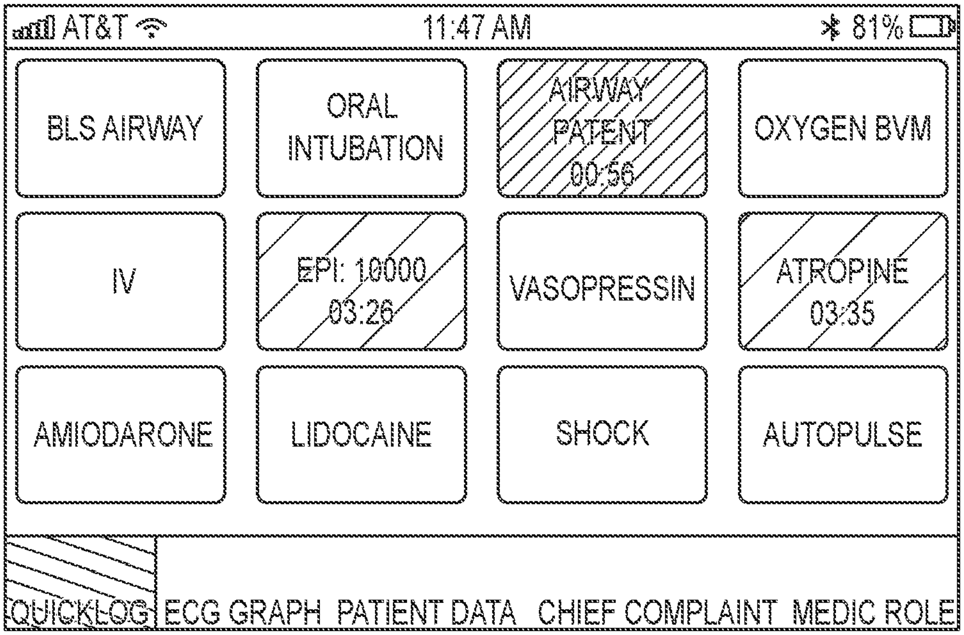
FIG. 48 illustrates a lead medic quick log screen for a role-based EMS technician mobile device in communication with a BOA device, according to embodiments of the present invention.

FIG. 48 illustrates a lead medic quick log screen for a role-based EMS technician mobile device in communication with a BOA device, according to embodiments of the present invention. The mobile device may be configured to display a list of menu options, for example the menu options shown extending horizontally along the bottom of the screen of FIG. 48 permit the lead medic to choose Quick Log, ECG Graph, Patient Data, Chief Complaint, and Medic Role. These options may differ based the user's role. When the lead medic clicks on the Quick Log tab, the lead medic is presented with an intervention button panel, according to embodiments of the present invention. The quick log tab display replicates the intervention button console of the BOA live ECG display of FIG. 45, such that when a lead medic pushes an intervention button on the mobile device via the screen of FIG. 48, the same button (and corresponding timer and/or color) is indicated as being activated in the BOA display screen of FIG. 45, and vice versa, according to embodiments of the present invention.

Figure 49:
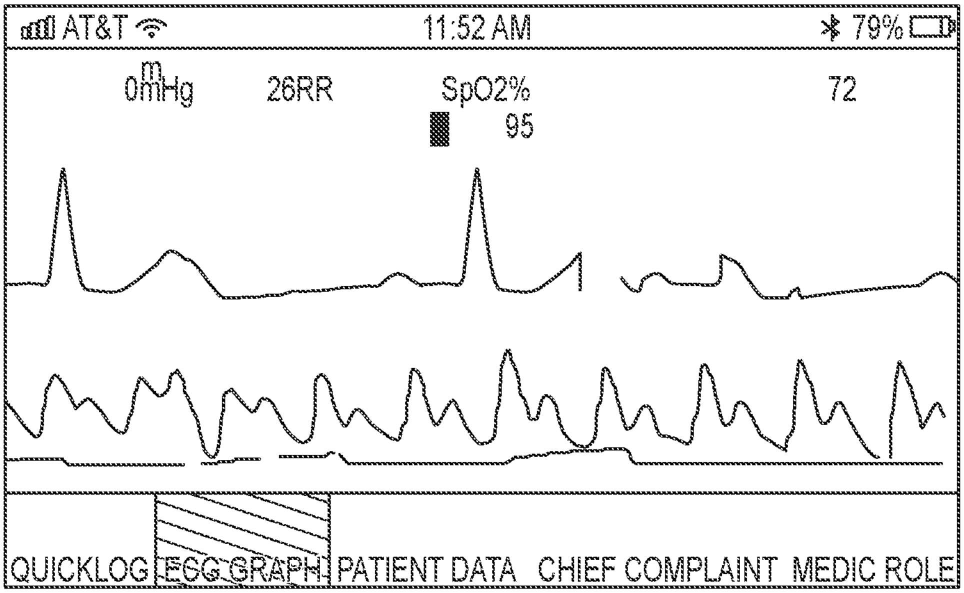
FIG. 49 illustrates a lead medic ECG graph screen for a role-based EMS technician mobile device in communication with a BOA device, according to embodiments of the present invention.
Figure 50:
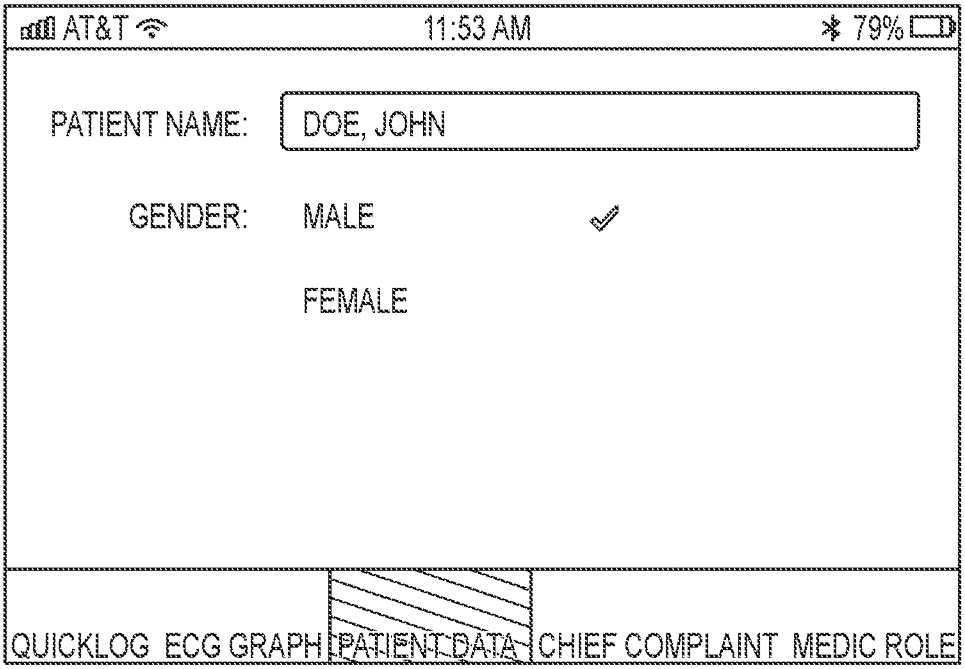
FIG. 50 illustrates a lead medic patient data screen for a role-based EMS technician mobile device in communication with a BOA device, according to embodiments of the present invention.
Figure 51:
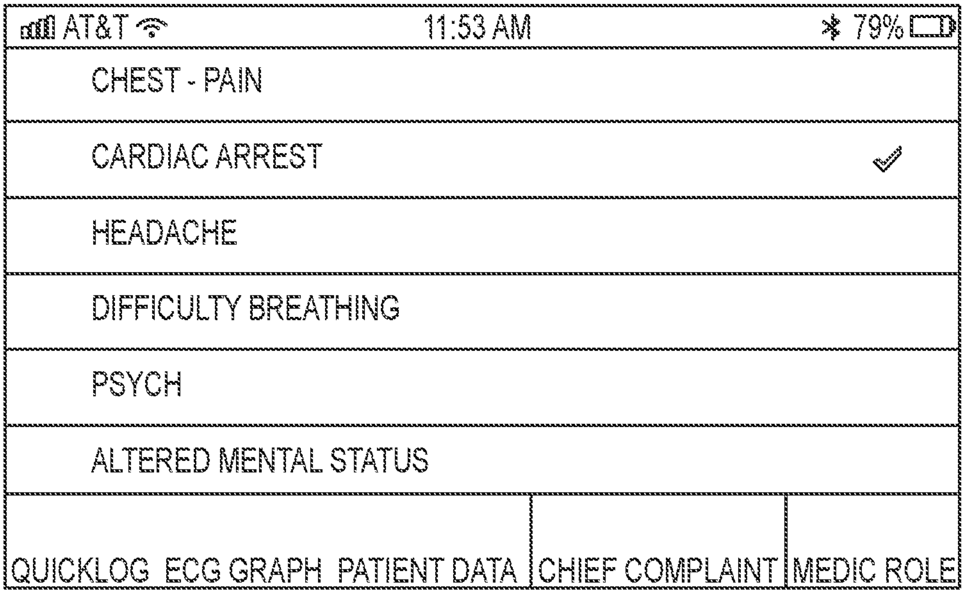
FIG. 51 illustrates a lead medic chief complaint screen for a role-based EMS technician mobile device in communication with a BOA device, according to embodiments of the present invention.

FIG. 49 illustrates a lead medic ECG graph screen for a role-based EMS technician mobile device in communication with a BOA device, according to embodiments of the present invention, which is displayed for the lead medic when the lead medic selects the ECG graph menu button. Because the lead medic's role typically requires a broad swath of patient information, the lead medic ECG graph screen essentially recreates the patient data display screen of the BOA device 104 of FIG. 45, according to embodiments of the present invention. FIG. 50 illustrates a lead medic patient data screen, which permits the lead medic to enter patient information, including the patient's name and gender, according to embodiments of the present invention. FIG. 51 illustrates a lead medic chief complaint screen which permits the lead medic to identify the patient's chief complaint, according to embodiments of the present invention.

Figure 52:
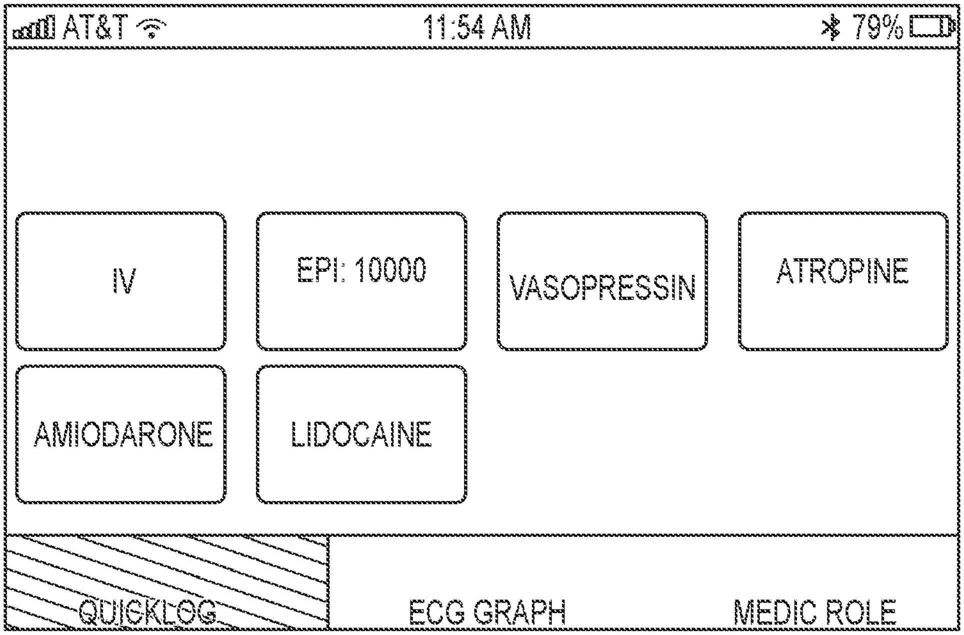
FIG. 52 illustrates a drug medic quick log screen for a role-based EMS technician mobile device in communication with a BOA device, according to embodiments of the present invention.
Figure 53:
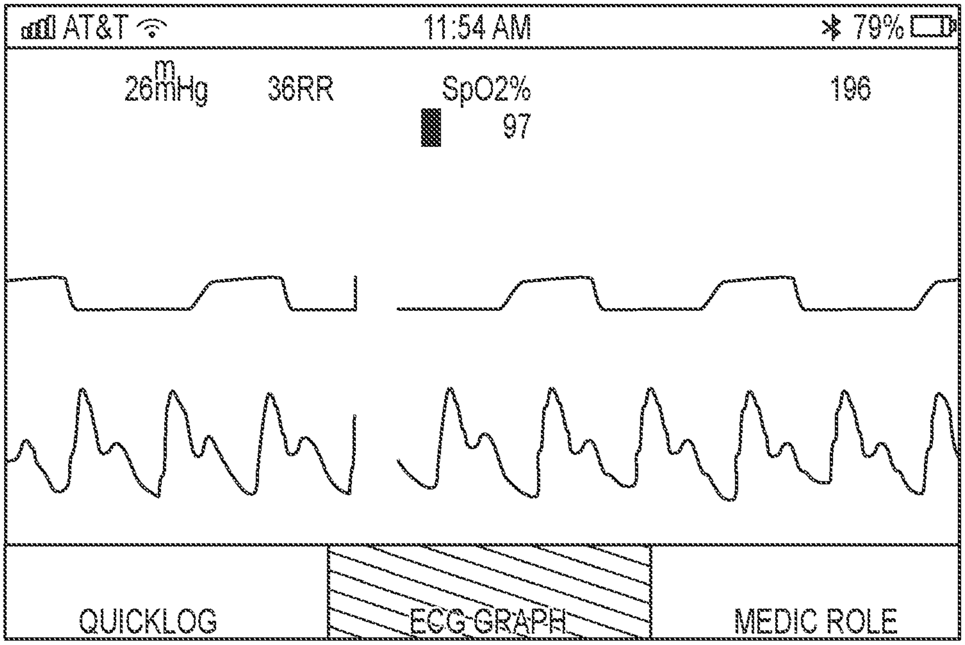
FIG. 53 illustrates a drug medic ECG graph screen for a role-based EMS technician mobile device in communication with a BOA device, according to embodiments of the present invention.

FIG. 52 illustrates a drug medic quick log screen and FIG. 53 illustrates a drug medic ECG graph screen for a medic who has identified his or her role as drug medic, according to embodiments of the present invention. Because the medic has identified a role of drug medic, the quick log screen presents only a subset of the interventions which relate to drugs, according to embodiments of the present invention. Although the drug medic role accesses only a subset of the full set of intervention buttons, the same intervention buttons are tied together across the entire platform, according to embodiments of the present invention. For example, if the drug medic indicates that a dose of atropine has been given by tapping the atropine intervention button on his mobile device 622, the atropine button will turn yellow as activated, and begin a timer, not only on his mobile device 622, but also on atropine buttons of the quick log screen of the lead medic device 620 and on the intervention button console of the BOA device 104 display, as well as any other devices whose quick log screens include the atropine intervention button, according to embodiments of the present invention.

Figure 54:
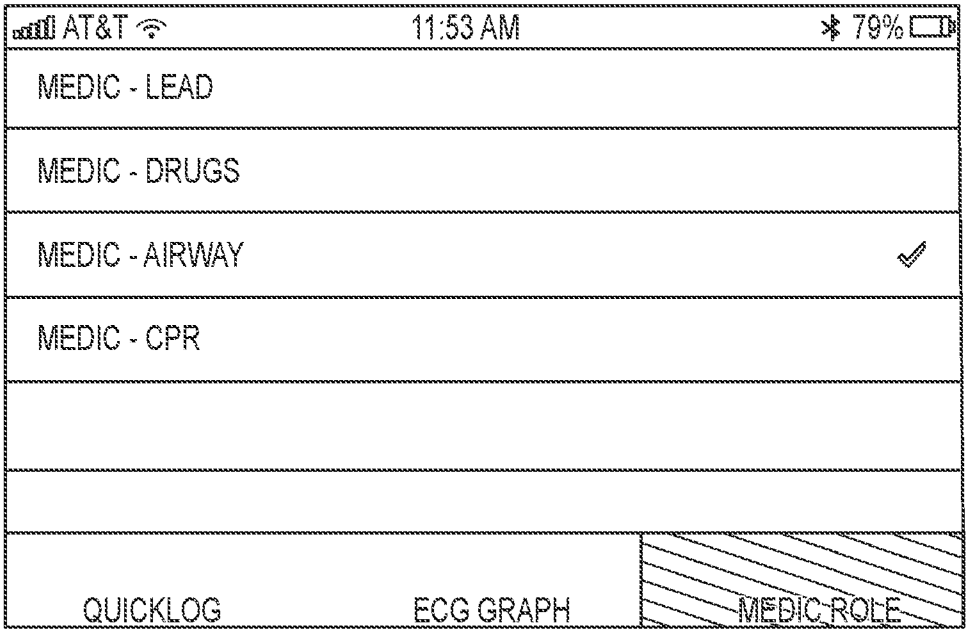
FIG. 54 illustrates a role selection screen for a role-based EMS technician mobile device in communication with a BOA device, according to embodiments of the present invention.
Figure 55:
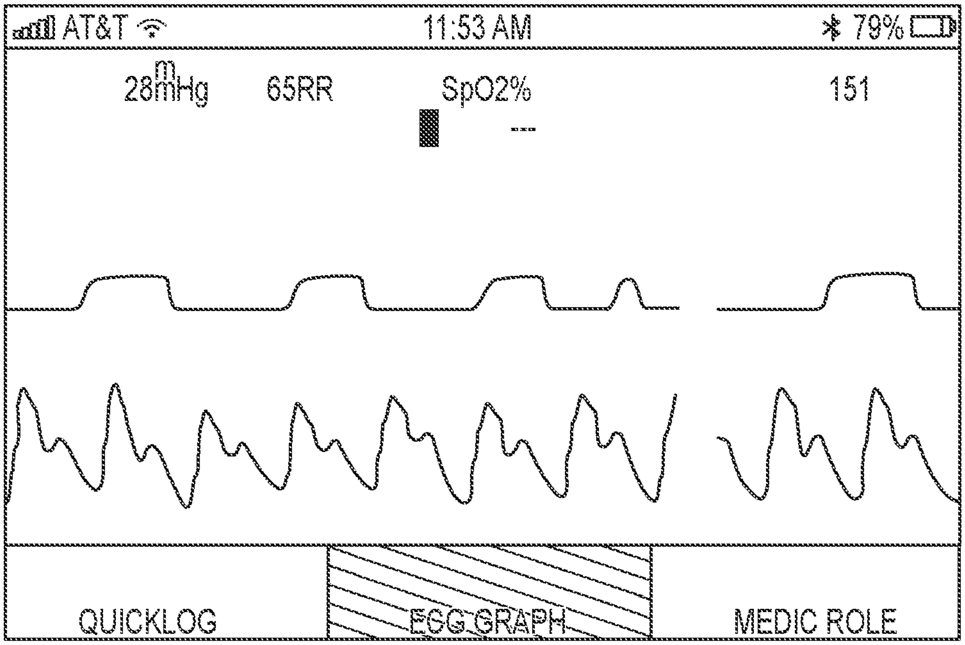
FIG. 55 illustrates an airway medic ECG graph screen for a role-based EMS technician mobile device in communication with a BOA device, according to embodiments of the present invention.
Figure 56:
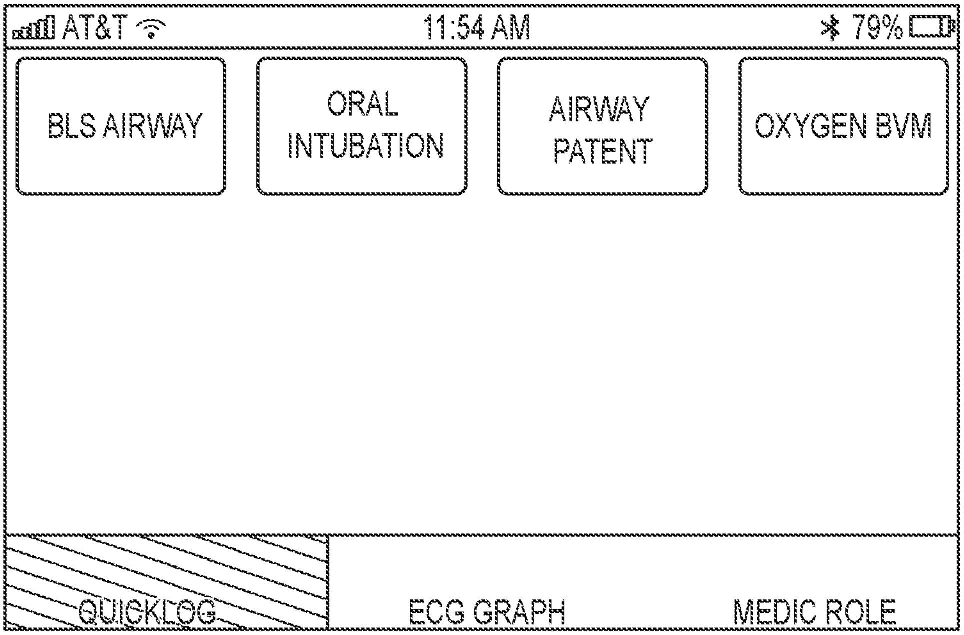
FIG. 56 illustrates an airway medic quick log screen for a role-based EMS technician mobile device in communication with a BOA device, according to embodiments of the present invention.

FIG. 54 illustrates a role selection screen in which an airway medic role has been identified (e.g. by tapping or otherwise selecting that option on the mobile device 624). FIG. 55 illustrates an airway medic ECG graph screen, and FIG. 56 illustrates an airway medic quick log screen listing the subset of interventions that relate to the airway medic's role, according to embodiments of the present invention.

Figure 57:
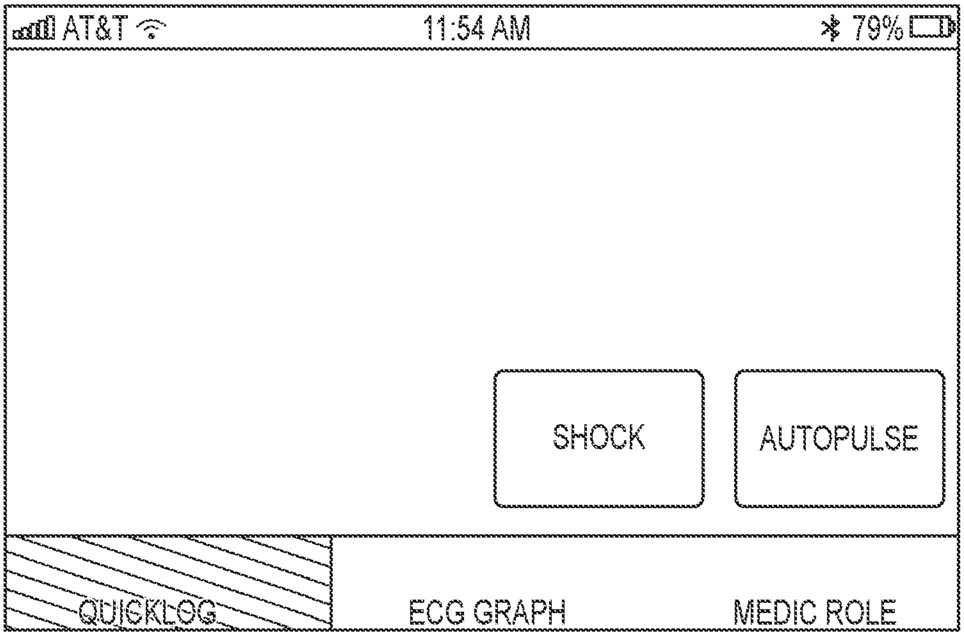
FIG. 57 illustrates a CPR medic quick log screen for a role-based EMS technician mobile device in communication with a BOA device, according to embodiments of the present invention.
Figure 58:
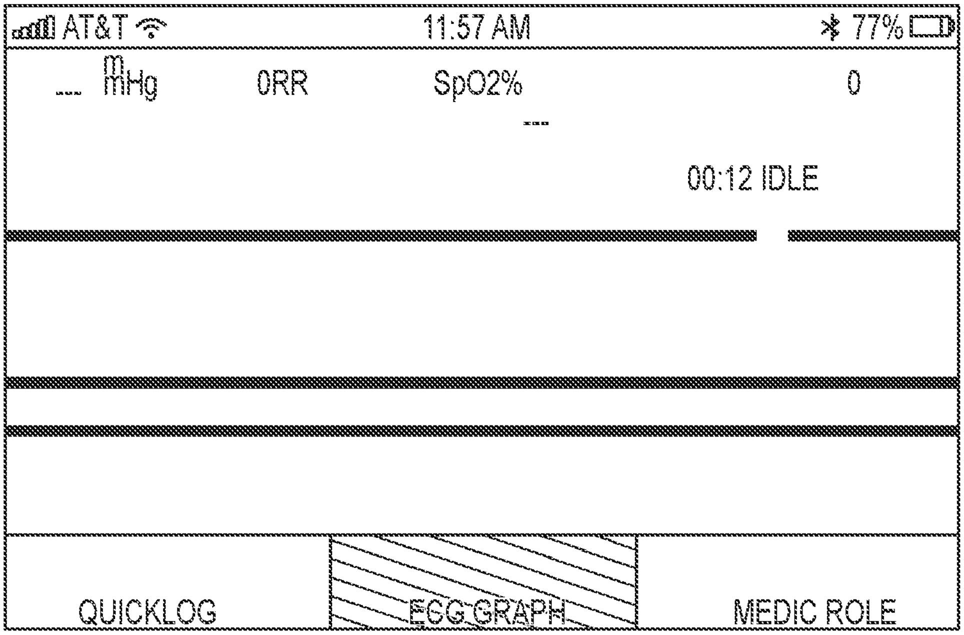
FIG. 58 illustrates a CPR medic ECG graph screen during idle for a role-based EMS technician mobile device in communication with a BOA device, according to embodiments of the present invention.
Figure 59:
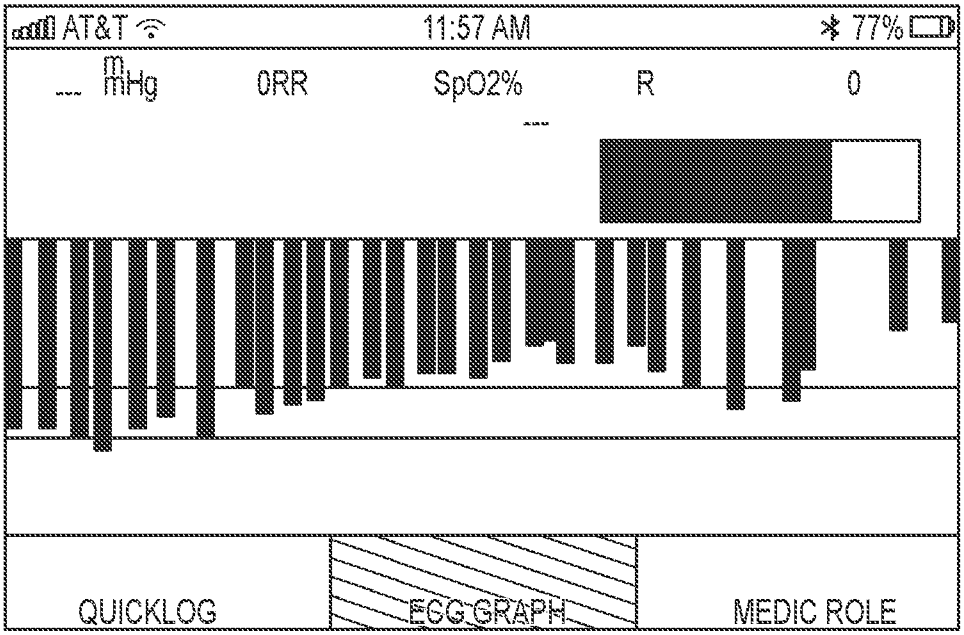
FIG. 59 illustrates a CPR medic ECG graph screen during administration of compressions for a role-based EMS technician mobile device in communication with a BOA device, according to embodiments of the present invention.
Figure 60:
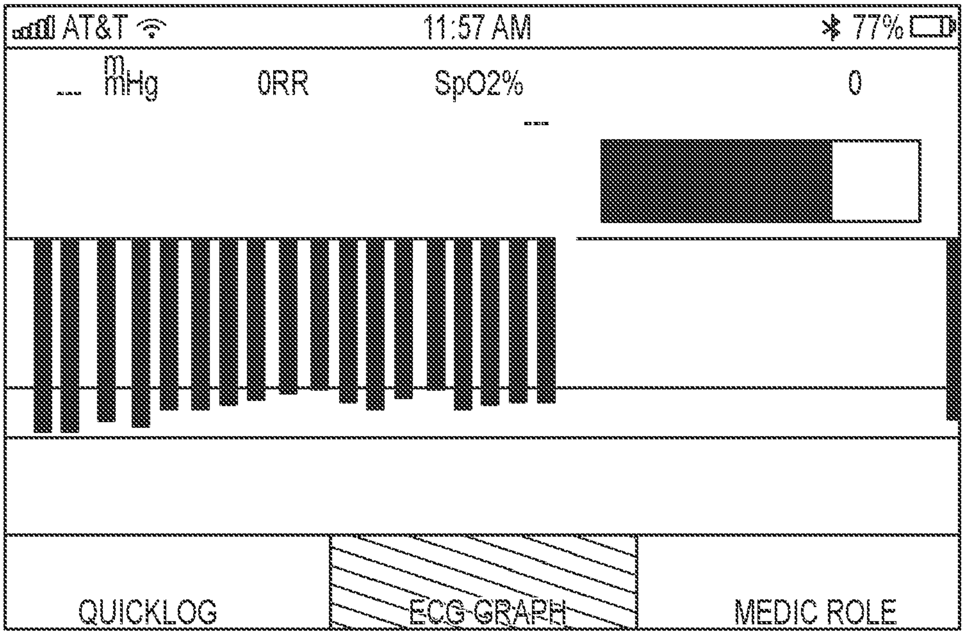
FIG. 60 illustrates a CPR medic ECG graph screen during administration of compressions for a role-based EMS technician mobile device in communication with a BOA device, according to embodiments of the present invention.
Figure 61:
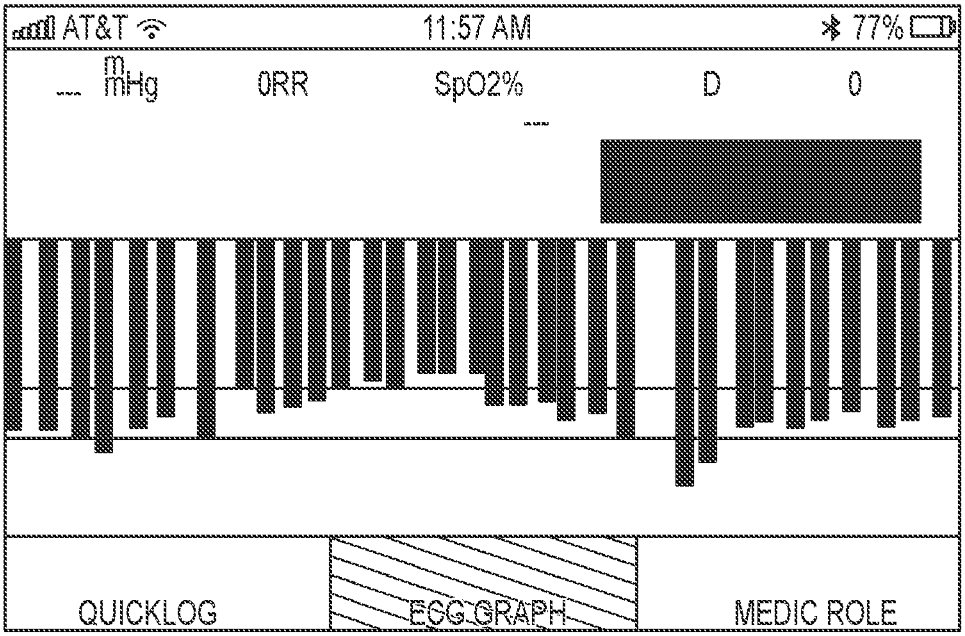
FIG. 61 illustrates a CPR medic ECG graph screen during administration of compressions for a role-based EMS technician mobile device in communication with a BOA device, according to embodiments of the present invention.

FIG. 57 illustrates a CPR medic quick log screen illustrating a subset of interventions that relate to the CPR medic's role, according to embodiments of the present invention. FIG. 58 illustrates a CPR medic ECG graph screen during idle for a role-based EMS technician mobile device in communication with a BOA device, according to embodiments of the present invention. FIGS. 59-61 illustrate a CPR medic ECG graph screen during administration of compressions, which do not show the ECG wave form but instead show measurement and/or evaluation of chest compressions (because the CPR medic is concerned primarily with resuscitation), according to embodiments of the present invention. The CPR feedback provided by the screen interface of FIGS. 58-61 may take many different forms. For example, as illustrated in FIG. 59, vertically descending bars may be used to represent depth of each chest compression, spaced horizontally in a manner along a time axis. The chest compression bars descend from an axis toward another set of axes, which specify the desirable or optimal range of depth for each chest compression. A qualitative indicator bar, shown in the upper right, gives the user a combined visual feedback relating to depth and rate of chest compressions; a full box means that both the rate and depth are within desired limits. The letter "R" on FIG. 58 indicates a potential alert regarding the rate of the chest compressions, and the letter "D" on FIG. 61 indicates a potential alert regarding the depth of chest compressions, according to embodiments of the present invention. According to embodiments of the present invention, the CPR feedback screen of device 626 provides information about the rate and volume of patient ventilation.

According to embodiments of the present invention, the patient monitoring device 106 and/or EMS communications interface device 2000 and/or the BOA device 104 includes a filtering mechanism (e.g. a circuit or processing instructions) that filters or removes chest compression interference from ECG signal data. Embodiments of the present invention may include a device or utilize a method similar to those described in U.S. Pat. No. 7,295,871, issued Nov. 13, 2007, which is incorporated by reference herein. Embodiments of the present invention may also employ Real CPR Help® technology available from Zoll Medical Corporation.

The use of role-based information delivery and intervention tracking permits a more efficient EMS treatment scenario by filtering data based on role, according to embodiments of the present invention. For example, the drug medic, airway medic, and CPR medic do not have menu tab selections available for patient data entry or for chief complaint entry, while the lead medic has those options.

Although only four mobile devices 620, 622, 624, and 626 are shown in FIG. 62, the BOA device 104 may communicably couple with a greater or fewer number of role-based mobile devices. Also, although particular intervention options and data feed displays are shown as being related to particular roles, one of ordinary skill in the art, based on the present disclosure, will appreciate the numerous different roles that may be identified and implemented, as well as the numerous different data feeds and/or options that may be associated with each role. Further, mobile devices (e.g. 620) may be configured to communicably couple with multiple BOA devices 104 and/or to receive information for multiple patients from the same BOA device 104, to permit the medic to toggle between various patient data feeds and/or to treat different patients, possibly in different roles, according to embodiments of the present invention.

According to embodiments of the present invention, the software modules and hardware contained within the BOA device 104 for feeding the data to and from the mobile devices 620 may be consolidated into an EMS communications interface device 2000, and/or directly into a patient monitoring device 106.

Figure 63:
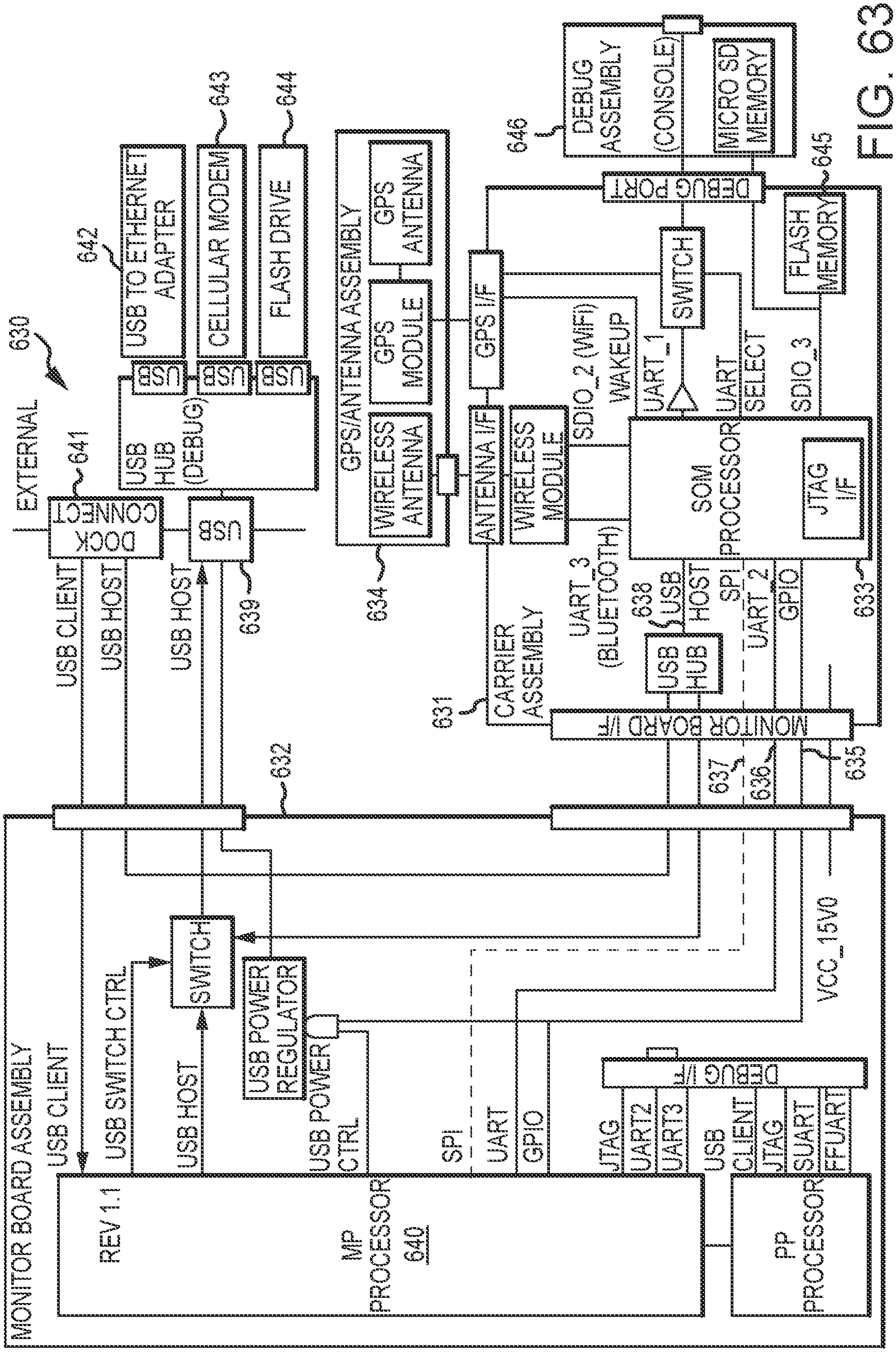
FIG. 63 illustrates an information system including an EMS communications interface device, according to embodiments of the present invention.
Figure 64A:
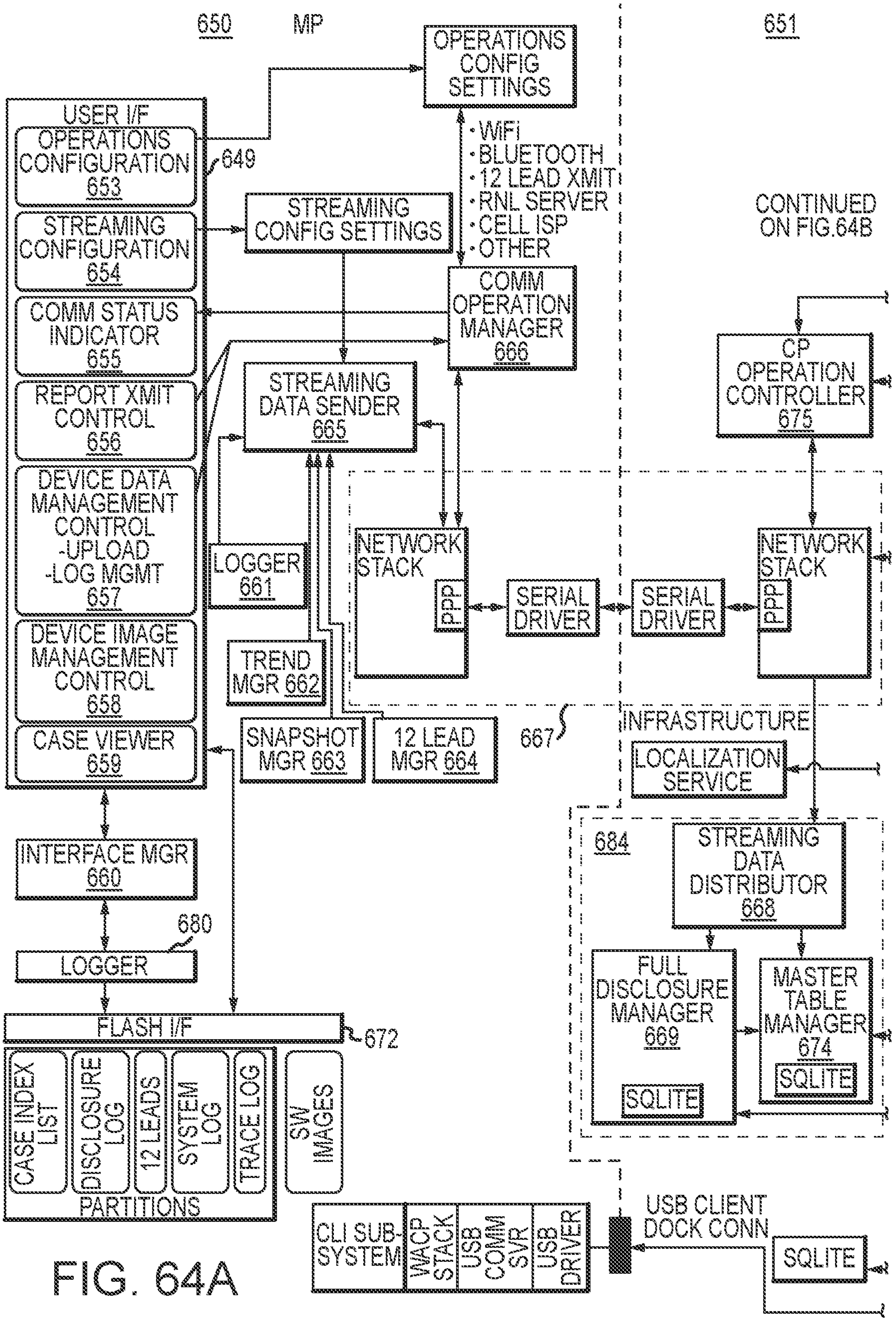
FIGS. 64A and 64B illustrate a software system architecture for an EMS communications interface device and underlying patient monitoring device, according to embodiments of the present invention.
Figure 64B:
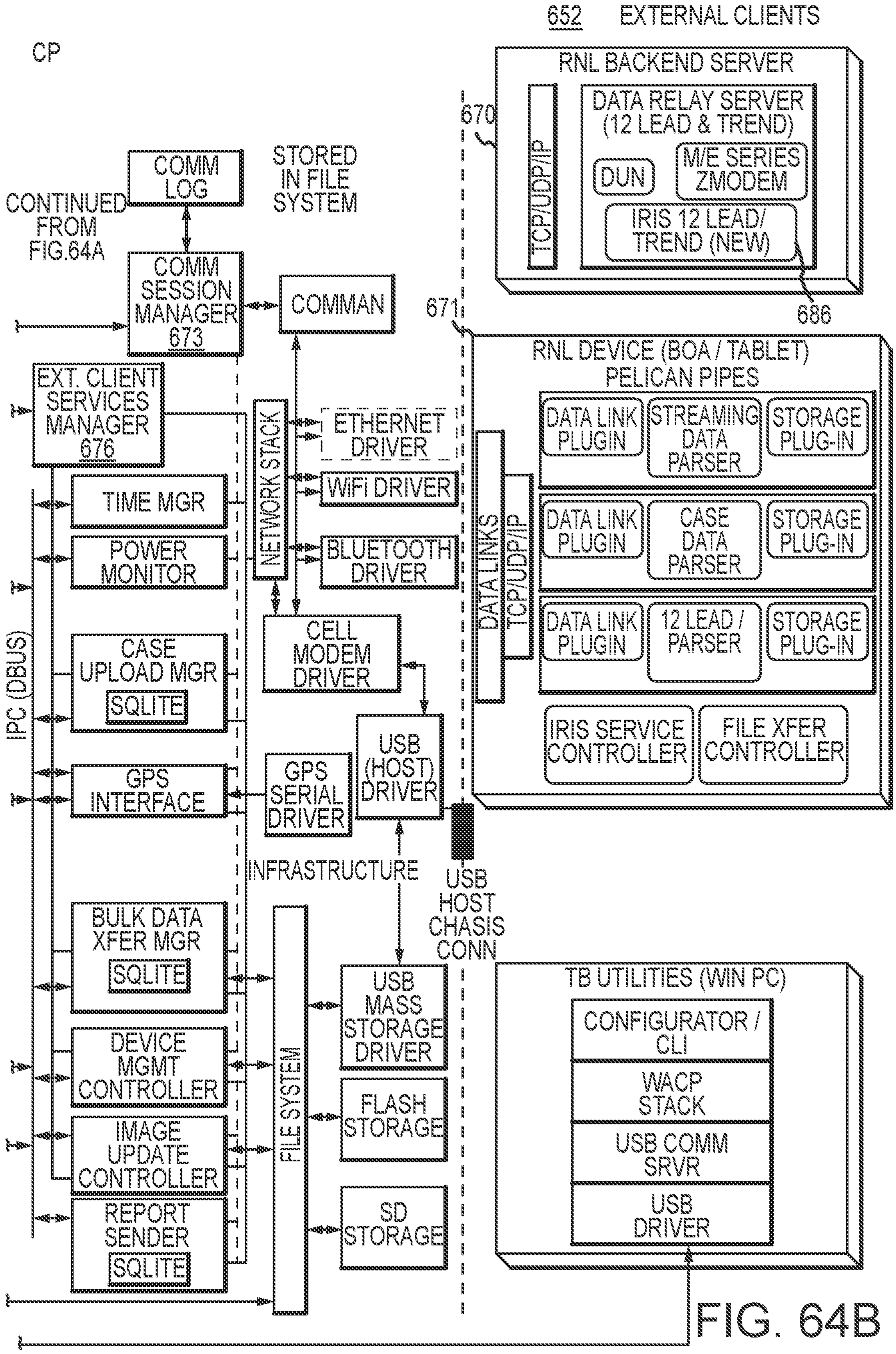

FIGS. 63 and 64 illustrate an EMS communications interface device 631 which may be used as an alternative to device 2000 (described above) for enabling one- or two-way communication between a patient monitoring or clinical device 106 and the BOA system 104 or other devices such as an enterprise application server 128 through the network 120, according to embodiments of the present invention. Existing defibrillator devices sometimes permit a serial cable connection to an information system for limited information transfer, but are not typically able to provide streaming data about a patient to other devices, or stream patient data via Wi-Fi, or provide transparent, easy-to-use, and automatic linking of information to one or more devices within an EMS setting, such as an emergency transport vehicle 101.

FIG. 63 illustrates a system 630 which includes a carrier assembly 631 that is able to receive clinical patient data from a processor 640 on a monitor board assembly 632 of a defibrillator device, according to embodiments of the present invention. Although the carrier assembly 631 is described as operating with a defibrillator device to receive, process, store, and transmit information, one of ordinary skill in the art will appreciate, based on the present disclosure, that the carrier assembly 631 may be used in conjunction with patient monitoring and treatment devices other than defibrillator devices. Normally, the data processed and results or graphics generated by the processor 640 are stored locally on the defibrillator device or displayed locally on the defibrillator device. Without the EMS communications interface device 631, a user can make a copy of the internally stored data to a portable memory device (e.g. a USB memory stick) which can then be physically transported to a processing device with an appropriate application for post-case viewing. The user is unable to view, store, display, or use the information from the defibrillator in other devices during the actual monitoring or treatment of the patient. Thus, being able to retrieve case data about patient encounters long after the encounter has ended, does not facilitate instantaneous, streaming, and/or real-time communication among EMS clinical and non-clinical devices.

The EMS communications interface device 631 thus is communicably coupled with the processor 640 of the defibrillator, so that it can receive clinical data from the processor as the clinical data is generated, and/or as the patient monitoring progresses. The EMS communications interface device 631 includes a processor 633, which may be a SOM processor, which is communicably coupled with processor 640 via one or more connections or types of information exchange, for example a general purpose input/output (GPIO) line 635, a universal asynchronous receiver-transmitter (UART) line 636, and/or a serial peripheral interface (SPI) line 637, according to embodiments of the present invention. In some embodiments, GPIO line 635 does not convey data, but only conveys state information for the synchronization with SOM processor 633. The EMS communications interface device 631 may include a flash memory storage element 645, and also includes or is communicably coupled with a GPS and antenna assembly 634. The SOM processor 633 may also include a USB Host line 638 which may connect to an external USB hub 639 and/or to devices such as a USB to Ethernet Adapter 642, a cellular modem 643, and/or an external flash drive 644, according to embodiments of the present invention. The SOM processor 633 may also include a USB connection to a docking connection station 641 to permit docking of another device with the USB ports of the two devices. A debugging assembly 646 is shown as an optional assembly for testing purposes.

FIG. 64 illustrates an information flow diagram among software modules which may implement the communication functionality described with respect to FIG. 63, according to embodiments of the present invention. FIG. 64 illustrates three different software domains 650, 651, 652 which, although they correspond roughly to the hardware domains described with respect to FIG. 63, may include executable instructions contained on, and/or processors contained on, a wide array of devices either locally or remotely, and may also include processing steps carried out on a distributed array of devices, according to embodiments of the present invention.

The monitor domain 650 illustrates modules operating with respect to defibrillator and/or patient monitoring device functionality, according to embodiments of the present invention. For example, the user interface module 649 includes various modules that permit the defibrillator and/or patient monitoring device user, interacting via the defibrillator interface screen and/or buttons, to view data and/or make selections. The operations configuration module 653 permits a user to configure the operational setting of the data transmission; for example, module 653 permits the user to configure the settings for WiFi operations, blue tooth operations, cellular operations, and connections to enterprise storage servers 126, among other configuration settings. This setting information is sent to a communications operation manager 666 which sends the information via network interface 667 to the CP operation controller 675. The CP operation controller 675 works with the external client services manager 676 and the communication session manager 673 to enable the transmission modes for use by other managers in the EMS communications interface device 631.

The streaming data sender module 665 receives input from a logger module 661, a trend manager module 662, a snapshot manager 663, and a twelve lead manager 664, according to embodiments of the present invention. The logger module receives patient events such as vital measurement readings, changes in alarm state, defibrillation actions, and logs them in local persistent memory and sends them to the streaming data sender. The trend manager module captures all patient vital sign information on a configured periodic basis, and records them in local persistent memory as well as sending them to the streaming data sender. The snapshot manager collects wave data associated with an event for a window of time around the event. It also records the vital signs at the time of the event. It stores all this data in local persistent memory as well as sends it to the streaming data sender. The 12 Lead Manager captures the ECG waveforms clinically known as a “12 Lead” along with analysis data of the waveforms. It stores all this data in local persistent memory as well as sends it to the streaming data sender. The streaming data sender transmits the data it receives from each of these managers to the Streaming Data Distributor 668 on the communications interface device 631.

As clinical data is generated by processor 640, a logger module 680 pulls out data according to certain criteria and parses and/or saves the data in partitions via flash interface 672, according to embodiments of the present invention. For example, portions of the clinical data may be stored, including a case index list, a disclosure log, a set of twelve leads gathered, a system log, and a trace log.

The communication status indicator module 655 displays to the user the communication status received from the communications operation manager module 666. The report transmit control module 656 provides a Graphical User Interface (GUI) so the user can select reports, such as 12 lead data reports, and initiate the transmission of such reports to an external receiver. This is accomplished by sending a control message to the comm operation manager 666 which sends it through the serial network interface 667 to the comm operation controller 675. The comm operation controller 675 then invokes the report sender which reads the stored 12 lead data from the database and transmits it to the requested external destination. The device data management module provides a GUI control menu so a user can select patient full disclosure records or log records for transmission to external devices, and initiate such transmissions. This is accomplished by sending a control message to the comm operation manager 666 which sends it through the serial network interface 667 to the comm operation controller 675. The comm operation controller 675 then invokes the case upload manager which reads the case data from the database and formats and transmits the data through the network interface to the requested external device. A device image management control module 658 permits the user to manage various images captured by the defibrillator device. A case viewer module 659 permits a user to retrieve and display various logged clinical data via flash interface 672, according to embodiments of the present invention.

Once the clinical data is received by the streaming data distributor 668 in the carrier processor domain 651, the streaming data distributor 668 sends the patient data to a full disclosure manager 669 and creates a patient case record in the master table manager 674, according to embodiments of the present invention. These three modules 668, 669, 674 may be referred to as the streaming data handler 684. The streaming data handler 684 processes the raw clinical data from the defibrillator processor 640, and stores the data for later retrieval, and/or for concurrent or snapshot retrieval, according to embodiments of the present invention. According to one embodiment of the present invention, the streaming data handler 684 causes the clinical data arriving from the defibrillator to be stored in flash memory substantially in the same form as it arrives. According to another embodiment of the present invention, the streaming data handler 684 frames the streaming data, for example in a manner similar to that described above with respect to FIGS. 22 and 23. According to other embodiments of the present invention, the streaming data handler 684 sorts the data, and/or picks out selected portions of the data for storage and later streaming (either real-time, substantially real-time, or time-delayed), or for later querying and retrieval, via the wireless and/or USB communications interfaces.

The various software modules and hardware components permit the EMS communications interface device 631 to send data via an Internet Protocol (IP) to a backend server module 670 in the external client domain 652 (e.g. servers 126 or 128), and/or to a subscribing device module 671 (e.g. BOA system 104 and/or patient charting device 108), according to embodiments of the present invention.

According to one embodiment of the present invention, the backend server 126, 128 and/or BOA device 104 permit a user to view and display, in a remote environment such as the back of an ambulance and/or at an enterprise workstation 122, historical snapshots of patient clinical data. This historical snapshot data may be viewed and/or accessed during the same clinical encounter in which it was collected. Such data may be retrieved and/or displayed according to certain criteria, including for example a period of time.

Figure 65:
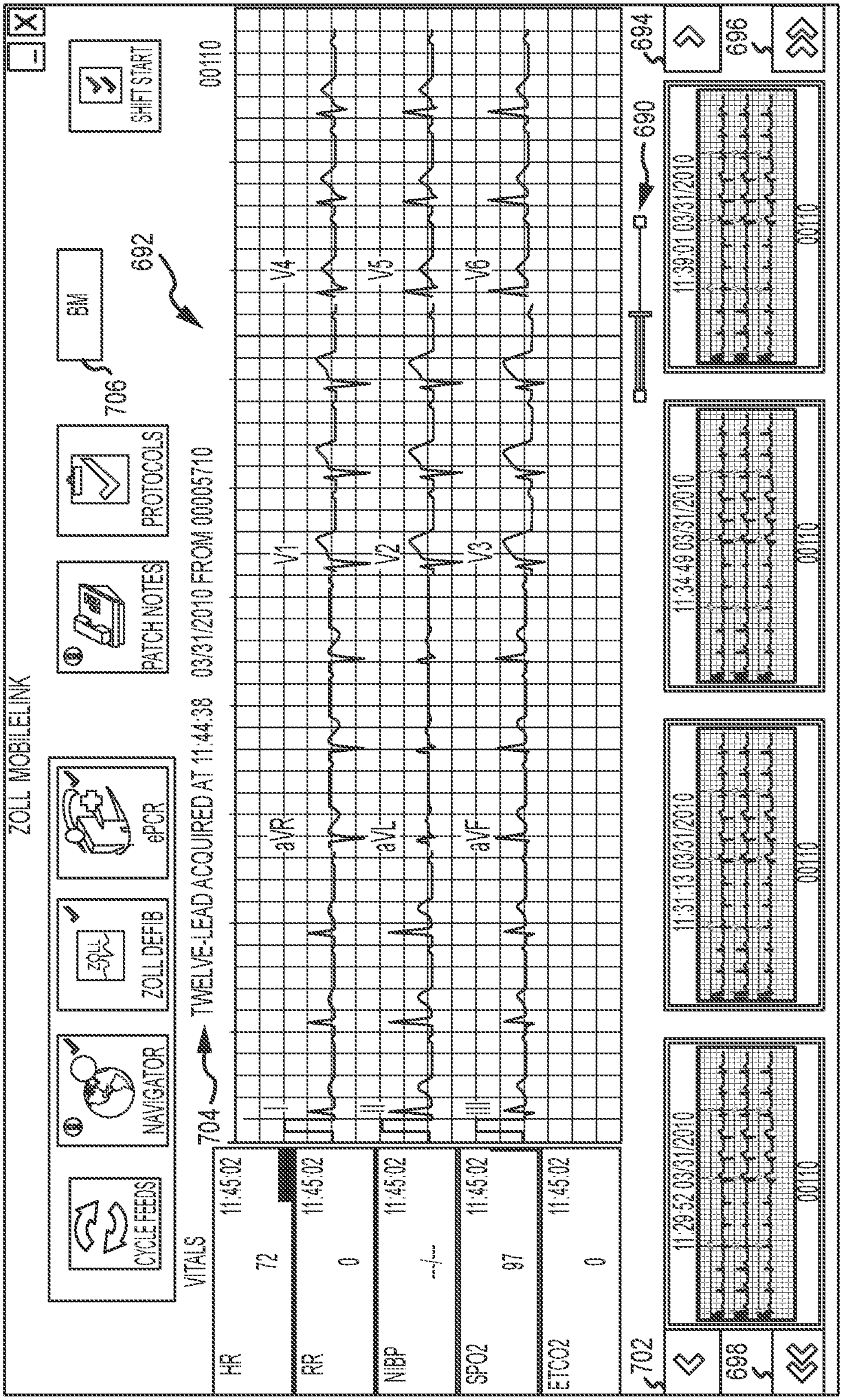
FIG. 65 illustrates a user interface screen for a device subscribed to the EMS communications interface device of FIG. 63, according to embodiments of the present invention.

The backend server module 670 may for example include a twelve lead and/or trend view module 686 which permits accessing of patient twelve-lead data, according to embodiments of the present invention. For example, if an EMS technician 114 is looking at a display of a patient's 12-lead ECG from ten seconds ago, the technician 114 may request to view each 12-lead ECG taken within the last ten minutes, or one 12-lead for each minute of the last ten minutes, in order to better understand how the patient's 12-lead portrayal has changed over that ten-minute period. FIG. 65 illustrates one example of a user interface that may be used to display snapshot 12-lead ECG data, according to embodiments of the present invention. According to some embodiments of the present invention, 12 leads are not continually streamed or provided, but are available when requested. For example, there may be one 12-lead for each minute if requested by the user.

This display may be displayed on BOA device 104, for example. The most recently acquired 12-lead portrayal is displayed in the main position 692, while previous 12-leads acquired in the past appear as smaller graphics or thumbnails along the bottom of the display, as illustrated in FIG. 65. In the example shown, the thumbnail for the more recently acquired 12-lead appears on the right, while each thumbnail toward the left represents successively earlier snapshots of the patient's 12-lead signal. According to some embodiments of the present invention, the thumbnails of historical 12-lead snapshots are themselves readable and legible on the display. According to some embodiments, when a user selects or touches or clicks on a 12-lead thumbnail image, the selected 12-lead is enlarged and displayed in the main position 692. In such cases, the display may be configured to indicate to the user that the currently displayed 12-lead image is not the most recently acquired; for example, the background color may change to red when a historical snapshot 12-lead is positioned in the main display 692, while changing back to gray or white when the most recently acquired 12-lead is positioned in the main display position 692. A time notification 704 may also be displayed to indicate the time and/or date of the currently displayed or currently enlarged 12-lead capture, according to embodiments of the present invention.

The buttons 694 and 702 may be pushed or selected in order to advance the line of thumbnails forward or backward in time, for example one by one, according to embodiments of the present invention. The double arrows button 696 may be pushed or activated in order to advance the line of thumbnails to show the most recently acquired 12-lead in the right-most position of the thumbnails, and the double arrows button 698 may be pushed or activated in order to advance the line of thumbnails to show the oldest acquired 12-lead (in the left-most position of the thumbnails), according to embodiments of the present invention. The double arrows 696, 698 may alternatively operate to transition data in a paged manner, such that pressing the double arrow buttons 696, 698 shifts the view to the next set of thumbnails (e.g. if four thumbnails are shown, the next page includes the next chronological set of four thumbnails). The thumbnails may also be arranged chronologically in the opposite direction.

The user interface may also include an input area permitting the user to specify the time frame over which the 12-lead thumbnails are displayed, or to otherwise sort or narrow the thumbnail display, according to embodiments of the present invention. For example, slider bar 690 may be adjusted left or right to augment or shrink the time period over which 12-lead thumbnails are displayed at the bottom of the screen. If the time period is increased, then the display may be refreshed to include additional 12-lead thumbnails corresponding to the time period (e.g. by shrinking the size of each thumbnail to fit more on the screen, and/or by adding additional rows of thumbnails), or the size of each thumbnail may remain the same but the system selects a representative thumbnail from periodic subsets of the total set of 12-leads satisfying the time criteria, according to embodiments of the present invention. Other filters for the 12-lead dataset may include a clinical event filter, or a user-requested filter. And although 12-lead snapshot datasets are illustrated, a similar display and user interface process may be employed for other sets of clinical and/or non-clinical data, according to embodiments of the present invention. The SOM processor 633 may further be configured to receive, store, and transmit audio and video data, such as, for example, audio and video stream data, to external subscribed devices such as BOA system 104, according to embodiments of the present invention.

The display may also include a bookmark button 706 which permits a particular 12-lead representation to be flagged for later easy retrieval. In some embodiments, a thumbnail may be selected and dragged over to the bookmark button in order to bookmark the particular thumbnail. Another button (not shown) may permit the display to be filtered to show only bookmarked 12-lead images. According to some embodiments of the present invention, each 12-lead thumbnail display includes the date and time when it was recorded.

The display and user interface of FIG. 65 may also be available to an enterprise user 124 via an enterprise workstation 122, such that a doctor or other healthcare professional at a remote location (e.g. the hospital) can view thumbnails and historical clinical data for a patient while the patient is being transported and/or treated, for example via a web browser interface, prior to the patient arriving at the hospital. According to one embodiment of the present invention, the BOA device 104 screen and/or the enterprise workstation 122 may view more than one patient on the same screen, and/or tiled or split screens containing similar information for multiple patients, in order to track activity across the spectrum of units in service, and/or to handle a mass casualty situation.

In some embodiments, the BOA device 104 or other external device may query any 12-lead snapshot data set contained on the communications interface device 631 and subsequently process, sort, and/or filter the data; in other embodiments, the SOM processor 633 has already sorted, filtered, and/or selected the appropriate or most relevant 12-lead images and/or sets of data, which the BOA device 104 or other external device may access and display more rapidly, without having to do its own processing on the data.

Figure 66:
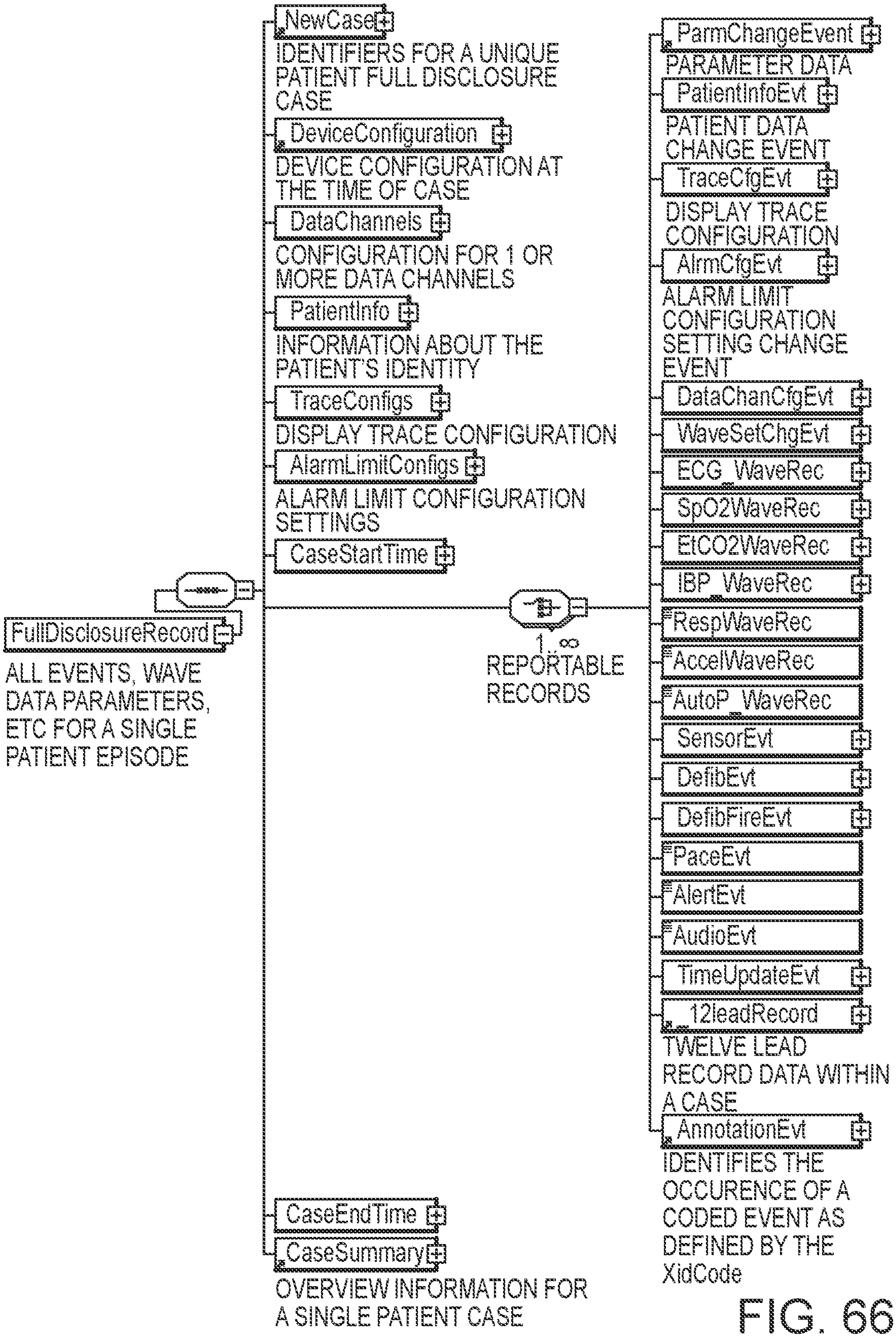
FIG. 66 illustrates a full disclosure document XML schema used by the EMS communications interface device of FIG. 63, according to embodiments of the present invention.
Figure 67:
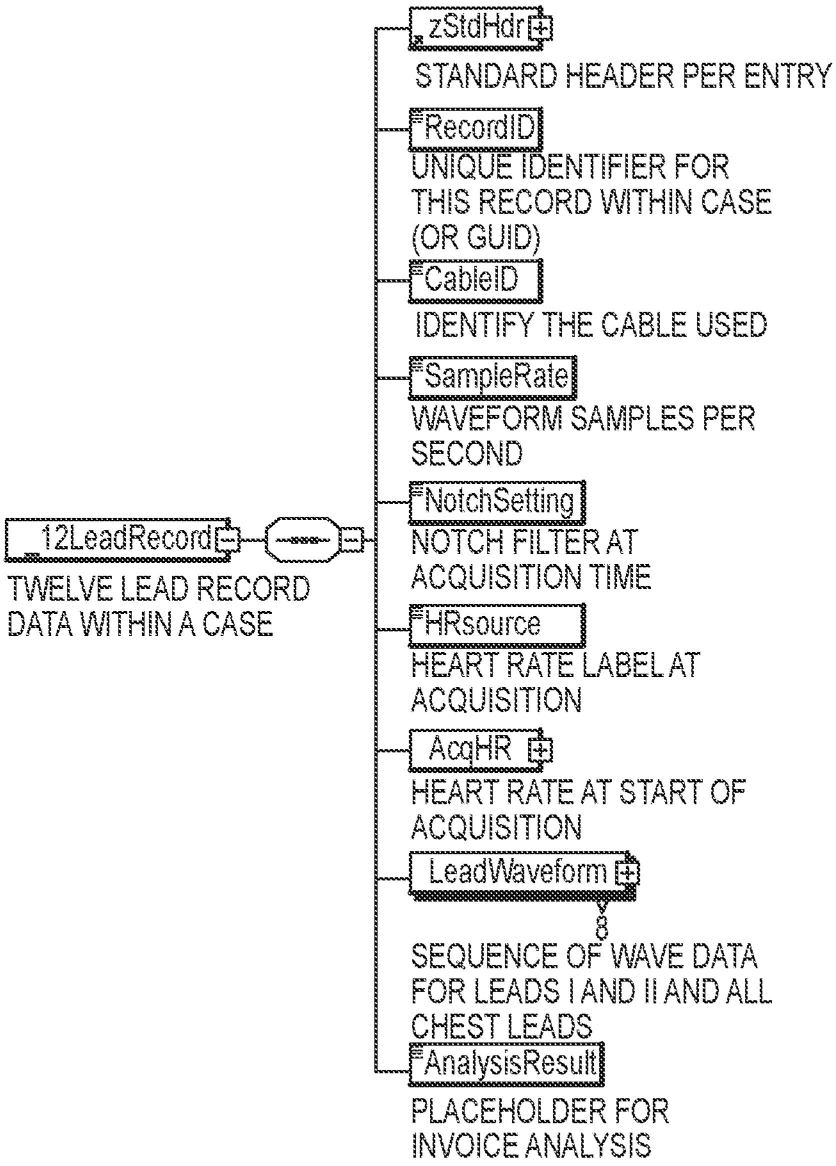
FIG. 67 illustrates a diagram of a twelve-lead data element in the XML schema of FIG. 66, according to embodiments of the present invention.

According to embodiments of the present invention, the SOM processor 633 formats the raw data received from the defibrillator according to an XML schema, which may be requested by subscribed devices and supplied as an XML object over internet protocol connections. FIG. 66 illustrates one example of a Full Disclosure Record schema, with each child corresponding to a particular kind of data. FIG. 67 illustrates a diagram of the 12LeadRecord element of the Full Disclosure record of FIG. 66. According to some embodiments, clinical EMS information is transmitted by EMS communications interface device 631 in a customized XML format; according to other embodiments, EMS communications interface device 631 stores and can transmit EMS information from the patient monitoring device 106 according to a defined standard, such as the National EMS Information System (NEMSIS) standard format. According to embodiments of the present invention, the data received by device 631 over the serial connection with processor 640 is stored in an SQLite database, with each case forming a separate file, along with a case directory database table managed by the master table manager 674 which tracks each case stored on the device 631.

Devices can connect with system 630, and particularly system 631, in several ways. For example, a device (e.g. BOA device 104) can connect to system 631 via a "back office" enterprise server, such as server 126 or 128 (see FIG. 1). System 631 can establish a connection with servers 126, 128 in several ways, for example: using a USB cellular modem 643 plugged directly into USB port 639, which is also connected to an Internet Service Provider, or using a Bluetooth® connection to a cellular device (e.g. a phone) that can then connect to an Internet Service Provider, or using a Wi-Fi connection to a cellular modem that can then connect to an Internet Service Provider. In each case, a data connection is made over a cellular link to the carrier's Internet Service Provider, and then EMS communications interface device 631 uses standard communication Internet Protocols to connect with, authenticate, and interact with the server 126, 128, according to embodiments of the present invention.

As another example, an external device (e.g. BOA 104 and/or patient charting device 108) can use a discovery protocol, for example mDNS/DNS-SD, to probe a local system 631 to determine which data services it provides. The external device would then form a TCP/IP connection to that service on the communication interface system 631. According to embodiments of the present invention, each communication interface system 631 has a unique IP socket address. Both the communication interface system 631 and the external device would then authenticate each other to permit bi-directional commands, responses, and data flow. This data flow may occur in XML format over a TCP/IP protocol, for example. This discovery protocol could also operate in reverse, such that the communications interface device 631 could probe external devices (e.g. BOA 104) and connect to services on those devices, according to embodiments of the present invention. In these ways, external devices may be connected to and receive streaming data from device 631 over a wireless local area network (e.g. a Wi-Fi network).

According to some embodiments of the present invention, the 12 lead data is sent by the streaming data sender 665 as it occurs to the streaming data handler 684 where it is stored. The BOA device 104 may perform a discover operation to determine that the CP device 631 supports 12 lead updates. The BOA may then connect to that service supplied by the device 631, and specifically by the report sender, and a persistent connection is formed, according to embodiments of the present invention. Any time the report sender is notified that a new 12 lead has been stored, the report sender will use the established connection to the BOA to send the latest report in the appropriate XML format, according to embodiments of the present invention.

According to some embodiments of the present invention, the patient monitoring device 106 is a defibrillator, or some other device which includes an audio sensor or acoustic cardiograph sensor for recording and/or monitoring and/or retransmitting heart sounds of a patient. Such device may be, for example, an Audicor® acoustic cardiography monitor. In such cases, the audio signal or other acoustic information may be transmitted from the defibrillator monitor board assembly 632 to the SOM processor 633 of the EMS communications interface device 631, for example in streaming fashion, which may then be streamed to another device via Wi-Fi and/or Bluetooth® and/or some other protocol. An electronic stethoscope device may subscribe to and/or connect with EMS communications interface device 631 and be configured to query and/or receive the patient's streaming audio or acoustic information. This may permit a clinician to listen to heart sounds of a patient wirelessly, and even remotely, via a Bluetooth® or other IP information stream. The sound data may be transmitted to remote users for online consultation or case review, according to embodiments of the present invention. Such a device may be a 3M™ Littmann® Electronic Stethoscope, which may be used in this way for real time, or clinical time, tele-auscultation.

The EMS device communications interface 631 may also be used to exchange non-clinical data with the patient monitoring device. According to other embodiments of the present invention, an external device may connect with communications interface device 631 to run a diagnostic test or to install a software update on the underlying patient monitoring device 632. According to yet other embodiments of the present invention, an external device may broadcast the availability of a software update to all subscribing communications interface devices 631, for example those associated with defibrillator devices, which will then alert a user of the devices that an update is available and guide the user through installation. An external device may also connect with communications interface device 631 in order to update the settings or user configuration parameters of the underlying device; for example, BOA device 104 may connect with a defibrillator device 106 at the beginning of each shift in order to change the user configuration settings to match the preferred settings of the active crew member who most recently logged into the system.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A system for providing role-based data feeds for a plurality of caregivers providing medical treatment for a patient, the system comprising:
- at least one portable central device comprising:
  - a patient data display screen, and
  - software modules and hardware configured to feed medical data corresponding to the patient to a plurality of mobile devices via multiple role-based data feeds,
  - the at least one portable central device configured to:
    - obtain the medical data via one or more sensors and/or electrodes configured to couple to the patient,
    - provide the multiple role-based data feeds to the plurality of mobile devices, and
    - display a visual representation of the medical data; and
- the plurality of mobile devices communicatively coupled to the at least one portable central device, each mobile device of the plurality of mobile devices configured to:
  - display a role selection screen that enables a caregiver associated with each mobile device to identify a caregiver role,
  - display a menu of a plurality of selectable interventions based on the caregiver role identified at the role selection screen,
  - interface with the at least one portable central device based on the caregiver role,
  - receive a respective role-based data feed of the multiple role-based data feeds comprising at least a first portion of the medical data from the at least one portable central device, and
  - display a visual representation of the respective role-based data feed.

2. The system of claim 1 wherein each mobile device is configured to
- provide one or more selectable menu options wherein each corresponding menu option indicates a type of medical data associated with the caregiver role; and
- display the visual representation of the respective role-based data feed in response to a selection of the corresponding menu option.

3. The system of claim 1 wherein the plurality of selectable interventions comprise one or more of drug interventions, airway interventions, defibrillation interventions, and CPR interventions.

4. The system of claim 1 wherein at least one of the plurality of selectable interventions is associated with a timer and a selection of the at least one of the plurality of selectable interventions activates the timer.

5. The system of claim 1 wherein each mobile device is configured to display a plurality of graphic icons, each graphic icon corresponding to one of the plurality of selectable interventions.

6. The system of claim 1 wherein the visual representation of the respective role-based data feed includes color-coded information.

7. The system of claim 1 wherein each mobile device is configured to exclude at least a second portion of the medical data from the visual representation of the respective role-based data feed based on the caregiver role wherein the medical data comprises one or more of patient information, a chief complaint, an ECG, CPR information, capnography and pulse oximetry information.

8. The system of claim 1 wherein the medical data corresponds to a plurality of patients comprising at least a first patient and a second patient and wherein each mobile device of the plurality of mobile devices is configured to toggle between a first display of medical data for the first patient and a second display of medical data for the second patient.

9. The system of claim 1, wherein the respective role-based data feed comprises CPR feedback data comprising chest compression data and ventilation data.

10. The system of claim 9, wherein the medical data obtained via the one or more sensors and/or electrodes comprises an ECG waveform and the CPR feedback data, and wherein the respective role-based data feed excludes the ECG waveform.

11. The system of claim 9, wherein the chest compression data comprises compression rate data and compression depth data, and wherein the visual representation of the respective role-based data feed comprises a representation of the compression rate data, a representation of the compression depth data, and qualitative indicator that provides combined visual feedback relating to depth and rate of chest compressions.

12. The system of claim 9, wherein the ventilation data comprises information about a rate and volume of patient ventilation.

13. The system of claim 1, wherein the at least one portable central device is configured to communicatively couple with the plurality of mobile devices via a computer network connection, a short range wireless radio frequency connection, a cellular network connection, or a combination thereof.

14. The system of claim 1 wherein the plurality of mobile devices comprises a lead medic device and one or more of: a drug medic mobile device, an airway medic mobile device, and a cardiopulmonary resuscitation (CPR) medic mobile device.

15. The system of claim 1, wherein each mobile device of the plurality of mobile devices comprises software with a role-based configuration.

16. The system of claim 1, wherein the caregiver role corresponds to one or more tasks determined by a status of the patient, the one or more tasks comprising one or more of a drug administration, a cardiopulmonary resuscitation (CPR) administration, an airway intervention, and a defibrillation intervention.

17. The system of claim 1, wherein the caregiver role is determined by one or more of the plurality of caregivers and a status of the patient.

18. The system of claim 1 wherein each mobile device is configured to exclude a second portion of the medical data from the visual representation of the respective role-based data feed based on the caregiver role, the second portion being different than the first portion.

19. The system of claim 1 wherein;

each mobile device is configured to: provide one or more selectable menu options based on the caregiver role comprising one or more types of the plurality of selectable interventions; and displaying the visual representation of the respective role-based data feed is performed in response to a menu option selection.

20. The system of claim 1, wherein the medical data comprises one or more of an ECG, blood oxygen information, patient information, chief complaint, chest compression bar graphs, an optimal compression depth range, a CPR quality indicator, and CPR feedback.

21. The system of claim 20, wherein the one or more sensors and/or electrodes are configured to be coupled to at least one clinical device communicatively coupled to the at least one portable central device.

22. The system of claim 20, wherein the medical data further includes an indication that a parameter is outside of an acceptable range or value.

23. The system of claim 1, wherein each mobile device is further configured to provide at least one data entry option based on the caregiver role.

* * * * *